(12) United States Patent
Tsantrizos et al.

(10) Patent No.: US 7,939,545 B2
(45) Date of Patent: May 10, 2011

(54) INHIBITORS OF HUMAN IMMUNODEFICIENCY VIRUS REPLICATION

(75) Inventors: Youla S. Tsantrizos, Montreal (CA); Michael Boes, Munich (DE); Christian Brochu, Blainville (CA); Craig Fenwick, Montreal (CA); Stephen Mason, Dorval (CA); Marc Pesant, St-Colomban (CA); Eric Malenfant, Rosemere (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1005 days.

(21) Appl. No.: 11/746,303

(22) Filed: May 9, 2007

(65) Prior Publication Data
US 2008/0221159 A1 Sep. 11, 2008

Related U.S. Application Data

(60) Provisional application No. 60/747,311, filed on May 16, 2006.

(51) Int. Cl.
*A61K 31/04* (2006.01)
*C07D 215/38* (2006.01)

(52) U.S. Cl. ........ 514/312; 514/311; 546/187; 546/185; 546/173; 546/174

(58) Field of Classification Search .................. 546/187, 546/158, 173, 174; 514/312, 311
See application file for complete search history.

(56) References Cited

U.S. PATENT DOCUMENTS 5,700,810 A * 12/1997 Natsugari et al. ............. 514/307
5,731,321 A * 3/1998 Mederski et al. ............. 514/291

FOREIGN PATENT DOCUMENTS

| JP | 01063518 | * | 3/1989 |
| JP | 03227923 | | 10/1991 |
| WO | 9933825 | | 7/1999 |
| WO | 0157021 A2 | | 8/2001 |
| WO | 03039539 | * | 5/2003 |
| WO | 2005058834 A2 | | 6/2005 |

OTHER PUBLICATIONS

Cheng, CA 149:555088, abstract only of Org Reactions, vol. 28, 1982.*
Mederski, Bioorg & Med Chem Lett, vol. 7(14), pp. 1883-1886, 1997.*
Anzini, J Med chem, vol. 38(14), pp. 2692-2704, 1995.*
Sivakamasundari, CA109:37756, abstract only of Indian J Chem, Section B: Organic Chem Including MEd Chem, vol. 26B(8), pp. 744-747, 1987.*
Paramasivam, CA 102:6166, abstract only of Indian J chem, SectionB: Organic Chem Including Med Chem, vol. 23B(4), pp. 311-315, 1984.*
paramasivam, CA 88:50624, abstract only of Synthesis, vol. 11, pp. 768-770, 1977.*
Ali, CA 80:82604, abstract only of Acta Chimica Academiae Scientiarum Hungaricae, vol. 79(4), pp. 455-456, 1973.*
Kohl, CA 80:82600, abstract only of J Pharm Sci, vol. 62(12), pp. 2028-2030, 1973.*
Iove, CA 75:140663, abstract only of J Med Chem, vol. 14(9), pp. 849-852, 1971.*
Fehnel, CA 68:49420, abstract only of J Het Chem, vol. 4(4), pp. 565-570, 1967.*
Sekar, et al; Quinoline Alkaloids: Synthesis of Pyrano[2,3-b]quinolines, Khaplofoline, Lunacrine, and Demethoxylunacrine; Journal of Natural Products; 1998; vol. 61; pp. 294-296.
International Search Report (PCT/ISA/210) for corresponding PCT/CA2007/000845, Aug. 31, 2007.

* cited by examiner

*Primary Examiner* — D. Margaret Seaman
(74) *Attorney, Agent, or Firm* — Michael P. Morris; Alan R. Stempel

(57) ABSTRACT

Compounds of formula I:

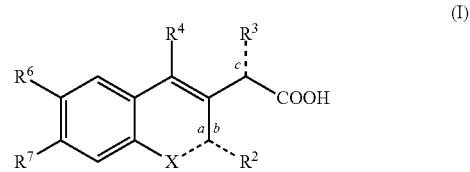

(I)

wherein a, b, c, X, $R^2$, $R^3$, $R^4$, $R^6$ and $R^7$ are defined herein, are useful as inhibitors of HIV replication.

30 Claims, No Drawings

US 7,939,545 B2

INHIBITORS OF HUMAN IMMUNODEFICIENCY VIRUS REPLICATION

RELATED APPLICATIONS

This application claims benefit of U.S. Ser. No. 60/747,311, filed May 16, 2006.

FIELD OF THE INVENTION

The present invention relates to compounds, compositions and methods for the treatment of human immunodeficiency virus (HIV) infection. In particular, the present invention provides novel inhibitors of HIV replication, pharmaceutical compositions containing such compounds and methods for using these compounds in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes, with one additional approved drug targeting gp41 to inhibit viral entry. Within the reverse transcriptase inhibitor and protease inhibitor classes, resistance of HIV to existing drugs is a problem. Therefore, it is important to discover and develop new antiretroviral compounds.

Japanese patent application 03-227923 describes coumarins with anti-HIV activity.

A compound of the formula:

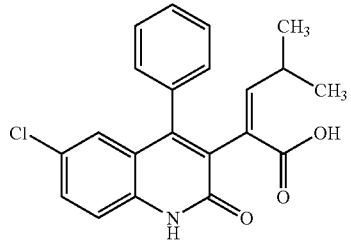

is described as a synthetic intermediate in the synthesis of pyrano[2,3-b]quinoline alkaloids in M. Sekar and K. J. Rajendra Prasad (1998) *J. Nat. Prod.* 61: 294-296.

SUMMARY OF THE INVENTION

The present invention provides a novel series of compounds having inhibitory activity against HIV replication. Furthermore, representative compounds of the invention have activity as inhibitors in a cell-based HIV replication assay. Further objects of this invention arise for the one skilled in the art from the following description and the examples.

One aspect of the invention provides compounds of formula (I):

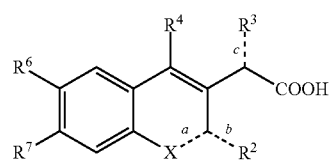

(I)

wherein
bond a is a double bond and bond b is a single bond or
bond a is a single bond and bond b is a double bond;
X is O or $NR^1$ when bond a is a single bond;
or X is N when bond a is a double bond;
$R^1$ is H, $(C_{1-6})$alkyl, $(C_{1-6})$haloalkyl, $(C_{3-7})$cycloalkyl-$(C_{1-6})$alkyl-, aryl-$(C_{1-6})$alkyl- or Het-$(C_{1-6})$alkyl-;
wherein each of the $(C_{1-6})$alkyl, $(C_{3-7})$cycloalkyl-$(C_{1-6})$alkyl-, aryl-$(C_{1-6})$alkyl- and Het-$(C_{1-6})$alkyl- is optionally substituted with —OH, —O$(C_{1-6})$alkyl, —SH, —S$(C_{1-6})$alkyl, —$NH_2$, —NH$(C_{1-6})$alkyl or —N($(C_{1-6})$alkyl)$_2$;
$R^2$ is H, $(C_{1-6})$alkyl or —O$(C_{1-6})$alkyl when bond b is a single bond;
or $R^2$ is O when bond b is a double bond;
$R^3$ is $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- or —Y—$R^{31}$, and
bond c is a single bond; or
$R^3$ is $(C_{1-6})$alkylidene and bond c is a double bond;
wherein Y is O or S and $R^{31}$ is $(C_{1-6})$alkyl, $(C_{1-6})$haloalkyl, $(C_{2-6})$alkenyl, $(C_{2-6})$alkynyl, $(C_{3-7})$cycloalkyl, aryl, $(C_{3-7})$cycloalkyl-$(C_{1-6})$alkyl-, aryl-$(C_{1-6})$alkyl- or Het-$(C_{1-6})$alkyl-;
wherein each of the $(C_{1-6})$alkylidene, $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- and —Y—$R^{31}$ is optionally substituted with 1 to 3 substituents each independently selected from $(C_{1-6})$alkyl, halo, cyano, oxo and —O$(C_{1-6})$alkyl;
$R^4$ is aryl or Het, wherein each of the aryl and Het is optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —S$(C_{1-6})$alkyl, —$NH_2$, —NH$(C_{1-6})$alkyl and —N($(C_{1-6})$alkyl)$_2$; wherein the $(C_{1-6})$alkyl is optionally substituted with hydroxy, cyano or oxo;
$R^6$ and $R^7$ are each independently selected from H, halo, $(C_{1-6})$alkyl and $(C_{1-6})$haloalkyl;
with the proviso that when
bond a is a single bond and bond b is a double bond; and
X is $NR^1$; $R^1$ is H; and $R^2$ is O; and
$R^4$ is unsubstituted phenyl; $R^6$ is Cl; $R^7$ is H; and
bond c is a double bond; then
$R^3$ is not =CH—CH(CH$_3$)$_2$; and
wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;
or a salt or an ester thereof.

Another aspect of this invention provides a compound of formula (I) or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a mammal having or at risk of having the infection.

A further aspect of the invention involves a method of treating an HIV infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating an HIV infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of an HIV infection in a mammal having or at risk of having the infection.

Another aspect of this invention provides the use of a compound of formula (I) as described herein, or a pharmaceutically acceptable salt or ester thereof, for the manufacture of a medicament for the treatment of an HIV infection in a mammal having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt or ester thereof.

Still another aspect of this invention relates to a method of inhibiting the replication of HIV comprising exposing the virus to an effective amount of the compound of formula (I), or a salt or ester thereof, under conditions where replication of HIV is inhibited.

Further included in the scope of the invention is the use of a compound of formula (I), or a salt or ester thereof, to inhibit the replication of HIV.

Yet another aspect of the invention provides a derivative of a compound of formula (I), the derivative comprising a detectable label.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylidene" as used herein, wherein n is an integer, either alone or in combination with another radical, is intended to mean acyclic, straight or branched chain alkyl radicals containing from 1 to n carbon atoms which are bonded to a molecule or fragment thereof, as a substituent thereof, by a double bond. "$(C_{1-6})$alkylidene" includes, but is not limited to, $CH_2=$, $CH_3CH=$, $CH_3CH_2CH=$,

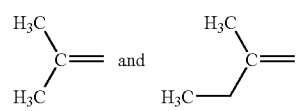

groups. Unless specified otherwise, the term "$(C_{2-n})$alkylidene" is understood to encompass individual stereoisomers where possible, including but not limited to (E) and (Z) isomers, and mixtures thereof. When a $(C_{2-n})$alkylidene group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise, such that the substitution would give rise to a chemically stable compound, such as are recognized by those skilled in the art.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S, unless specified otherwise. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzopyran, benzodioxole, benzodioxane, benzothiazole, quinoline, isoquinoline, and naphthyridine, and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The terms "—S—$(C_{1-n})$alkyl" or "$(C_{1-n})$alkylthio" as used herein interchangeably, wherein n is an integer, either alone or in combination with another radical, is intended to mean an sulfur atom further bonded to an alkyl radical having 1 to n carbon atoms as defined above. Examples of —S—$(C_{1-n})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "thioxo" as used herein is intended to mean an sulfur atom attached to a carbon atom as a substituent by a double bond (=S).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides (RCONHSO$_2$NR$_2$), and N-acylsulfonamides (RCONHSO$_2$R).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

The following designation

is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985). Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by HIV. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "inhibitor of HIV replication" as used herein is intended to mean an agent capable of reducing or eliminating the ability of HIV to replicate in a host cell, whether in vitro, ex vivo or in vivo.

PREFERRED EMBODIMENTS

In the following preferred embodiments, groups and substituents of the compounds according to this invention are described in detail.

Core:

Core-A: In one embodiment, X is O or $NR^1$; a is a single bond and b is a double bond. In this embodiment, the compounds of the invention are represented by formula (Ia):

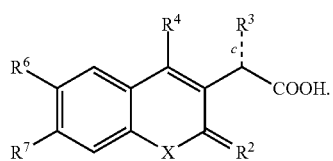

(Ia)

wherein c, $R^1$, $R^2$, $R^3$, $R^4$, $R^6$ and $R^7$ are as defined herein.

Core-B: In another embodiment, X is O; a is a single bond; and b is a double bond. In this embodiment, the compounds of the invention are represented by formula (Ib):

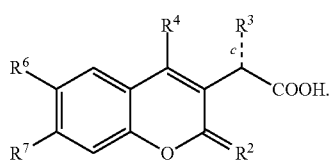

(Ib)

wherein c, $R^2$, $R^3$, $R^4$, $R^6$ and $R^7$ are as defined herein.

Core-C: In another embodiment, X is $NR^1$; a is a single bond; and b is a double bond. In this embodiment, the compounds of the invention are represented by formula (Ic):

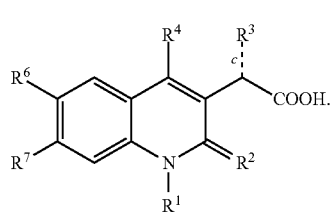

(Ic)

wherein c, $R^1$, $R^2$, $R^3$, $R^4$, $R^6$ and $R^7$ are as defined herein.

It will be apparent to one skilled in the art that when $R^1$ is H and $R^2$ is O, compounds of formula (Ic) can exist in two possible tautomeric forms, (Ic-1) and (Ic-2), as shown below:

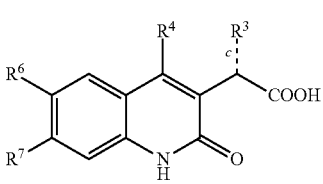

(Ic-1)

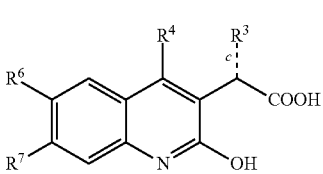

(Ic-2)

Core-D: In an alternative embodiment, X is N; a is a double bond; and b is a single bond. In this embodiment, the compounds of the invention are represented by formula (Id):

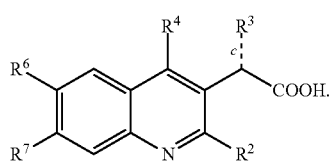

(Id)

wherein c, $R^2$, $R^3$, $R^4$, $R^6$ and $R^7$ are as defined herein.

It will be apparent to a person skilled in the art that, when bond c is a single bond, the carbon atom bonded to the —COOH and $R^3$ substituents can exist in two possible stereochemical configurations, as shown in formulas (Ie) and (If) below:

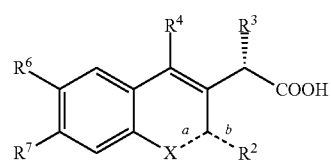

(Ie)

-continued

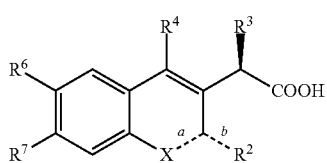
(If)

wherein a, b, X, $R^1$, $R^2$, $R^3$, $R^4$, $R^6$ and $R^7$ are as defined herein.

It has been found that compounds of formula (Ie) have improved activity over compounds of formula (If).

Core-E: Therefore, in one embodiment, the compounds of the present invention are represented by formula (Ie):

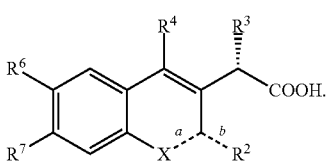
(Ie)

wherein a, b, X, $R^2$, $R^3$, $R^4$, $R^6$ and $R^7$ are as defined herein.

Core-F: In another embodiment, the compounds of the present invention are represented by formula (If):

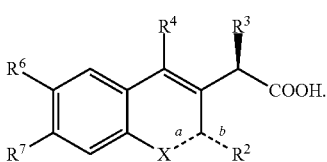
(If)

wherein a, b, X, $R^2$, $R^3$, $R^4$, $R^6$ and $R^7$ are as defined herein.

Core-G: In another embodiment, the compounds of the invention are represented by formula (Ig):

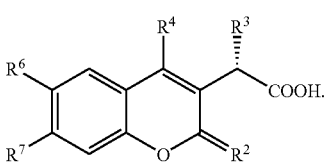
(Ig)

wherein $R^2$, $R^3$, $R^4$, $R^6$ and $R^7$ are as defined herein.

Core-H: In another embodiment, the compounds of the invention are represented by formula (Ih):

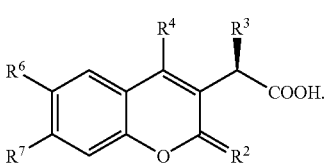
(Ih)

wherein $R^2$, $R^3$, $R^4$, $R^6$ and $R^7$ are as defined herein.

Core-I: In another embodiment, the compounds of the invention are represented by formula (Ii):

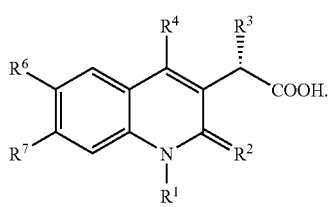
(Ii)

wherein $R^1$, $R^2$, $R^3$, $R^4$, $R^6$ and $R^7$ are as defined herein.

Core-J: In another embodiment, the compounds of the invention are represented by formula (Ij):

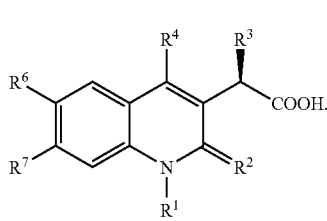
(Ij)

wherein $R^1$, $R^2$, $R^3$, $R^4$, $R^6$ and $R^7$ are as defined herein.

It will be apparent to one skilled in the art that when $R^1$ is H and $R^2$ is O, compounds of formula (Ii) and (Ij) can each also exist in two possible tautomeric forms, as described for compounds of formula (Ic) above.

Core-K: In an alternative embodiment, the compounds of the invention are represented by formula (Ik):

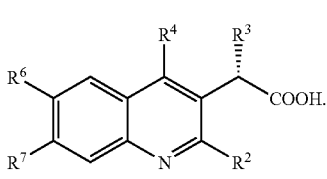
(Ik)

wherein $R^2$, $R^3$, $R^4$, $R^6$ and $R^7$ are as defined herein.

Core-M: In an alternative embodiment, the compounds of the invention are represented by formula (Im):

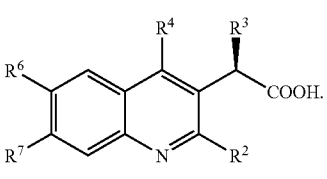
(Im)

wherein $R^2$, $R^3$, $R^4$, $R^6$ and $R^7$ are as defined herein.

Any and each individual definition of a, b and X as set out herein may be combined with any and each individual definition of c, $R^2$, $R^3$, $R^4$, $R^6$ and $R^7$ as set out herein.

$R^1$:

$R^1$-A: In one embodiment, when X is —$NR^1$, $R^1$ is H, $(C_{1-6})$alkyl, $(C_{3-7})$cycloalkyl-$(C_{1-6})$alkyl-, or Het-$(C_{1-6})$alkyl-;
wherein Het is a 4- to 7-membered heterocycle having 1 to 3 heteroatoms each independently selected from N, O and S;

and wherein each of the $(C_{1-6})$alkyl, $(C_{3-7})$cycloalkyl-$(C_{1-6})$alkyl-, and Het-$(C_{1-6})$alkyl- is optionally substituted with —OH, —O$(C_{1-3})$alkyl, —NH$_2$, —NH$(C_{1-3})$alkyl or —N$((C_{1-3})$alkyl$)_2$.

$R^1$-B: In another embodiment, when X is —NR$^1$, R$^1$ is H, $(C_{1-6})$alkyl, $(C_{3-7})$cycloalkyl-$(C_{1-6})$alkyl- or Het-$(C_{1-6})$alkyl-;

wherein Het is a 5- or 6-membered heterocycle having 1 or 2 heteroatoms each independently selected from N, O and S;

and wherein the $(C_{1-6})$alkyl is optionally substituted with —OCH$_3$ or —NH$_2$.

$R^1$-C: In still another embodiment, when X is —NR$^1$, R$^1$ is H, CH$_3$, CH$_2$CH$_3$,

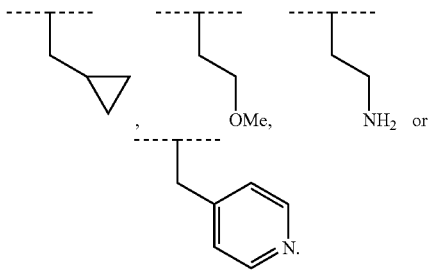

Any and each individual definition of R$^1$ as set out herein may be combined with any and each individual definition of c, R$^3$, R$^4$, R$^6$ and R$^7$ as set out herein.

R$^2$:

$R^2$-A: In one embodiment, when bond b is a double bond, R$^2$ is O.

$R^2$-B: In an alternative embodiment, when bond b is a single bond, R$^2$ is $(C_{1-6})$alkyl or —O$(C_{1-6})$alkyl.

$R^2$-C: In another embodiment, when bond b is a single bond, R$^2$ is $(C_{1-6})$alkyl.

$R^2$-D: In another embodiment, when bond b is a single bond, R$^2$ is —O$(C_{1-6})$alkyl.

$R^2$-E: In another embodiment, when bond b is a single bond, R$^2$ is —CH$_3$, —CH$_2$CH$_3$, —CH$_2$CH$_2$CH$_3$, —CH(CH$_3$)$_2$, —OCH$_3$, —OCH$_2$CH$_3$, —OCH$_2$CH$_2$CH$_3$, or —OCH(CH$_3$)$_2$.

$R^2$-F: In another embodiment, when bond b is a single bond, R$^2$ is —CH$_3$, —CH$_2$CH$_3$, —CH(CH$_3$)$_2$, or —OCH$_3$.

$R^2$-G: In another embodiment, when bond b is a single bond, R$^2$ is —CH$_3$ or —CH$_2$CH$_3$.

$R^2$-H: In another embodiment, when bond b is a single bond, R$^2$ is —CH$_3$.

Any and each individual definition of b and R$^2$ as set out herein may be combined with any and each individual definition of c, X, R$^1$, R$^3$, R$^4$, R$^6$ and R$^7$ as set out herein.

R$^3$:

$R^3$-A: In one embodiment, R$^3$ is $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl- or Het-$(C_{1-6})$alkyl-;

wherein each of the $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl- and Het-$(C_{1-6})$alkyl- is optionally substituted with 1 to 3 substituents each independently selected from $(C_{1-6})$alkyl, halo, cyano, oxo and —O$(C_{1-6})$alkyl; and bond c is a single bond.

$R^3$-B: In another embodiment, R$^3$ is $(C_{1-6})$alkyl or $(C_{2-6})$alkenyl; and bond c is a single bond.

$R^3$-C: In another embodiment, R$^3$ is $(C_{1-6})$alkylidene and bond c is a double bond.

$R^3$-D: In another embodiment, R$^3$ is selected from:
—CH$_2$CH$_2$CH$_3$, —CH$_2$CH(CH$_3$)$_2$, —CH$_2$CH=CH$_2$ and —CH$_2$C(CH$_3$)=CH$_2$; and bond c is a single bond;

or R$^3$ is =CHCH$_2$CH$_3$ and bond c is a double bond.

$R^3$-E: In an alternative embodiment, R$^3$ is —Y—$(C_{1-6})$alkyl, —Y—$(C_{1-6})$haloalkyl, —Y—$(C_{2-6})$alkenyl, —Y—$(C_{2-6})$alkynyl, —Y—$(C_{3-7})$cycloalkyl, —Y-aryl, $(C_{3-7})$cycloalkyl-$(C_{1-6})$alkyl-Y—, aryl-$(C_{1-6})$alkyl-Y— or Het-$(C_{1-6})$alkyl-Y—;

wherein Y is O or S; and wherein each of the —Y—$(C_{1-6})$alkyl, —Y—$(C_{2-6})$alkenyl, —Y—$(C_{2-6})$alkynyl, —Y—$(C_{3-7})$cycloalkyl, —Y-aryl, $(C_{3-7})$cycloalkyl-$(C_{1-6})$alkyl-Y—, aryl-$(C_{1-6})$alkyl-Y— and Het-$(C_{1-6})$alkyl-Y— is optionally substituted with 1 to 3 substituents each independently selected from $(C_{1-6})$alkyl, halo, cyano, oxo and —O$(C_{1-6})$alkyl; and bond c is a single bond.

$R^3$-F: In another embodiment, R$^3$ is —O—$(C_{1-6})$alkyl, —O—$(C_{1-6})$haloalkyl, —O—$(C_{2-6})$alkenyl, —O—$(C_{2-6})$alkynyl, —O—$(C_{3-7})$cycloalkyl, —O-aryl, $(C_{3-7})$cycloalkyl-$(C_{1-6})$alkyl-O—, aryl-$(C_{1-6})$alkyl-O— or Het-$(C_{1-6})$alkyl-O—;

wherein each of the —O—$(C_{1-6})$alkyl, —O—$(C_{2-6})$alkenyl, —O—$(C_{2-6})$alkynyl, —O—$(C_{3-7})$cycloalkyl, —O-aryl, $(C_{3-7})$cycloalkyl-$(C_{1-6})$alkyl-O—, aryl-$(C_{1-6})$alkyl-O— and Het-$(C_{1-6})$alkyl-O— is optionally substituted with 1 to 3 substituents each independently selected from $(C_{1-6})$alkyl, halo, cyano, oxo and —O$(C_{1-6})$alkyl; and bond c is a single bond.

$R^3$-G: In another embodiment, R$^3$ is —O$(C_{1-6})$alkyl, —O—$(C_{1-6})$haloalkyl, —O—$(C_{2-6})$alkenyl, —O$(C_{2-6})$alkynyl, —O—$(C_{3-7})$cycloalkyl, —O-aryl, $(C_{3-7})$cycloalkyl-$(C_{1-3})$alkyl-O— or Het-$(C_{1-3})$alkyl-O—;

wherein Het is a 5- or 6-membered heterocycle having 1 to 3 heteroatoms each independently selected from N, O and S; and wherein each of the —O$(C_{1-6})$alkyl, —O—$(C_{3-7})$cycloalkyl and Het-$(C_{1-3})$alkyl-O— is optionally substituted with 1 to 3 substituents each independently selected from $(C_{1-3})$alkyl, cyano, oxo and —O$(C_{1-6})$alkyl; and bond c is a single bond.

$R^3$-H: In another embodiment, R$^3$ is —O$(C_{1-6})$alkyl, —O—$(C_{1-6})$haloalkyl, —O$(C_{2-6})$alkenyl, —O$(C_{2-6})$alkynyl or —O—$(C_{3-7})$cycloalkyl;

wherein each of the —O$(C_{1-6})$alkyl and —O—$(C_{3-7})$cycloalkyl is optionally substituted with 1 to 3 substituents each independently selected from $(C_{1-3})$alkyl, cyano, oxo and —O$(C_{1-6})$alkyl; and bond c is a single bond.

$R^3$-I: In another embodiment, R$^3$ is —O$(C_{1-6})$alkyl; wherein the —O$(C_{1-6})$alkyl is optionally substituted with 1 to 3 substituents each independently selected from cyano, oxo and —O$(C_{1-6})$alkyl; and bond c is a single bond.

$R^3$-J: In another embodiment, R$^3$ is —O$(C_{2-4})$alkyl; and bond c is a single bond.

$R^3$-K: In another embodiment, $R^3$ is selected from:

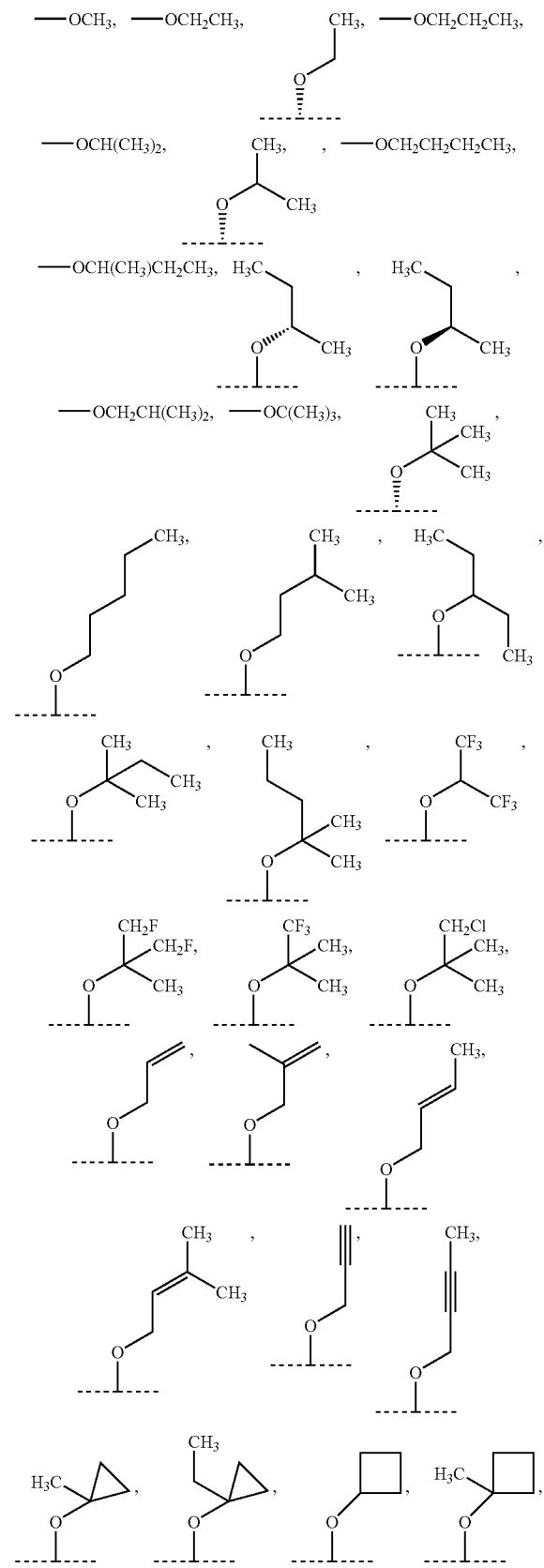

Any and each individual definition of c and $R^3$ as set out herein may be combined with any and each individual definition of a, b, X, $R^1$, $R^2$, $R^4$, $R^6$ and $R^7$ as set out herein.

$R^4$:

$R^4$-A: In one embodiment, $R^4$ is aryl optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —S$(C_{1-6})$alkyl, —NH$_2$, —NH$(C_{1-6})$alkyl and —N$((C_{1-6})$alkyl$)_2$; wherein the $(C_{1-6})$alkyl is optionally substituted with hydroxy, cyano or oxo.

$R^4$-B: In another embodiment, $R^4$ is naphthyl or phenyl, wherein the phenyl is optionally substituted with 1 to 3 substituents each independently selected from halo, $(C_{1-4})$alkyl, $(C_{2-4})$alkenyl, $(C_{1-4})$haloalkyl, $(C_{3-7})$cycloalkyl, —OH, —O$(C_{1-4})$alkyl, —SH, —S$(C_{1-4})$alkyl, —NH$_2$, —NH$(C_{1-4})$alkyl and —N$((C_{1-4})$alkyl$)_2$; wherein the $(C_{1-4})$alkyl is optionally substituted with hydroxy, cyano or oxo.

$R^4$-C: In another embodiment, $R^4$ is phenyl optionally substituted with 1 to 3 substituents each independently selected from halo, $(C_{1-4})$alkyl, $(C_{2-4})$alkenyl, $(C_{1-4})$haloalkyl, $(C_{3-7})$cycloalkyl, —OH, —O$(C_{1-4})$alkyl, —SH, —S$(C_{1-4})$alkyl, —NH$_2$, —NH$(C_{1-4})$alkyl and —N$((C_{1-4})$alkyl$)_2$; wherein the $(C_{1-4})$alkyl is optionally substituted with hydroxy, cyano or oxo.

$R^4$-D: In another embodiment, $R^4$ is phenyl optionally substituted with 1 or 2 substituents each independently selected from F, Cl, Br, —CH$_3$, —CH$_2$CH$_3$, —CH$_2$CH$_2$CH$_3$, —CH(CH$_3$)$_2$, —C(CH$_3$)$_3$, —CH=CH$_2$, CH$_2$F, CF$_3$, —CF$_2$CH$_3$, —CH$_2$CH$_2$F, cyclopropyl, —OH, —OCH$_3$, —OCH$_2$CH$_3$, —SCH$_3$, —N(CH$_3$)$_2$, —CH$_2$OH, —CH$_2$CN and CH$_3$C(=O)—.

$R^4$-E: In another embodiment, $R^4$ is selected from:
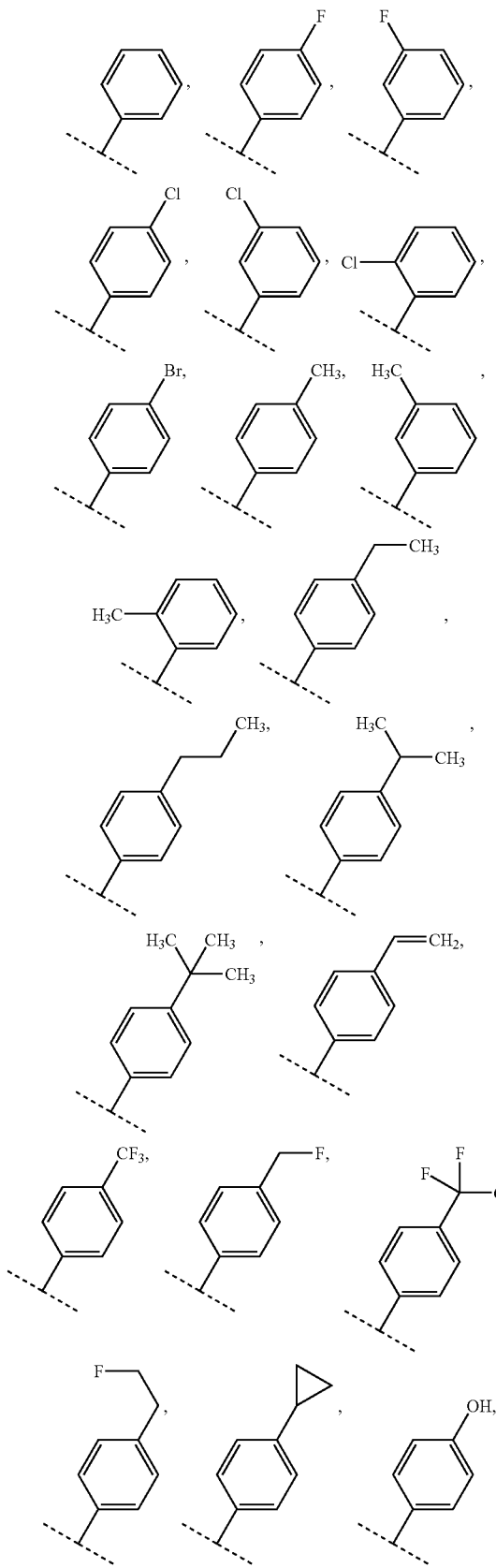
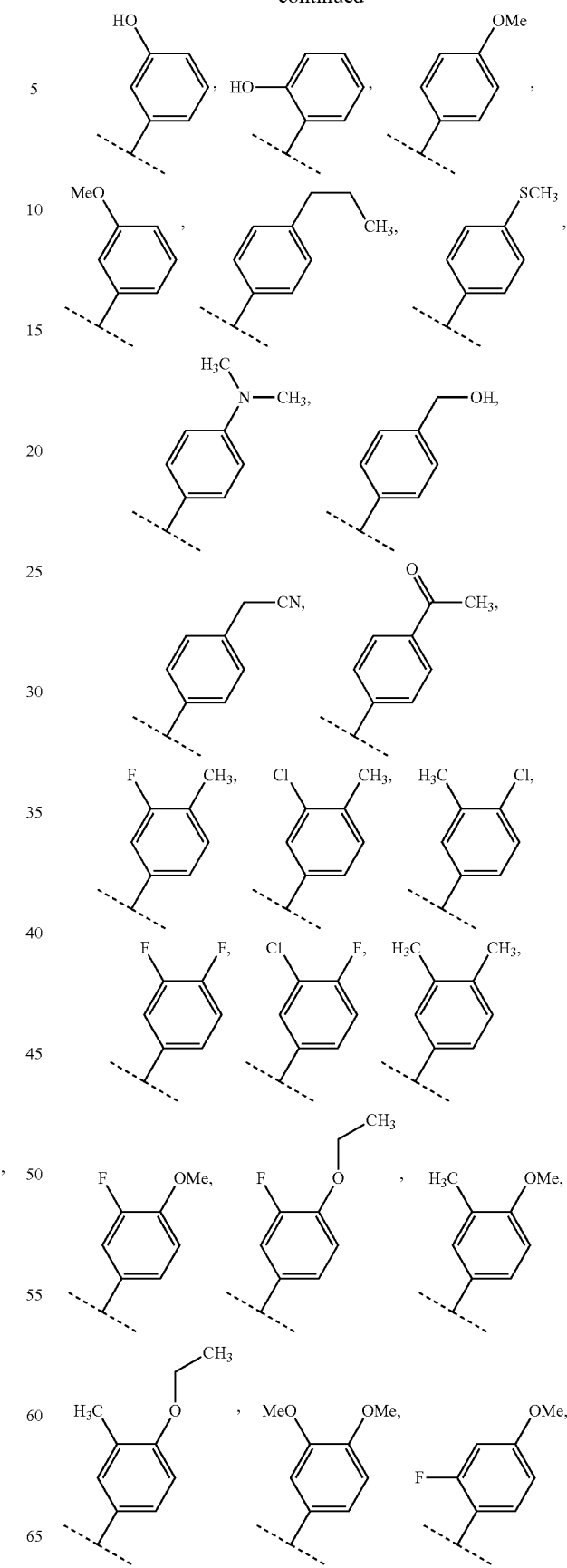

-continued

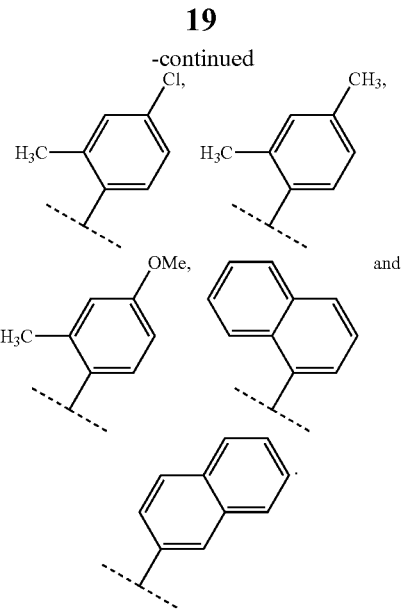

R⁴-F: In another embodiment, R⁴ is a group of formula:

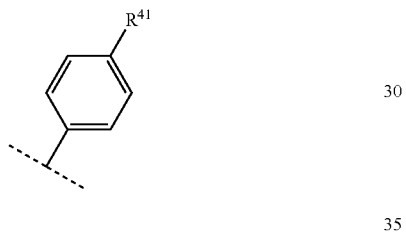

wherein R⁴¹ is selected from halo, $(C_{1-4})$alkyl and $(C_{1-4})$haloalkyl.

R⁴-G: In an alternative embodiment, R⁴ is Het optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —S$(C_{1-6})$alkyl, —NH$_2$, —NH$(C_{1-6})$alkyl and —N$((C_{1-6})$alkyl$)_2$; wherein the $(C_{1-6})$alkyl is optionally substituted with hydroxy, cyano or oxo.

R⁴-H: In another alternative embodiment, R⁴ is Het optionally substituted with 1 to 3 substituents each independently selected from halo, $(C_{1-6})$alkyl and —O$(C_{1-6})$alkyl; wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

R⁴-I: In another alternative embodiment, R⁴ is Het optionally substituted with 1 to 3 substituents each independently selected from halo, $(C_{1-6})$alkyl and —O$(C_{1-6})$alkyl; wherein the Het is selected from:

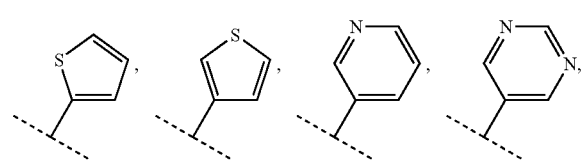

-continued

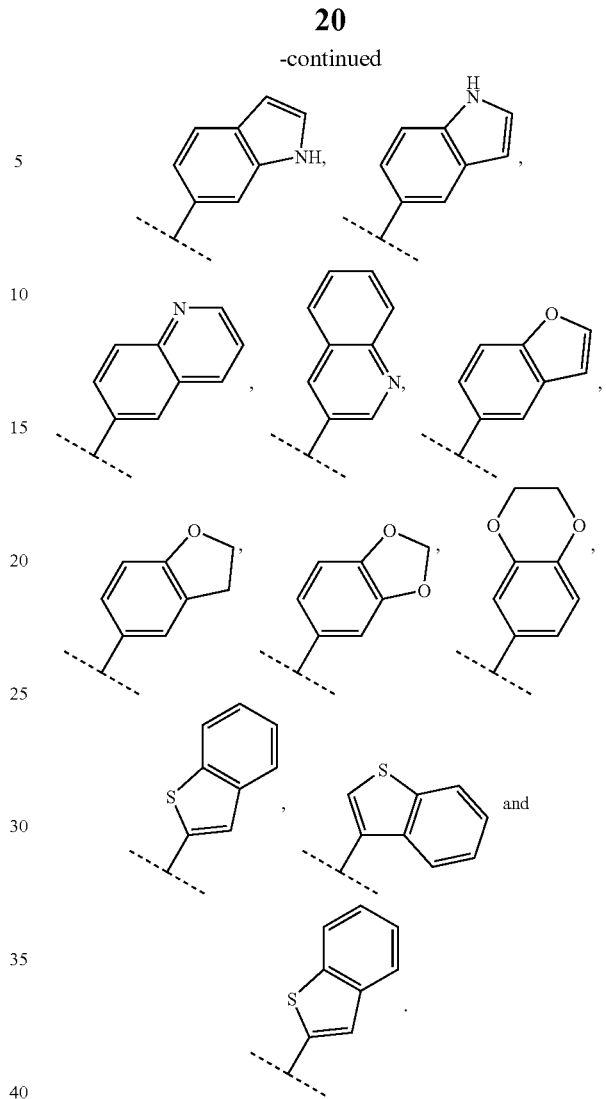

R⁴-J: In another alternative embodiment, R⁴ is selected from:

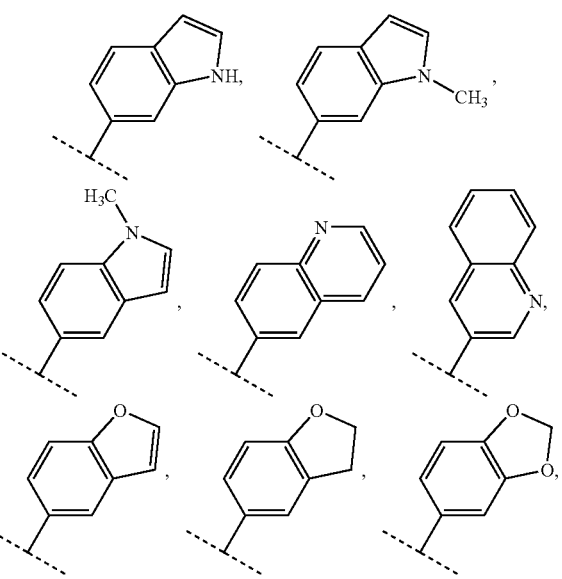

-continued

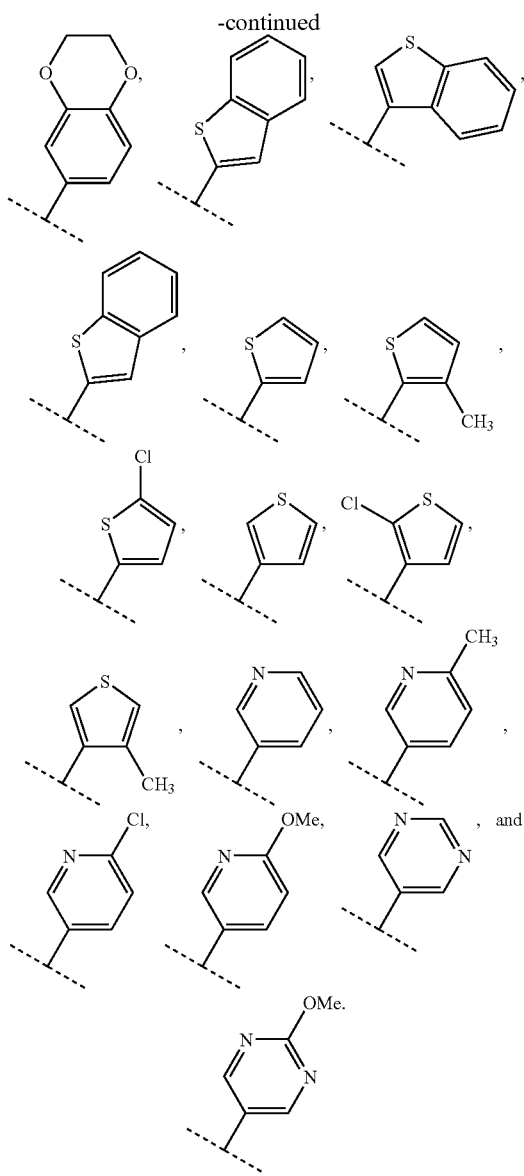

Any and each individual definition of $R^4$ as set out herein may be combined with any and each individual definition of a, b, c, X, $R^1$, $R^2$, $R^3$, $R^6$ and $R^7$ as set out herein.

One skilled in the art will recognize that when the $R^4$ substituent is not symmetrically substituted about the axis of rotation of the bond attaching $R^4$ to Core, rotational isomers or atropisomers are possible. Compounds of the invention in which the $R^4$ substituent is not symmetrically substituted about the axis of rotation of the bond attaching $R^4$ to Core and in which the carbon atom bonded to the —COOH and $R^3$ substituents is chiral, as described above, will have two chiral centers, a chiral carbon atom and a rotational axis of asymmetry, and thus the atropisomers will exist as diastereomers. However, individual diastereomeric atropisomers may or may not be detectable and/or separable, depending upon the relative amounts of each atropisomer present at equilibrium, and the degree of steric hindrance to rotation about this bond, and thus, the rate at which rotation occurs to interconvert these atropisomers. Once separated, individual atropisomers may interconvert, rapidly or slowly, with each other to form an equilibrium mixture of atropisomers.

$R^6$:

$R^6$-A: In one embodiment, $R^6$ is H, halo, $(C_{1-3})$alkyl or $(C_{1-3})$haloalkyl.

$R^6$-B: In another embodiment, $R^6$ is H, F, Cl, Br, $CH_3$ or $CF_3$.

$R^6$-C: In another embodiment, $R^6$ is H, F, Cl or Br.

$R^6$-D: In another embodiment, $R^6$ is H, Cl or Br.

Any and each individual definition of $R^6$ as set out herein may be combined with any and each individual definition of a, b, c, X, $R^1$, $R^2$, $R^3$, $R^4$ and $R^7$ as set out herein.

$R^7$:

$R^7$-A: In one embodiment, $R^7$ is H or F.

$R^7$-B: In another embodiment, $R^7$ is H.

Any and each individual definition of $R^7$ as set out herein may be combined with any and each individual definition of a, b, c, X, $R^1$, $R^2$, $R^3$, $R^4$, $R^6$ and $R^7$ as set out herein.

Examples of preferred subgeneric embodiments of the present invention are set forth in the following table, wherein each substituent group of each embodiment is defined according to the definitions set forth above:

| Embodiment | Core | $R^1$ | $R^2$ | $R^3$ | $R^4$ | $R^6$ | $R^7$ |
|---|---|---|---|---|---|---|---|
| E-1  | Core-B |       | $R^2$—A | $R^3$—B | $R^4$—B | $R^6$—A | $R^7$—A |
| E-2  | Core-G |       | $R^2$—A | $R^3$—B | $R^4$—B | $R^6$—A | $R^7$—A |
| E-3  | Core-C | $R^1$—A | $R^2$—A | $R^3$—B | $R^4$—B | $R^6$—A | $R^7$—A |
| E-4  | Core-I | $R^1$—A | $R^2$—A | $R^3$—B | $R^4$—B | $R^6$—A | $R^7$—A |
| E-5  | Core-D |       | $R^2$—C | $R^3$—B | $R^4$—B | $R^6$—A | $R^7$—A |
| E-6  | Core-K |       | $R^2$—C | $R^3$—B | $R^4$—B | $R^6$—A | $R^7$—A |
| E-7  | Core-D |       | $R^2$—D | $R^3$—B | $R^4$—B | $R^6$—A | $R^7$—A |
| E-8  | Core-K |       | $R^2$—D | $R^3$—B | $R^4$—B | $R^6$—A | $R^7$—A |
| E-9  | Core-B |       | $R^2$—A | $R^3$—C | $R^4$—B | $R^6$—A | $R^7$—A |
| E-10 | Core-G |       | $R^2$—A | $R^3$—C | $R^4$—B | $R^6$—A | $R^7$—A |
| E-11 | Core-C | $R^1$—A | $R^2$—A | $R^3$—C | $R^4$—B | $R^6$—A | $R^7$—A |
| E-12 | Core-I | $R^1$—A | $R^2$—A | $R^3$—C | $R^4$—B | $R^6$—A | $R^7$—A |
| E-13 | Core-D |       | $R^2$—C | $R^3$—C | $R^4$—B | $R^6$—A | $R^7$—A |
| E-14 | Core-K |       | $R^2$—C | $R^3$—C | $R^4$—B | $R^6$—A | $R^7$—A |
| E-15 | Core-D |       | $R^2$—D | $R^3$—C | $R^4$—B | $R^6$—A | $R^7$—A |
| E-16 | Core-K |       | $R^2$—D | $R^3$—C | $R^4$—B | $R^6$—A | $R^7$—A |
| E-17 | Core-B |       | $R^2$—A | $R^3$—F | $R^4$—B | $R^6$—A | $R^7$—A |
| E-18 | Core-G |       | $R^2$—A | $R^3$—F | $R^4$—B | $R^6$—A | $R^7$—A |
| E-19 | Core-C | $R^1$—A | $R^2$—A | $R^3$—F | $R^4$—B | $R^6$—A | $R^7$—A |
| E-20 | Core-I | $R^1$—A | $R^2$—A | $R^3$—F | $R^4$—B | $R^6$—A | $R^7$—A |

-continued

| Embodiment | Core | $R^1$ | $R^2$ | $R^3$ | $R^4$ | $R^6$ | $R^7$ |
|---|---|---|---|---|---|---|---|
| E-21 | Core-D |  | $R^2$—C | $R^3$—F | $R^4$—B | $R^6$—A | $R^7$—A |
| E-22 | Core-K |  | $R^2$—C | $R^3$—F | $R^4$—B | $R^6$—A | $R^7$—A |
| E-23 | Core-D |  | $R^2$—D | $R^3$—F | $R^4$—B | $R^6$—A | $R^7$—A |
| E-24 | Core-K |  | $R^2$—D | $R^3$—F | $R^4$—B | $R^6$—A | $R^7$—A |
| E-25 | Core-B |  | $R^2$—A | $R^3$—B | $R^4$—H | $R^6$—A | $R^7$—A |
| E-26 | Core-G |  | $R^2$—A | $R^3$—B | $R^4$—H | $R^6$—A | $R^7$—A |
| E-27 | Core-C | $R^1$—A | $R^2$—A | $R^3$—B | $R^4$—H | $R^6$—A | $R^7$—A |
| E-28 | Core-I | $R^1$—A | $R^2$—A | $R^3$—B | $R^4$—H | $R^6$—A | $R^7$—A |
| E-29 | Core-D |  | $R^2$—C | $R^3$—B | $R^4$—H | $R^6$—A | $R^7$—A |
| E-30 | Core-K |  | $R^2$—C | $R^3$—B | $R^4$—H | $R^6$—A | $R^7$—A |
| E-31 | Core-D |  | $R^2$—D | $R^3$—B | $R^4$—H | $R^6$—A | $R^7$—A |
| E-32 | Core-K |  | $R^2$—D | $R^3$—B | $R^4$—H | $R^6$—A | $R^7$—A |
| E-33 | Core-B |  | $R^2$—A | $R^3$—C | $R^4$—H | $R^6$—A | $R^7$—A |
| E-34 | Core-G |  | $R^2$—A | $R^3$—C | $R^4$—H | $R^6$—A | $R^7$—A |
| E-35 | Core-C | $R^1$—A | $R^2$—A | $R^3$—C | $R^4$—H | $R^6$—A | $R^7$—A |
| E-36 | Core-I | $R^1$—A | $R^2$—A | $R^3$—C | $R^4$—H | $R^6$—A | $R^7$—A |
| E-37 | Core-D |  | $R^2$—C | $R^3$—C | $R^4$—H | $R^6$—A | $R^7$—A |
| E-38 | Core-K |  | $R^2$—C | $R^3$—C | $R^4$—H | $R^6$—A | $R^7$—A |
| E-39 | Core-D |  | $R^2$—D | $R^3$—C | $R^4$—H | $R^6$—A | $R^7$—A |
| E-40 | Core-K |  | $R^2$—D | $R^3$—C | $R^4$—H | $R^6$—A | $R^7$—A |
| E-41 | Core-B |  | $R^2$—A | $R^3$—F | $R^4$—H | $R^6$—A | $R^7$—A |
| E-42 | Core-G |  | $R^2$—A | $R^3$—F | $R^4$—H | $R^6$—A | $R^7$—A |
| E-43 | Core-C | $R^1$—A | $R^2$—A | $R^3$—F | $R^4$—H | $R^6$—A | $R^7$—A |
| E-44 | Core-I | $R^1$—A | $R^2$—A | $R^3$—F | $R^4$—H | $R^6$—A | $R^7$—A |
| E-45 | Core-D |  | $R^2$—C | $R^3$—F | $R^4$—H | $R^6$—A | $R^7$—A |
| E-46 | Core-K |  | $R^2$—C | $R^3$—F | $R^4$—H | $R^6$—A | $R^7$—A |
| E-47 | Core-D |  | $R^2$—D | $R^3$—F | $R^4$—H | $R^6$—A | $R^7$—A |
| E-48 | Core-K |  | $R^2$—D | $R^3$—F | $R^4$—H | $R^6$—A | $R^7$—A |

Examples of most preferred compounds according to this invention are each single compound listed in the following Tables 1 to 3.

In general, all tautomeric and isomeric forms and mixtures thereof, for example, individual tautomers, geometric isomers, stereoisomers, atropisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

Pharmaceutical Composition

Compounds of the present invention may be administered to a mammal in need of treatment for HIV infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from more than 50% to about 100% of one enantiomer of the active ingredient and from about 0% to less than 50% of the other enantiomer of the active ingredient. Preferably, when the composition comprises a mixture enriched in one enantiomer of the active ingredient or a pure enantiomer of the active ingredient, the composition comprises from more than 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

For oral administration, the compound, or a pharmaceutically acceptable salt or ester thereof, can be formulated in any orally acceptable dosage form including but not limited to aqueous suspensions and solutions, capsules or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 100 milligrams per kilogram of body weight, with the preferred dose being about 0.01 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Therefore, according to one embodiment, the pharmaceutical composition according to the invention comprises a racemic mixture of the compound of formula (I), or a pharmaceutically acceptable salt or ester thereof.

An alternative embodiment provides a pharmaceutical composition comprising a mixture enriched in one enantiomer of the compound of formula (I), or a pharmaceutically acceptable salt or ester thereof.

A further embodiment provides a pharmaceutical composition comprising a pure enantiomer of the compound of formula (I), or a pharmaceutically acceptable salt or ester thereof.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, capravirine, etravirine, rilpivirine and BILR 355);

protease inhibitors (including but not limited to ritonavir, tipranavir, saquinavir, nelfinavir, indinavir, amprenavir, fosamprenavir, atazanavir, lopinavir, VX-385 and TMC-114);

entry inhibitors including but not limited to
 CCR5 antagonists (including but not limited to maraviroc (UK-427,857) and TAK-652),
 CXCR4 antagonists (including but not limited to AMD-11070),
 fusion inhibitors (including but not limited to enfuvirtide (T-20)) and
 others (including but not limited to BMS-488043);

integrase inhibitors (including but not limited to MK-0518, c-1605, BMS-538158 and GS 9137);

TAT inhibitors;

maturation inhibitors (including but not limited to PA-457); and immunomodulating agents (including but not limited to levamisole).

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Derivatives Comprising a Detectable Label

Another aspect of the invention provides a derivative of a compound of formula (I), the derivative comprising a detectable label. Such a label allows recognition either directly or indirectly of the derivative such that it can be detected, measured or quantified. The detectable label may itself be detectable, measurable or quantifiable, or it may interact with one or more other moieties which themselves comprise one or more detectable labels, so that the interaction therebetween allows the derivative to be detected, measured or quantified.

Such derivatives may be used as probes to study HIV replication, including but not limited to study of the mechanism of action of viral and host proteins involved in HIV replication, study of conformational changes undergone by such viral and host proteins under various conditions and study of interactions with entities which bind to or otherwise interact with these viral and host proteins. Derivatives according to this aspect of the invention may be used in assays to identify compounds which interact with viral and host proteins, the assays including but not limited to displacement assays which measure the extent to which the derivative is displaced from interacting with the viral and host proteins. Such derivatives may also be used to form covalent or non-covalent interactions with the viral and host proteins or to identify residues of the viral and host proteins which interact with the compounds of the invention.

Detectable labels contemplated for use with derivatives of the compounds of the invention include, but are not limited to, fluorescent labels, chemiluminescent labels, chromophores, antibodies, enzymatic markers, radioactive isotopes, affinity tags and photoreactive groups.

A fluorescent label is a label which fluoresces, emitting light of one wavelength upon absorption of light of a different wavelength. Fluorescent labels include but are not limited to fluorescein; Texas Red; aminomethylcoumarin; rhodamine dyes, including but not limited to tetramethylrhodamine (TAMRA); Alexa dyes including but not limited to Alexa Fluor® 555; cyanine dyes including but not limited to Cy3; europium or lanthanide series based fluorescent molecules; and the like.

A chemiluminescent label is a label which can undergo a chemical reaction which produces light. Chemiluminescent labels include but are not limited to luminol, luciferin, lucigenin, and the like.

A chromophore is a label which selectively absorbs certain wavelengths of visible light while transmitting or reflecting others, thereby causing the compounds which contain the chromophore to appear colored. Chromophores include but are not limited to natural and synthetic dyes.

An antibody is a protein produced by a mammalian immune system in response to a specific antigen, which binds specifically to that antigen. Antibodies contemplated for use as detectable labels according to the invention include but are not limited to antibodies against the following: polyhistidine tags, glutathione-S-transferase (GST), hemagglutinin (HA), FLAG® epitope tags, Myc tag, maltose binding protein (MBP), green fluorescent protein (GFP) and the like.

An enzymatic marker is an enzyme whose presence may be detected by means of an assay specific to the catalytic activity of the enzyme. Enzymatic markers contemplated for use as detectable labels according to the invention include but are not limited to luciferase, horseradish peroxidase (HRP), β-galactosidase and the like.

A radioactive isotope is an isotope of an atom which produces radiation upon radioactive decay. Radioactive isotopes include but are not limited to $^{14}C$, $^{3}H$, $^{31}P$, $^{121}I$, $^{125}I$ and the like.

An affinity tag is a label which has a strong affinity for another moiety, designated herein as a binding partner. Such an affinity tag can be used to form a complex with the binding partner so that the complex may be selectively detected or separated from a mixture. Affinity tags include but are not limited to biotin or a derivative thereof, a histidine polypeptide, a polyarginine, an amylose sugar moiety or a defined epitope recognizable by a specific antibody; suitable epitopes include but are not limited to glutathione-S-transferase (GST), hemagglutinin (HA), FLAG® epitope tags, Myc tag, maltose binding protein (MBP), green fluorescent protein (GFP) and the like.

Furthermore, compounds of the invention used as probes may be labelled with a photoreactive group which is transformed, upon activation by light, from an inert group to a reactive species, such as a free radical. Such a group may be used to activate the derivative so that it can form a covalent bond with one or more residues of a viral or host protein. Photoreactive groups include but are not limited to photoaffinity labels such as benzophenone and azide groups.

One embodiment of the derivative of a compound of formula (I) according to the invention has the formula (Ic'):

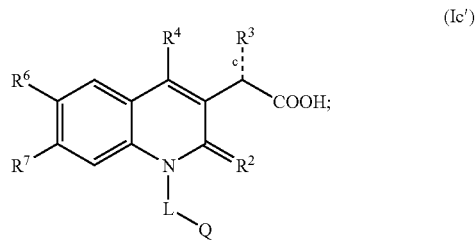

(Ic')

wherein L is a linker;
Q is a detectable label; and
c, $R^2$, $R^3$, $R^4$, $R^6$ and $R^7$ are as defined herein.

An alternative embodiment of the derivative of a compound of formula (I) according to the invention has the formula (Ii')

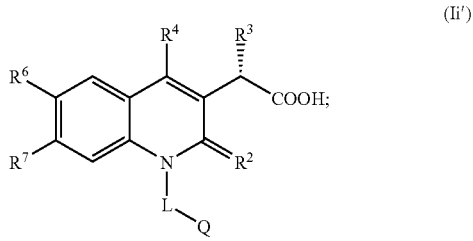

wherein L is a linker;
Q is a detectable label; and
$R^2$, $R^3$, $R^4$, $R^6$ and $R^7$ are as defined herein.

In one embodiment, Q is selected from a fluorescent label, a chemiluminescent label, a chromophore, an antibody, an enzymatic marker, a radioactive isotope, an affinity tag and a photoreactive group.

In another embodiment, Q is a fluorescent label or an affinity tag.

In yet another embodiment, Q is selected from biotin, fluorescein, TAMRA, Alexa Fluor® 555, Cy3, europium or lanthanide series based fluorescent molecules, polyhistidine tags, glutathione-S-transferase (GST), hemagglutinin (HA), FLAG® epitope tags, Myc tag and a radioactive isotope selected from $^{14}C$, $^{3}H$, $^{31}P$, $^{121}I$ and $^{125}I$.

It is contemplated that the linker L may be any chemically stable group which acts to place the detectable label Q in an appropriate position relative to the compound of the invention and/or to any other moiety or moieties with which it interacts, so that the derivative of the compound of the invention may be detected, measured or quantified.

Therefore, in one embodiment, when Q is a fluorescent label or an affinity tag, the linker L comprises a plurality of atoms, each independently selected from C, O, N and S; the atoms being bonded to form a linear or branched chain which optionally comprise one or more carbocyclic or heterocyclic rings; such that the average distance between the N atom to which L is bonded and Q is from about 2 Å to about 100 Å.

In another embodiment, when Q is a fluorescent label or an affinity tag, the linker L comprises a plurality of atoms, each independently selected from C, O, N and S; the atoms being bonded to form a linear or branched chain which optionally comprise one or more carbocyclic or heterocyclic rings; such that the average distance between the N atom to which L is bonded and Q is from about 10 Å to about 50 Å.

In yet another embodiment, when Q is a fluorescent label or an affinity tag, the linker L comprises a plurality of atoms, each independently selected from C, O, N and S; the atoms being bonded to form a linear or branched chain which optionally comprise one or more carbocyclic or heterocyclic rings; such that the average distance between the N atom to which L is bonded and Q is from about 25 Å to about 35 Å.

In an alternative embodiment, when Q is a fluorescent label or an affinity tag, the linker L comprises a linear chain of from 1 to 100 atoms, each independently selected from C, O, N and S; the linear chain optionally comprising from one to five carbocyclic or heterocyclic rings and being optionally substituted with $(C_{1-6})$alkyl, halo, —O—$(C_{1-6})$alkyl, oxo or thioxo.

In another alternative embodiment, when Q is a fluorescent label or an affinity tag, the linker L comprises a linear chain of from 10 to 50 atoms, each independently selected from C, O, N and S; the linear chain optionally comprising from one to three carbocyclic or heterocyclic rings and being optionally substituted with $(C_{1-6})$alkyl, halo, —O—$(C_{1-6})$alkyl, oxo or thioxo.

A specific example of a derivative according to the invention has the following formula D1:

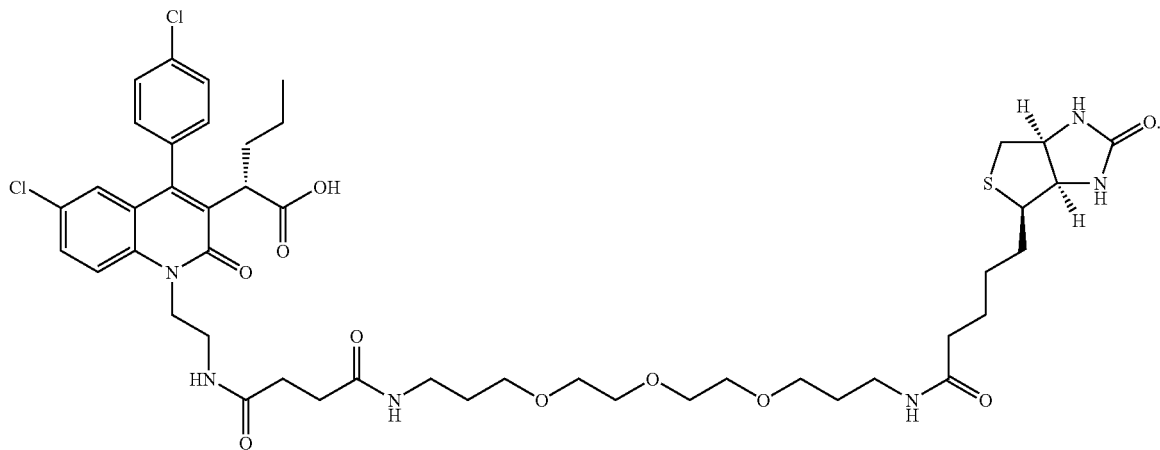

Methodology and Synthesis

The synthesis of compounds of formula (I) according to this invention is conveniently accomplished following the general procedure outlined in the schemes below wherein a, b, c, X, $R^2$, $R^3$, $R^4$, $R^6$ and $R^7$ are as defined herein. Further instruction is provided to one skilled in the art by the specific examples set out hereinbelow.

Compounds of formula (Ia) wherein X is O or $NR^1$, bond c is a single bond, $R^2$ is O, $R^3$ is an optionally substituted alkyl, alkenyl or alkynyl group as defined herein, including a haloalkyl, cycloalkyl-alkyl, aryl-alkyl or Het-alkyl group, and $R^1$, $R^4$, $R^6$ and $R^7$ are as defined herein may be prepared as outlined in Scheme 1 below.

Scheme 1:

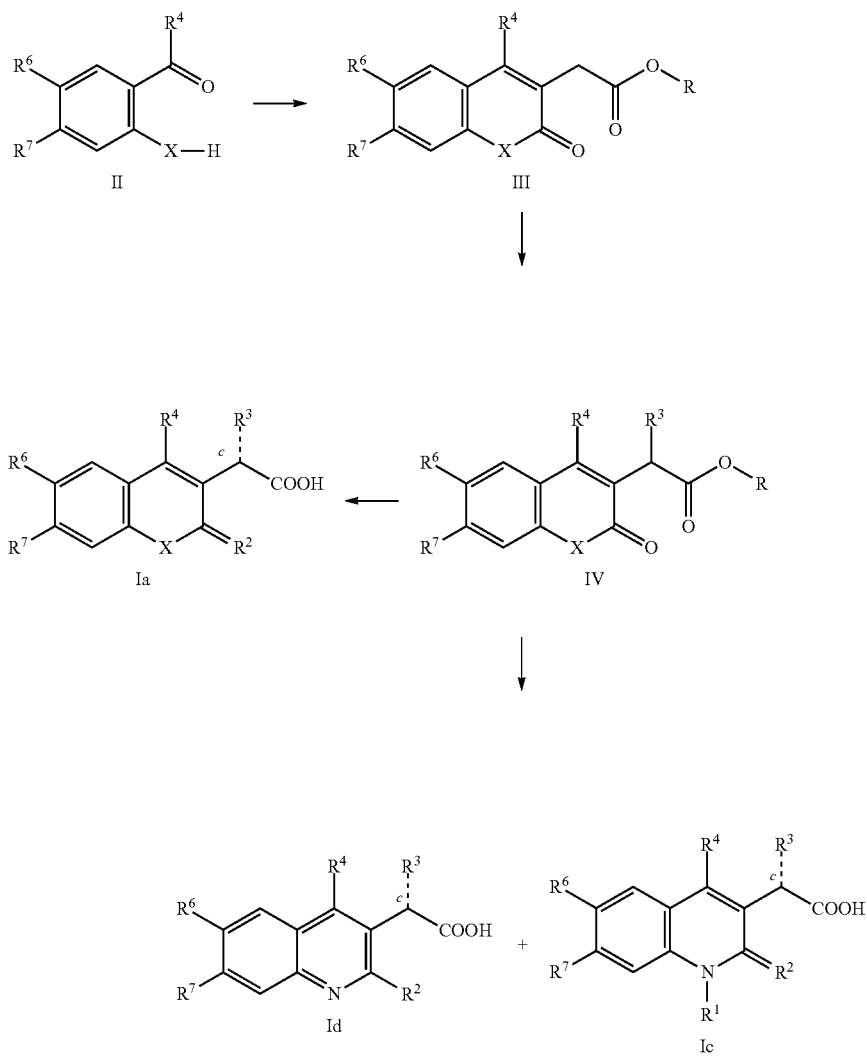

Intermediates of formula (II), wherein X is O or NH and $R^4$, $R^6$ and $R^7$ are as defined herein, are commercially available or are prepared by procedures known to the skilled in the art or as set forth in the examples below. Condensation with an appropriate derivative of succinic acid, by procedures known to the skilled in the art or as set forth in the examples below, provides intermediates of formula (III) wherein R is an ester protecting group such as methyl or ethyl. Alkylation of intermediates (III), by procedures known to the skilled in the art or as set forth in the examples below, provides intermediates of formula (IV), wherein $R^3$ is an optionally substituted alkyl, alkenyl or alkynyl group as defined herein, including a haloalkyl, cycloalkyl-alkyl, aryl-alkyl or Het-alkyl group. It is contemplated that one $R^3$ group may be transformed to another $R^3$ group by procedures well known in the art or as set forth in the examples below, at any chemically convenient intermediate stage in the scheme. Hydrolysis of the ester protecting group of intermediates (IV) provides compounds of formula (Ia) wherein X is O or $NR^1$, $R^2$ is O, bond c is a single bond, $R^3$ is an optionally substituted alkyl, alkenyl or alkynyl group as defined herein, including a haloalkyl, cycloalkyl-alkyl, aryl-alkyl or Het-alkyl group, and $R^1$, $R^4$, $R^6$ and $R^7$ are as defined herein.

Intermediates of formula (IV) wherein X is NH may also be transformed to compounds of formula (Id) wherein bond c is a single bond, $R^2$ is —O$(C_{1-6})$alkyl and $R^3$, $R^4$, $R^6$ and $R^7$ are as defined herein and/or to compounds of formula (Ic) wherein bond c is a single bond, $R^2$ is O and $R^1$, $R^3$, $R^4$, $R^6$ and $R^7$ are as defined herein by alkylation procedures known to the skilled in the art or as set forth in the examples below, followed by hydrolysis of the ester protecting group.

Compounds of formula (Id) wherein bond c is a single bond, $R^2$ is H or $(C_{1-6})$alkyl and $R^3$, $R^4$, $R^6$ and $R^7$ are as defined herein may be prepared as outlined in Scheme 2 below.

Scheme 2:

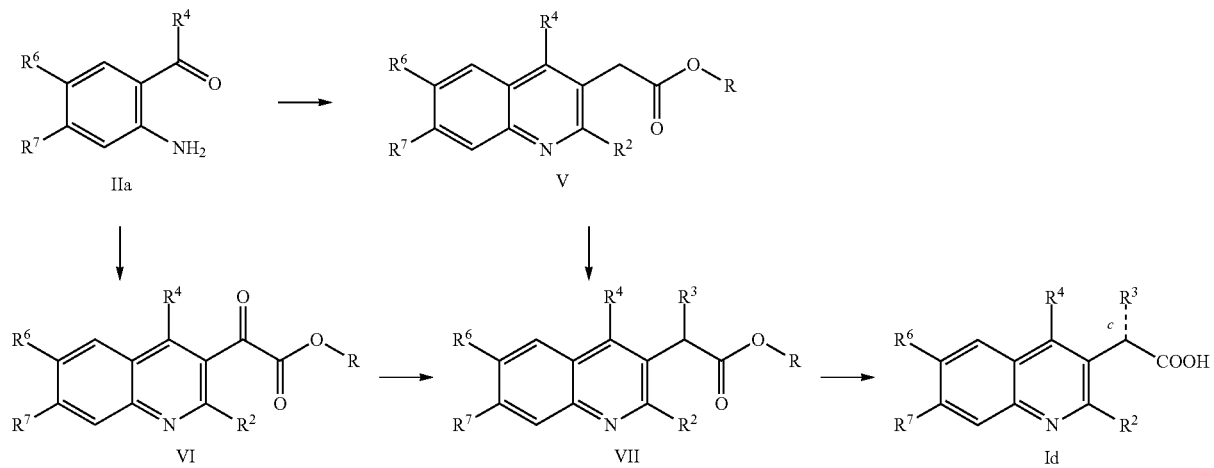

Intermediates of formula (IIa) wherein $R^4$, $R^6$ and $R^7$ are as defined herein, are commercially available or are prepared by procedures known to the skilled in the art or as set forth in the examples below. Condensation of intermediates (IIa) with an appropriate γ-ketoester reagent, by procedures known to the skilled in the art or as set forth in the examples below, provides intermediates of formula (V) wherein R is an ester protecting group such as methyl or ethyl and $R^2$ is H or $(C_{1-6})$alkyl. Alkylation of intermediates (V), by procedures known to the skilled in the art or as set forth in the examples below, provides intermediates of formula (VII), wherein $R^3$ is an optionally substituted alkyl, alkenyl or alkynyl group as defined herein, including a haloalkyl, cycloalkyl-alkyl, aryl-alkyl or Het-alkyl group. Alternatively, intermediates (IIa) are condensed with a suitable α,γ-diketoester reagent, by procedures known to the skilled in the art or as set forth in the $R^3$ is $(C_{1-6})$alkylidene or a group of formula —O—$R^{31}$ wherein $R^{31}$ is as defined herein. It is contemplated that one $R^3$ group may be transformed to another $R^3$ group by procedures well known in the art or as set forth in the examples below, at any chemically convenient intermediate stage in the scheme. Hydrolysis of the ester protecting group of intermediate (VII), by procedures known to the skilled in the art or as set forth in the examples below, provides compounds of formula (Id) wherein bond c is a single bond, $R^2$ is H or $(C_{1-6})$alkyl and $R^3$, $R^4$, $R^6$ and $R^7$ are as defined herein.

Alternatively, compounds of formula (Id) wherein bond c is a single bond, $R^2$ is H or $(C_{1-6})$alkyl, $R^3$ is —O—$R^{31}$ or is an optionally substituted alkyl, alkenyl or alkynyl group as defined herein, including a haloalkyl, cycloalkyl-alkyl, aryl-alkyl or Het-alkyl group, and $R^{31}$, $R^4$, $R^6$ and $R^7$ are as defined herein may be prepared as outlined in Scheme 3 below.

Scheme 3:

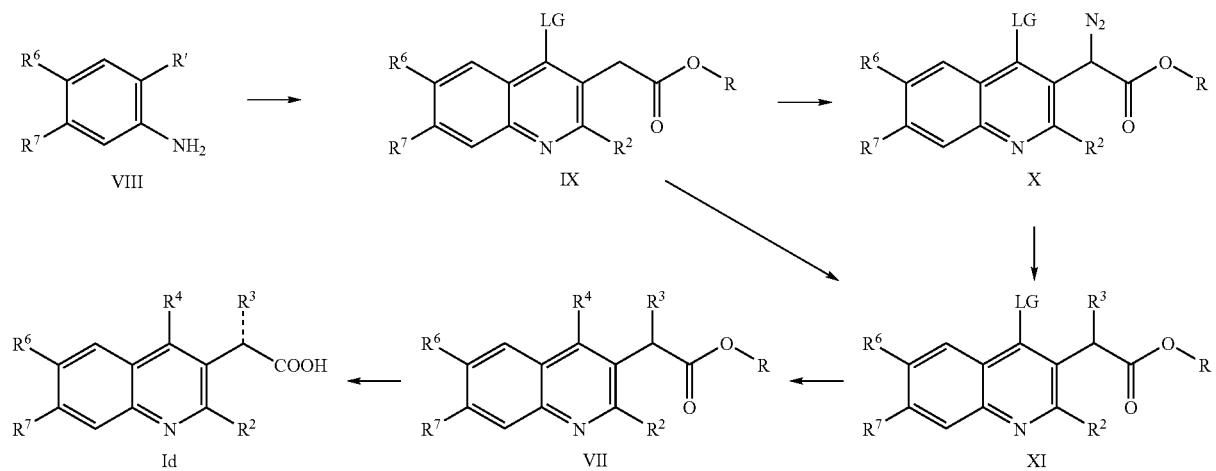

examples below, to provide intermediates of formula (VI), wherein R is an ester protecting group such as methyl or ethyl and $R^2$ is H or $(C_{1-6})$alkyl. Intermediates (VI) are transformed, by procedures known to the skilled in the art or as set forth in the examples below, to intermediates (VII), wherein Intermediates of formula (VIII) wherein R' is COOH or H and $R^6$ and $R^7$ are as defined herein are commercially available or are prepared by procedures known to the skilled in the art or as set forth in the examples below. Intermediates of formula (IX) wherein LG is a leaving group such as a halogen atom, R is an ester protecting group such as methyl or ethyl and $R^2$ is H or $(C_{1-6})$alkyl, are prepared from intermediates of formula (VIII) by procedures known to the skilled in the art or as set forth in the examples below. Intermediates (IX) are transformed to intermediates of formula (X) by reaction with a diazotizing reagent such as 4-acetamidobenzenesulfonyl azide, by procedures known to the skilled in the art or as set forth in the examples below. Displacement of the diazo group with an alcohol, by procedures known to the skilled in the art or as set forth in the examples below, provides intermediates of formula (XI) wherein $R^3$ is —O—$R^{31}$ wherein $R^{31}$ is as defined herein. Alternatively, intermediates (IX) may be converted to intermediates (XI) wherein $R^3$ is an optionally substituted alkyl, alkenyl or alkynyl group as defined herein, including a haloalkyl, cycloalkyl-alkyl, aryl-alkyl or Het-alkyl group, by alkylation, using procedures known to the skilled in the art or as set forth in the examples below. Coupling of intermediates (XI) with a suitable $R^4$ precursor by procedures known to the skilled in the art or as set forth in the examples below, provides intermediates of formula (VII) which are hydrolysed to compounds of formula (Id), wherein bond c is a single bond, $R^2$ is H or $(C_{1-6})$alkyl and $R^3$, $R^4$, $R^6$ and $R^7$ are as defined herein, as outlined in Scheme 2.

As described above, when bond c is a single bond, the carbon atom bonded to the —COOH and $R^3$ substituents can exist in two possible stereochemical configurations, as shown in formulas (Ie) and (If) below:

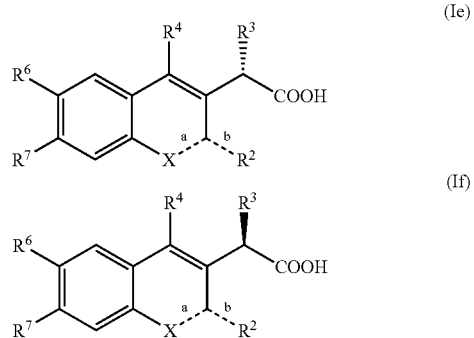

wherein a, b, X, $R^2$, $R^3$, $R^4$, $R^6$ and $R^7$ are as defined herein. Therefore, when the carbon atom to which $R^3$ is bonded is the only stereogenic center in a compound of formula (I), such a compound of formula (I) may exist as enantiomers. When prepared from achiral precursors, the compound of formula (I) will generally exist as a racemic mixture of enantiomers (Ie) and (If). Such a racemic mixture may be separated into its constituent enantiomers by any chiral resolution means known to the skilled in the art, including but not limited to, enzymatic resolution, separation by chiral chromatography, reaction with a chiral auxiliary to form a physically separable mixture of diastereomers, separation of the diastereomers, and removal of the chiral auxiliary to regenerate the separate enantiomers of the compound of formula (I), and other chiral resolution means known in the art or described herein.

EXAMPLES

Other features of the present invention will become apparent from the following non-limiting examples which illustrate, by way of example, the principles of the invention. It will be apparent to a skilled person that the procedures exemplified below may be used, with appropriate modifications, to prepare other compounds of the invention as described herein.

As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Analytical HPLC is carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcOH: acetic acid;
$Ac_2O$: acetic anhydride;
BOC or Boc: tert-butyloxycarbonyl;
Bu: butyl;
DBU: 1,8-diazabicyclo[5.4.0]undec-7-ene;
DCM: dichloromethane;
DME: dimethoxyethane;
DMF: N,N-dimethylformamide;
DMSO: dimethylsulfoxide;
$EC_{50}$: 50% effective concentration;
Et: ethyl;
$Et_3N$: triethylamine;
$Et_2O$: diethyl ether;
EtOAc: ethyl acetate;
EtOH: ethanol;
HPLC: high performance liquid chromatography;
$IC_{50}$: 50% inhibitory concentration;
$^iPr$ or i-Pr: 1-methylethyl (iso-propyl);
LiHMDS: lithium hexamethyldisilazide;
Me: methyl;
MeCN: acetonitrile;
MeOH: methanol;
MOI: multiplicity of infection;
MS: mass spectrometry (MALDI-TOF: Matrix Assisted Laser Desorption Ionization-Time of Flight, FAB: Fast Atom Bombardment);
NMR: nuclear magnetic resonance spectroscopy;
Ph: phenyl;
PG: protecting group;
Pr: propyl;
RPMI: Roswell Park Memorial Institute (cell culture medium);
RT: room temperature (approximately 18° C. to 25° C.);
tert-butyl or t-butyl: 1,1-dimethylethyl;
Tf: trifluoromethanesulfonyl;

Tf$_2$O: trifluoromethanesulfonic anhydride;
TFA: trifluoroacetic acid;
THF: tetrahydrofuran; and
TLC: thin layer chromatography.

Example 1A

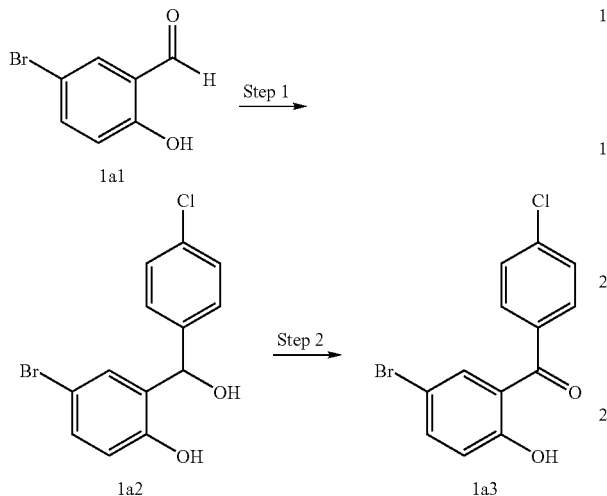

Step 1:
To a solution of aldehyde 1a1 (0.5 g, 2.5 mmol) in Et$_2$O (10 mL) at 0° C., is added 4-chlorophenyl magnesium bromide (5.0 mL, 5.0 mmol) and the mixture is allowed to react at 0° C. for 15 minutes. Saturated aqueous NH$_4$Cl is added, and the mixture is extracted three times with EtOAc. The organic layers are combined, washed with water, saturated aqueous NaHCO$_3$, and brine, dried over MgSO$_4$, filtered and concentrated. The residue is purified by chromatography (hexanes/EtOAc 100:0 to 3:1) to give compound 1a2.

Step 2:
To a solution of alcohol 1a2 (5.82 g, 18.5 mmol) in CH$_2$Cl$_2$ (35 mL) is added activated MnO$_2$ (10.0 g, 115 mmol). The mixture is stirred at room temperature for 18 hours and filtered through Celite™. The filtrate is concentrated under reduced pressure to provide compound 1a3.

Example 1B

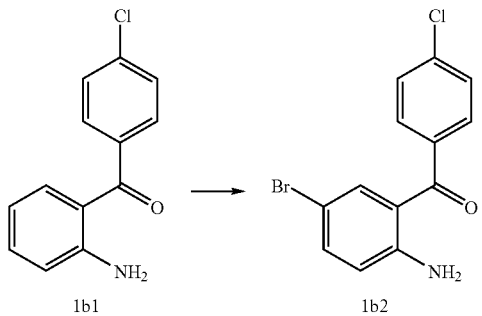

To a solution of compound 1b1 (20.0 g, 86.3 mmol) in AcOH (150 mL) is added KBr (12.3 g, 103.6 mmol) and NaBO$_3$.4H$_2$O (15.9 g, 103.6 mmol) and the mixture is allowed to stir at room temperature for 2 hours. The mixture is poured onto ice and extracted with EtOAc and the organic layer is washed with water and brine, dried (MgSO$_4$), filtered and concentrated. Chromatographic purification of the residue (EtOAc/hexane) provides compound 1b2.

Example 1C

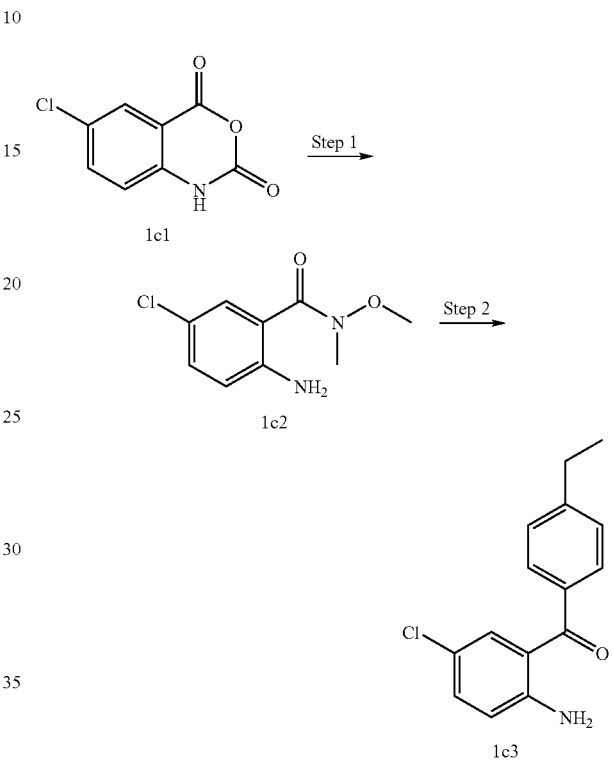

The procedure of S. Frye et al. *J. Org. Chem.* 1991, 56, 3750-3752 is followed.

Step 1:
To a solution of CH$_3$NH—OCH$_3$.HCl (12.35 g, 126.6 mmol) and Et$_3$N (18 mL, 140.2 mmol) in DMF (140 mL) is added compound 1c1 (24.5 g, 124.1 mmol) portionwise. The reaction is stirred at RT for 16 h, then heated at 50° C. for 16 h. The mixture is diluted with EtOAc (300 mL), washed with brine (4×), dried (MgSO$_4$), filtered and evaporated to dryness. The residue is purified by flash column chromatography (50% EtOAc/hexanes) to afford intermediate 1c2.

Step 2:
Compound 1c2 (5.25 g, 24.5 mmol) and 1-ethyl-4-iodobenzene (5.3 mL, 36.7 mmol) are dissolved in anhydrous THF (130 mL) and cooled to −78° C. for 30 min. To this solution is added n-BuLi (1.6M in THF, 38.2 mL, 61.15 mmol) over about 40 min. The reaction is quenched by addition of 10% HCl (aq) and the mixture is extracted with EtOAc. The organic phase is washed with brine, dried over anhydrous MgSO$_4$, filtered and concentrated. The residue is dissolved in EtOAc and purified by flash column chromatography to give compound 1c3.

Other intermediates of formula (II) or (IIa) in Schemes 1 and 2 may be prepared using the procedures of Examples 1A, 1B and 1C.

Example 2A

Preparation of Compounds 3001 and 3002

Table 3

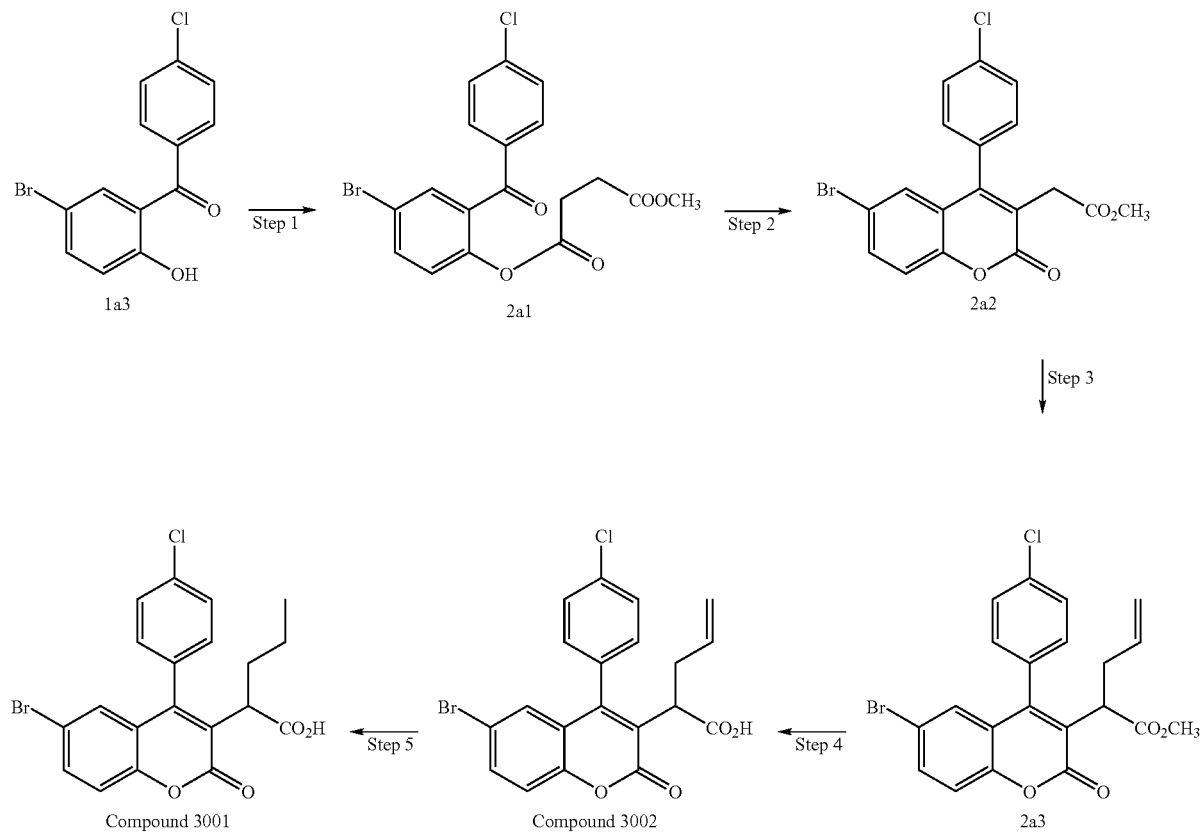

Step 1:

To a mixture of compound 1a3 (Example 1A) (0.72 g, 2.3 mmol) and CH$_2$Cl$_2$, is added pyridine (0.725 mL, 9.0 mmol) and 3-carbomethoxypropionyl chloride (0.36 mL, 2.9 mmol). The mixture is stirred at room temperature for 2 hours, added to 1M HCl and extracted with EtOAc. The organic layer is dried over MgSO$_4$, filtered and evaporated under reduced pressure. The crude product is purified by flash chromatography on silica gel (20% EtOAc/hexanes) to give compound 2a1.

Step 2:

A mixture of compound 2a1 (0.54 g, 1.3 mmol), triethylamine (4.0 mL), and acetic anhydride (6.0 mL) is heated at 100° C. for 18 h. The mixture is added to 1M HCl and brine (1:1 mixture) and extracted with EtOAc. The organic layer is washed with saturated aqueous NaHCO$_3$, dried over MgSO$_4$, filtered and evaporated under reduced pressure. The residue is purified by flash chromatography to give compound 2a2.

Step 3:

To a solution of compound 2a2 (0.18 g, 0.44 mmol) and allyl bromide (0.6 mL, 6.9 mmol) in THF (2.0 mL) at 0° C. is added LiHMDS (0.7 mL, 0.70 mmol). When the reaction is complete by TLC, saturated NH$_4$Cl is added and the mixture is extracted with EtOAc. The combined organic phase is washed with brine, dried over MgSO$_4$, filtered and concentrated. Purification by flash chromatography (Hexane/EtOAc 100:0 to 4:1) gives compound 2a3.

Step 4:

To a mixture of compound 2a3 (0.10 g, 0.22 mmol) and DMSO (2 mL), is added H$_2$O (0.15 mL) and NaOH (10 N, 0.15 mL) and the mixture is heated at 60° C. for 1 hour. The reaction is quenched with saturated NH$_4$Cl and the mixture is extracted with EtOAc. The combined organic layers are washed with brine, dried over MgSO$_4$, filtered and concentrated to give compound 3002 (Table 3).

Step 5:

A mixture of compound 3002 (0.0740 g, 0.17 mmol), EtOAc (2.5 mL) and platinum (IV) oxide (8 mg) is stirred under an atmosphere of H$_2$ for 1 hour. The mixture is filtered through Celite™ and concentrated under reduced pressure. The residue is purified by preparative HPLC to provide compound 3001.

Example 2B

Preparation of Compound 2011

Table 2

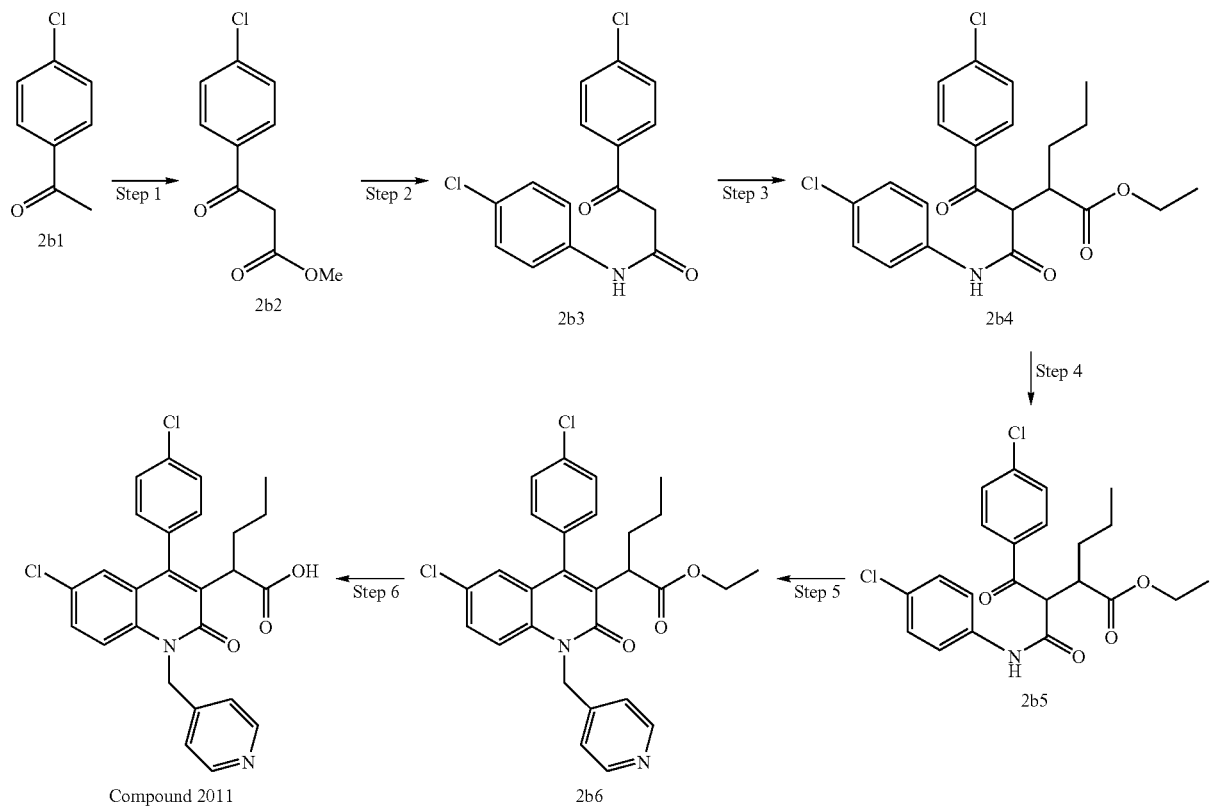

Step 1:

Dimethyl carbonate (22 mL, 269 mmol) and NaH (60% in oil, 10.8 g, 270 mmol) are combined in toluene (80 mL) and heated to 90° C. for 20 minutes, then 4-chloroacetophenone 2b1 (14 mL, 109 mmol) is added dropwise over ca. 15 minutes. The mixture is stirred at 90° C. for 30 minutes, then cooled and carefully treated with 5% HCl (aq) (100 mL) and EtOAc (100 mL). The organic phase is washed with brine, dried (MgSO$_4$), filtered and concentrated to dryness. The residue is purified by flash chromatography (15% EtOAc/hexanes) to give compound 2b2.

Step 2:

A mixture of compound 2b2 (7.1 g, 33.4 mmol) and 4-chloroaniline (5.9 g, 46.3 mmol) in DMF/xylene (7 mL/40 mL) is heated at 140° C. for 10 h. The mixture is partitioned between 1M HCl (40 mL) and EtOAc (150 mL). The organic layer is washed with 1M HCl, water and brine, dried over MgSO$_4$, filtered and concentrated to dryness. The residue is purified by flash chromatography (SiO$_2$, 15% to 20% EtOAc/hexanes) to give compound 2b3.

Step 3:

To a mixture of compound 2b3 (4.79 g; 15.5 mmol), KOtBu (2.0 g; 18.57 mmol) and DMF (23 mL) is added ethyl-2-bromovalerate (3.2 mL, 18.25 mmol). The mixture is allowed to stir at room temperature for 16 h, then is poured over ice into a solution of 1N HCl (100 mL) and the mixture is extracted with EtOAc (2×100 mL). The combined organic extracts are washed with brine (4×), dried (Na$_2$SO$_4$), filtered and concentrated to afford, after purification by chromatography (EtOAc/hexanes) compound 2b4 as a mixture of diastereoisomers.

Step 4:

A mixture of compound 2b4 (in separate portions of 1.26 g, 0.77 g and 1.09 g; 7.15 mmol total) and H$_2$SO$_4$ (in separate portions of 24 mL, 15 mL and 19 mL) is allowed to react at 150° C. for 20 minutes. The combined reaction mixture is allowed to cool slightly and added dropwise to ice-water. The mixture is extracted with EtOAc (3×), washed with brine (1×), dried (Na$_2$SO$_4$), filtered and concentrated in vacuo The residue (0.69 g; 1.76 mmol) is dissolved in EtOH (25 mL) and to this solution is added POCl$_3$ (2.4 mL; 27 mmol). The reaction is heated at reflux for 1 h, then poured into ice-water and extracted with CH$_2$Cl$_2$ (3×). The organic phase is washed with brine, dried (MgSO$_4$), filtered and concentrated and the residue is purified by chromatography to afford compound 2b5.

Step 5:

To a mixture of compound 2b5 (30 mg; 0.072 mmol) and anhydrous MeCN (1.8 mL) is added K$_2$CO$_3$ (150 mg; 1.1 mmol) and 4-bromomethylpyridine (36 mg; 0.14 mmol) and the mixture is heated to 70° C. and allowed to react for 16 h. The mixture is diluted with EtOAc (40 mL), washed with brine, dried (Na$_2$SO$_4$), filtered and concentrated to afford compound 2b6.

Step 6:

Using the procedure of Example 3A, step 4, compound 2b6 is hydrolysed to give compound 2011 (Table 2).

Example 2C

Preparation of Compound 2010

Table 2

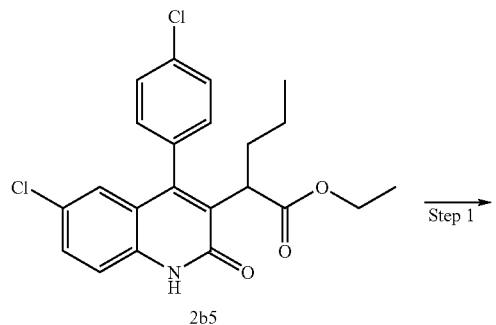

2b5

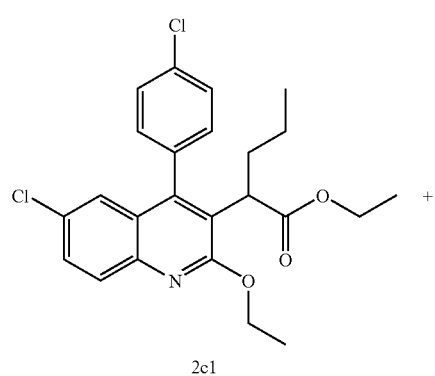

2c1

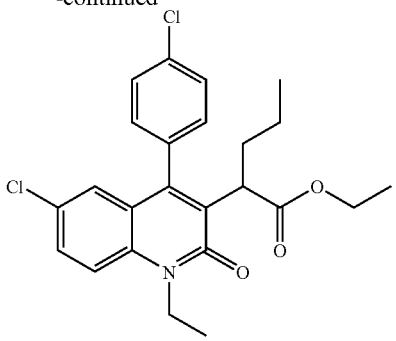

2c2

Step 2

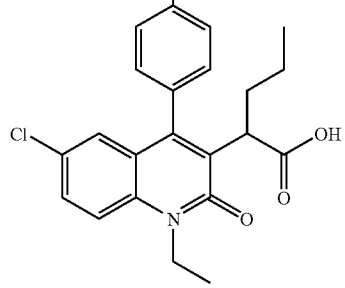

Compound 2010

Step 1:

To a mixture of compound 2b5 (Example 2B) (20 mg; 0.05 mmol), anhydrous MeCN (1.2 mL) and $K_2CO_3$ (15 mg; 0.1 mmol) is added ethyl iodide (40 μL; 0.5 mmol). The mixture is allowed to react at 70° C. for 16 h, then is diluted with EtOAc (40 mL), washed with brine, dried ($Na_2SO_4$), filtered and concentrated to provide a mixture of compounds 2c1 and 2c2.

Step 2:

The mixture of compounds 2c1 and 2c2 is saponified as described in Example 3A, step 4. Purification of the mixture by preparative HPLC provides compound 2010 (Table 2).

Example 3A

Preparation of Compound 1058

Table 1

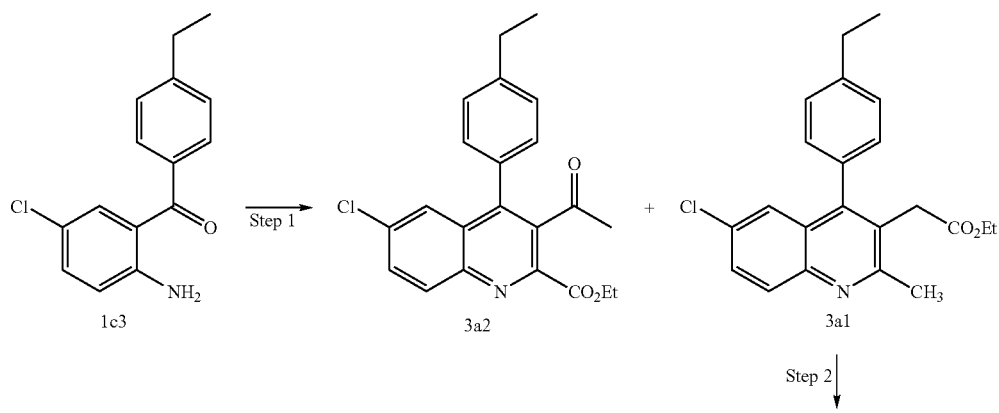

Step 2

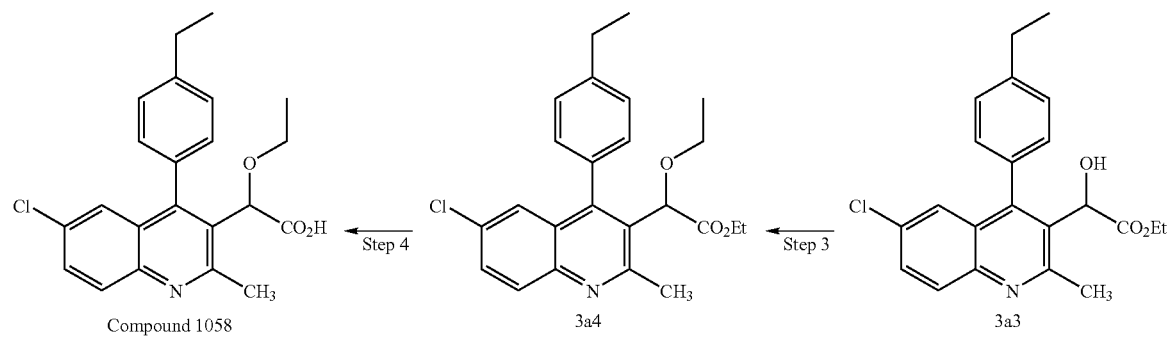

Step 1:

To a solution of compound 1c3 (Example 1C) (3.69 g, 14.17 mmol) in AcOH (88 mL) is added ethyl acetopyruvate (2.65 mL, 18.4 mmol) followed by conc. $H_2SO_4$ (438 µL). The resulting mixture is heated to 50° C. for 16 h, allowed to cool to RT, then concentrated under reduced pressure and the residue partitioned between EtOAc and water. Solid $NaHCO_3$ is carefully added with stirring and the organic phase is washed with brine, dried over anhydrous $MgSO_4$, filtered and concentrated. The residue is purified by flash column chromatography (20% EtOAc/hexane) to provide compound 3a1 (less polar) and by-product 3a2 (more polar).

Step 2:

To a mixture of compound 3a1 (2.39 g, 6.26 mmol) and THF/EtOH (40 mL/10 mL) cooled to 0° C. is added $NaBH_4$ (213 mg, 5.63 mmol) over a period of 1 min. The mixture is stirred at 0° C. for 40 minutes and diluted with water and 10% aqueous HCl. The mixture is extracted with EtOAc and the organic extract is washed with brine, dried over anhydrous $MgSO_4$, filtered and concentrated to give the alcohol 3a3.

Step 3:

A solution of compound 3a3 (513 mg, 1.34 mmol) in anhydrous DMF (10 mL) is treated dropwise with LiHMDS (1M in THF, 1.56 mL, 1.56 mmol) over a 1 minute period. Iodoethane (0.60 mL, 7.5 mmol) is added and the reaction mixture is allowed to stir at RT under an $N_2$ atmosphere for 30 min. The reaction is quenched with water and the mixture partitioned between water and EtOAc. The organic phase is washed with brine, dried ($MgSO_4$), filtered and concentrated to give intermediate 3a4.

Step 4:

A mixture of compound 3a4 (530 mg, 1.29 mmol), MeOH/THF (6 mL/6 mL) and 1N NaOH (0.77 mL, 7.72 mmol) is allowed to react for 30 minutes. The mixture is partitioned between water and EtOAc and the aqueous phase is acidified to pH ~5-6 and extracted with EtOAc. The combined organic phase is dried ($MgSO_4$), filtered and concentrated to give compound 1058 (Table 1).

Example 3B

Preparation of Compound 1061

Table 1

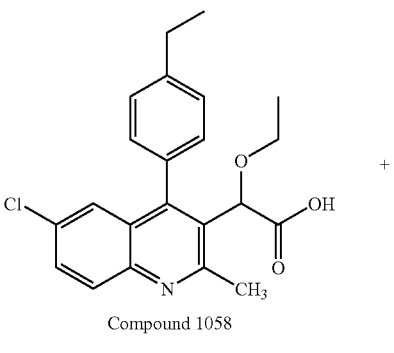

Compound 1058

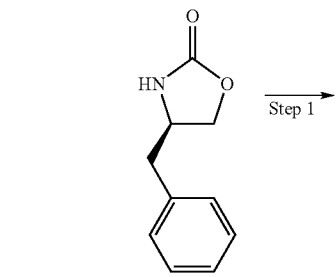

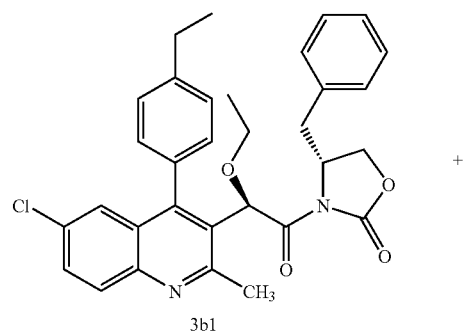

3b1

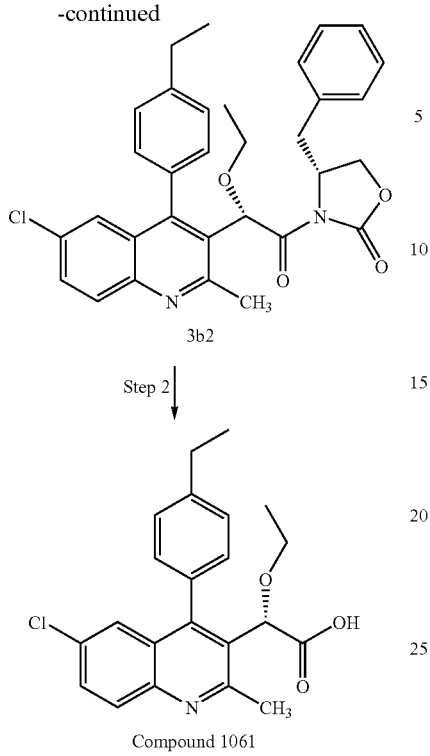

3b2

Step 2 ↓

Compound 1061

Step 1:

To a stirred solution of compound 1058 (Example 3A) (230 mg, 0.60 mmol) in anhydrous THF (15 mL) at 0° C. is added Et$_3$N (125 μL, 0.90 mmol) followed by pivaloyl chloride (85 μL, 0.69 mmol). The resulting solution is stirred at 0° C. for 30 min and then at RT for 1.5 h. The mixture is cooled to −78° C. for 30 minutes, and to it is added a mixture formed by treating a solution of (R)-(+)-4-benzyl-2-oxazolidinone (127 mg, 0.72 mmol) in anhydrous THF (5 mL), cooled to −78° C., with a solution of n-BuLi in hexanes (1.6 M, 487 μL, 0.78 mmol) and stirring the resulting mixture at −78° C. for 30 min. The mixture is allowed to warm slowly to RT and stirred for 2 h. Saturated NH$_4$Cl (30 mL) is added and the mixture is extracted twice with EtOAc. The combined organic extracts are washed with brine, dried (MgSO$_4$), filtered and concentrated, and the residue is purified by flash column chromatography (5-45% EtOAc in hexanes) to separate the more polar adduct 3b2 from its diastereomer 3b1.

Step 2:

To a solution of compound 3b2 (110 mg, 0.20 mmol) in THF/water (2 mL/1 mL) at 0° C. is added H$_2$O$_2$ (62 μL, 0.61 mmol) followed by dropwise addition of LiOH.H$_2$O (12.2 mg in 0.2 mL of H$_2$O). The mixture is stirred at 0° C. for 30 min, then 10% Na$_2$SO$_3$ (2 mL) is added and the mixture is partitioned between EtOAc and water (adjusted pH to 10). The aqueous phase is adjusted to pH 4-5 and extracted three times with EtOAc. The organic phase is dried (MgSO$_4$), filtered and concentrated, and the residue is dissolved in DMSO and purified by preparative HPLC to give compound 1061 (Table 1) with optical purity of 99.7% enantiomeric excess as determined by chiral HPLC (ChiralCel OD-R column; 4.6×250 mm, 10 μm).

The procedure of Example 3B may be used to resolve racemic mixtures of other compounds of formula (I) bearing a chiral center into their constituent enantiomers.

Example 3C

Preparation of Compound 1078

Table 1

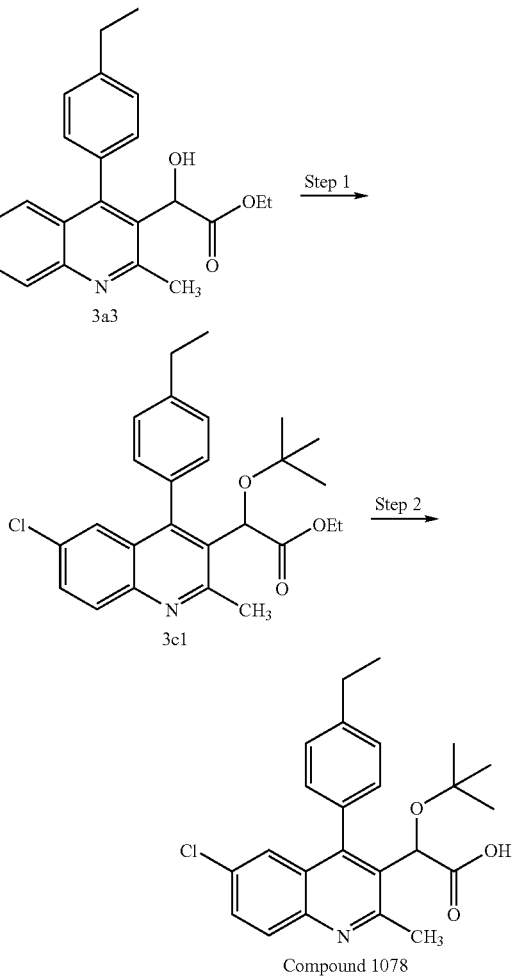

Step 1:

A mixture of compound 3a3 (Example 3A) (2.9 g, 7.55 mmol), anhydrous dioxane (40 mL), isobutylene gas (approx. 10 mL condensed at 0° C.) and BF$_3$-Et$_2$O (8 mL, 61 mmol) at 0° C. is allowed to stir at room temperature in a Teflon™ sealed tube for 16 h. Additional isobutylene is added at 0° C. (approx. 5 mL) and stirring is continued at room temperature for 3 h. Further BF$_3$-Et$_2$O (2 mL) and isobutylene (5 mL) is added at 0° C. and stirring is continued at room temperature for 16 h. Saturated aqueous NaHCO$_3$ (10 mL) is added to the reaction mixture, followed by solid NaHCO$_3$ and water, the mixture is stirred for 30 min, and the phases are separated. The aqueous phase is extracted (EtOAc) and the combined organic phase is dried over MgSO$_4$, filtered and concentrated. The residue is purified by flash column chromatography (gradient of 10% to 60% EtOAc/hexanes) to give compound 3c1.

Step 2:
The procedure used in Example 3A, Step 4 is followed.

Example 4A

Preparation of Compound 1035

Table 1

Step 3:
To a solution of compound 4a2 (0.080 g, 0.20 mmol) in THF (5.0 mL) at 0° C. is added 3-bromo-2-methylpropene (0.3 mL, 3.0 mmol), followed by LiHMDS (0.5 mL, 0.50 mmol) and the reaction mixture is allowed to stir at RT until reaction is complete. Aqueous NH$_4$Cl is added and the mixture is extracted with EtOAc. The organic layers are combined, washed with brine, dried over MgSO$_4$, filtered and concentrated to provide compound 4a3.

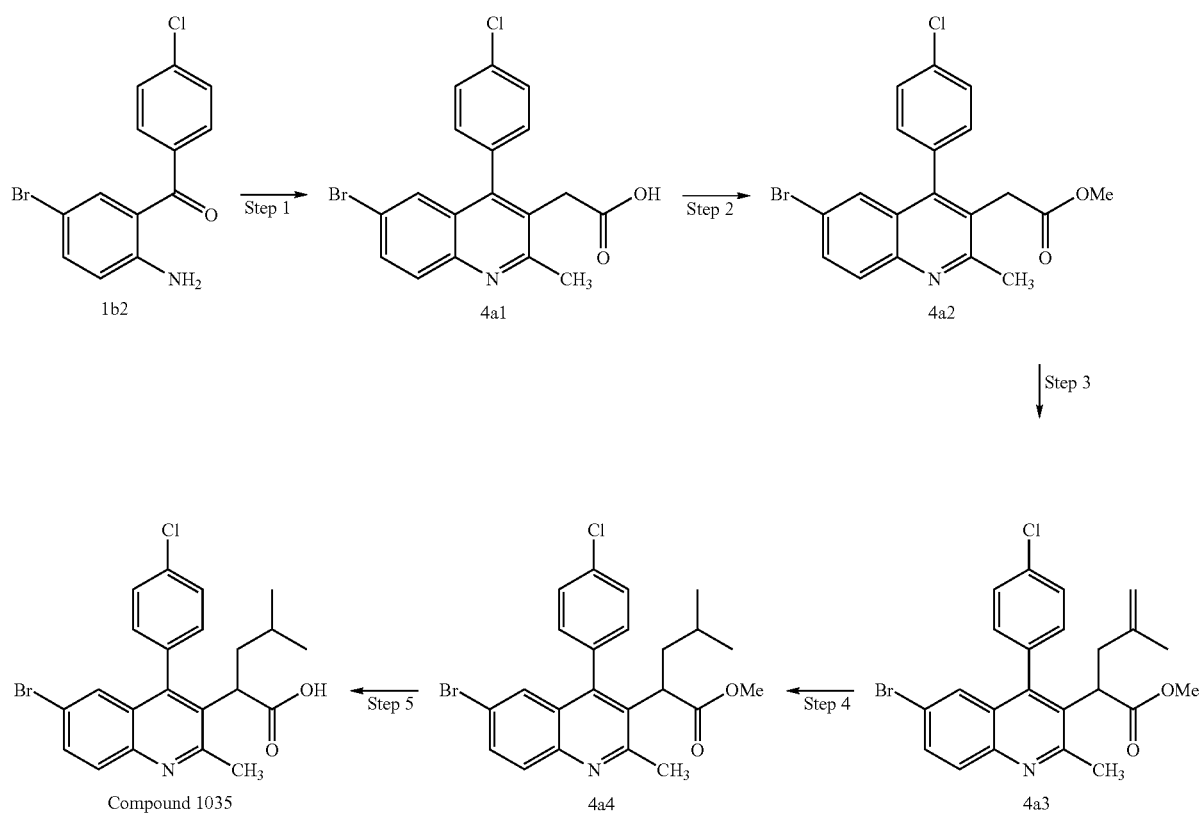

Step 1:
A mixture of compound 1b2 (Example 1B) (3.0 g, 9.66 mmol), levulinic acid (1.4 mL, 13.5 mmol), concentrated H$_2$SO$_4$ (0.39 mL) and AcOH (30 µL) is heated at 130° C. for 17 h. The mixture is added to H$_2$O (50 mL) and the pH is adjusted to 4 by addition of 1M NaOH. The aqueous phase is extracted with EtOAc and n-butanol and the organic extract is washed with water and brine, dried (MgSO$_4$), filtered and concentrated. The residue is triturated with a mixture of Et$_2$O and EtOAc to provide compound 4a1.

Step 2:
To a mixture of compound 4a1 (1.5 g, 3.84 mmol) in toluene/MeOH (2:1, 30 mL) is added trimethylsilyldiazomethane (2M, 3.0 mL, 6.0 mmol). Concentration of the mixture under reduced pressure provides compound 4a2.

Step 4:
A mixture of compound 4a3 (0.0910 g, 0.20 mmol), EtOAc/MeOH (9:1, 10 mL), and Pt$_2$O (Adam's catalyst) (10 mg) is allowed to stir at room temperature under an atmosphere of H$_2$ for 30 min. N$_2$ gas is passed through the mixture, which is then filtered through Celite™ and concentrated. Purification of the residue by flash chromatography provides compound 4a4.

Step 5:
A mixture of compound 4a4 (0.047 g, 0.102 mmol), DMSO (1.0 mL), water (0.1 mL) and NaOH (10N, 0.1 mL) is stirred at 65° C. for 1 hour. AcOH (0.15 mL) is added and the mixture is purified by preparative HPLC to provide compound 1035 (Table 1).

Example 4B

Preparation of Compound 1101

Table 1

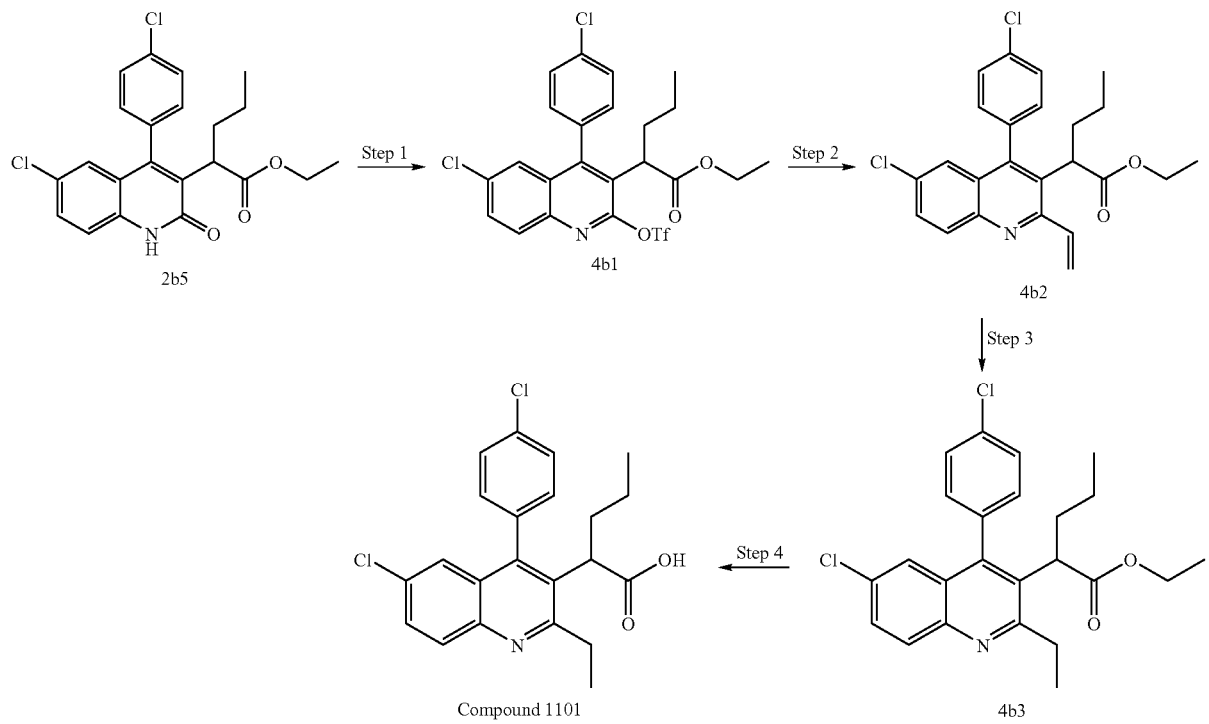

Step 1:

To a mixture of compound 2b5 (Example 2B) (238 mg; 0.56 mmol), anhydrous $CH_2Cl_2$ (4 mL) and pyridine (276 μl; 3.4 mmol) at 0° C. is added $Tf_2O$ (191 μl; 1.13 mmol). The mixture is stirred at 0° C. for 30 min, warmed to room temperature and stirred for 20 h. The mixture is poured into ice-water and extracted with $CH_2Cl_2$ (3×). The organic layer is washed with brine, dried ($MgSO_4$), filtered and concentrated to dryness. The residue is purified by chromatography to afford compound 4b1.

Step 2:

To a solution of compound 4b1 (50 mg; 0.091 mmol) and $Pd[P(t-Bu)_3]_2$ (5 mg; 10 mol %) in DMF (1 mL) is added tri-n-butylvinyltin (37 μl; 0.127 mmol). The mixture is sealed and allowed to react under microwave conditions at 110° C. for 20 min. The mixture is poured into EtOAc (50 mL), washed with brine (1×), $NaHCO_3$ and brine (3×). The organic phase is dried ($Na_2SO_4$), filtered and concentrated and the residue is purified by flash chromatography (1:30 silica gel; 9:1 Hexane/EtOAc) to afford compound 4b2.

Step 3:

A mixture of compound 4b2 (27 mg; 0.063 mmol), EtOH (1.5 mL) and $PtO_2$ (4 mg) is allowed to react under $H_2$ at 1 atm for 20 min. The mixture is filtered through Celite™, and the Celite™ pad is washed with EtOH. The combined filtrate is concentrated under reduced pressure to afford compound 4b3.

Step 4:

Using the procedure described in Example 3A, step 4, compound 4b3 is converted to compound 1101 (Table 1).

Example 5A

Preparation of Compound 1034

Table 1

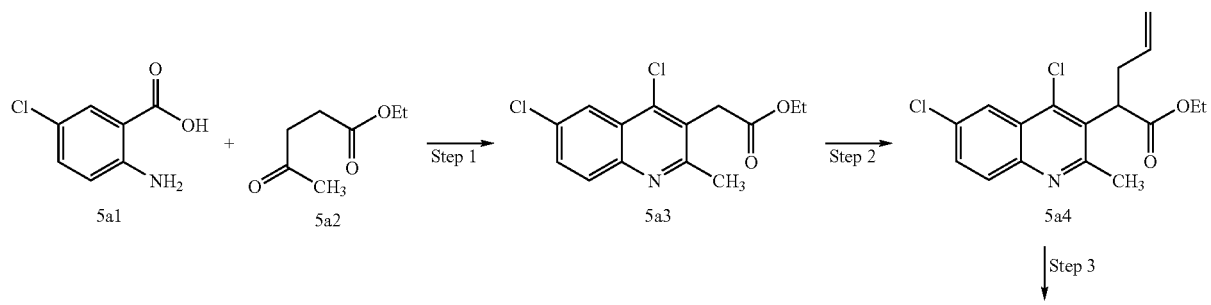

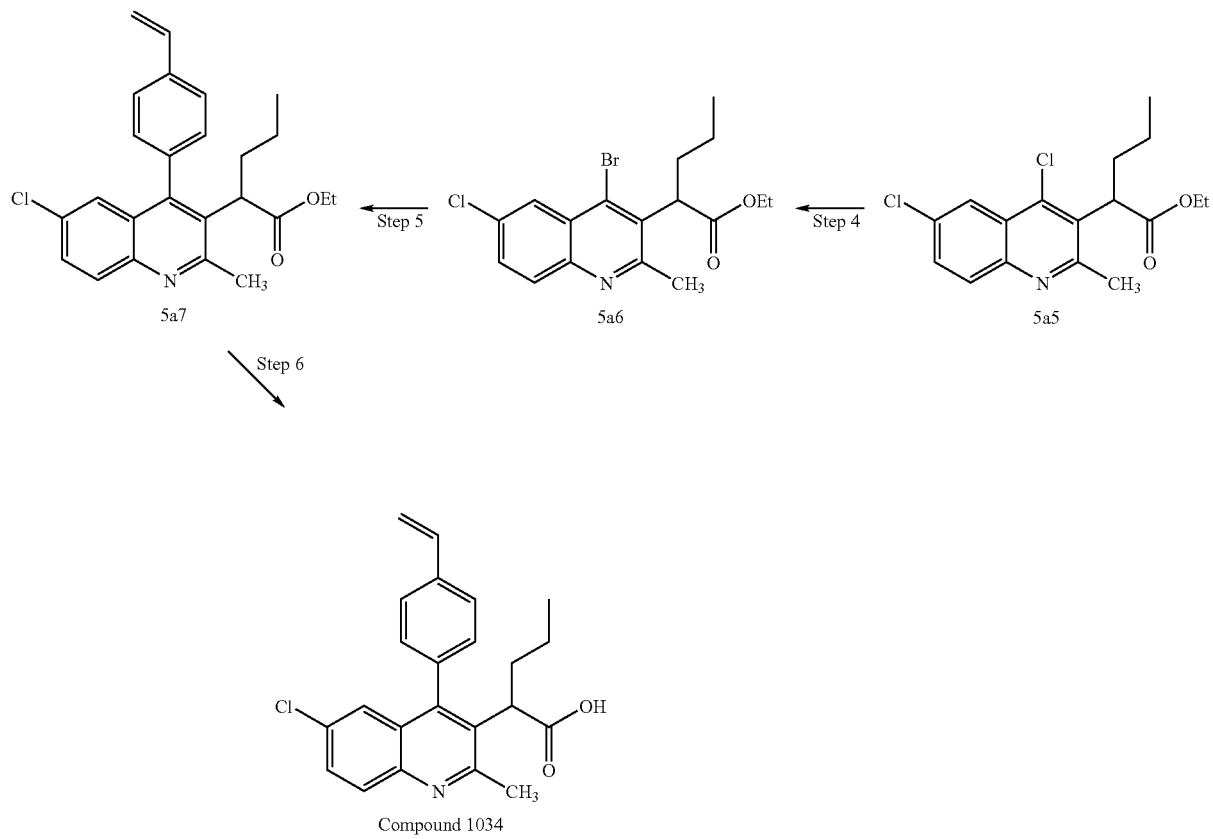

Step 1:

To a mixture of acid 5a1 (3.2 g, 18.7 mmol) and ethyl levulinate 5a2 (2.7 mL, 19.0 mmol) in THF (25 mL) is added MgSO$_4$ (6.5 g). The mixture is heated at 65° C. for 1 hour, filtered and concentrated under reduced pressure. The residue is mixed with POCl$_3$ (12 mL) and heated at reflux for 4 hours. The reaction mixture is concentrated and the residue is treated with ice and solid NaHCO$_3$ to adjust the pH to 7-8. The mixture is filtered and the collected solid is taken up in EtOAc, washed with water, dried over MgSO$_4$, filtered, concentrated and purified by flash chromatography (100% Hexane to 1:1 Hex/EtOAc) to provide compound 5a3.

Step 2:

To a mixture of ester 5a3 (0.0761 g, 0.26 mmol), THF (3.0 mL) at 0° C. and allyl bromide (0.2 mL, 2.3 mmol) is added LiHMDS (0.4 mL, 1.0 M, 0.4 mmol). The mixture is allowed to stir at RT for 30 minutes, then aqueous NH$_4$Cl is added, and the mixture is extracted with EtOAc. The combined organic layers are washed with brine, dried over MgSO$_4$, filtered and concentrated to provide compound 5a4.

Step 3:

Compound 5a4 is hydrogenated using the procedure of Example 4A, Step 4, to provide compound 5a5.

Step 4:

To a solution of compound 5a5 (0.1466 g, 1.5 mmol) in CH$_3$CH$_2$CN (5 mL), is added (CH$_3$)$_3$SiBr (15 mL, 4.6 mmol) and the mixture is stirred at 75° C. overnight, with removal of (CH$_3$)$_3$SiCl by distillation. Saturated NaHCO$_3$ is added and the mixture is extracted with EtOAc. The combined organic layers are washed with brine, dried over MgSO$_4$, filtered and concentrated to give compound 5a6.

Step 5:

A mixture of compound 5a6 (20.7 mg, 0.054 mmol), 4-ethenylphenylboronic acid (10 mg, 0.068 mmol) and DMF (2.0 mL) is purged with Ar, and to this mixture is added Pd(PPh$_3$)$_4$ (3.0 mg, 0.003 mmol). The reaction mixture is allowed to react at 120° C. for 2.5 hours, then at RT overnight. The mixture is partitioned between EtOAc and H$_2$O and the organic phase is washed with brine, dried (MgSO$_4$) and concentrated. The residue is purified by flash chromatography (20-30% EtOAc/hexane) to give compound 5a7.

Step 6:

A mixture of compound 5a7 (21.4 mg, 0.052 mmol), DMSO (1.0 mL), and NaOH (5N, 52 μL) is stirred at 60° C. for 45 minutes. CF$_3$COOH is added and the mixture is purified by preparative HPLC to provide compound 1034 (Table 1).

Example 5B

Preparation of Compound 1093

Table 1

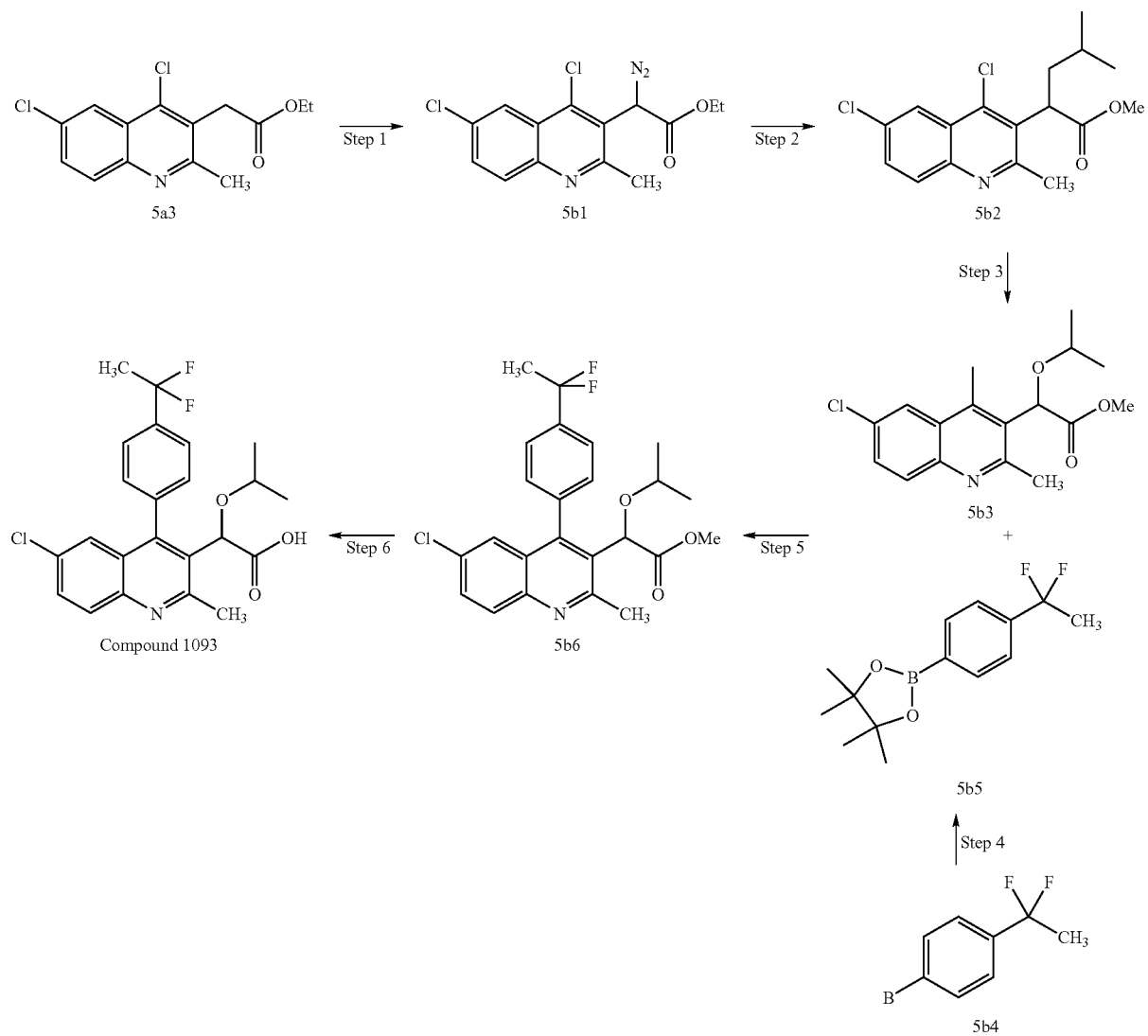

Step 1:

The procedure of Hahn et al (*J. Organometal. Chem.* (2004) 689(16): 2662-73) is followed.

To a mixture of compound 5a3 (Example 5A) (200 mg, 0.671 mmol) and 4-acetamidobenzenesulfonyl azide (322 mg, 1.34 mmol) in anhydrous MeCN (9 mL) at RT is added DBU (501 µL, 3.35 mmol). The mixture is stirred at room temperature for 3 hours, then brine (0.5 mL) is added and the mixture is partitioned between brine and EtOAc. The combined organic phases are dried over MgSO$_4$, filtered and concentrated under reduced pressure. The residue is purified by column chromatography (20% ethyl acetate/hexane) to provide compound 5b1.

Step 2:

A mixture of compound 5b1 (200 mg, 0.617 mmol), 2-propanol (7.7 mL, 100 mmol) and rhodium(II) acetate dimer (81.8 mg, 0.185 mmol) is allowed to react in a Biotage Initiator™ Sixty microwave apparatus at 160° C. for 10 minutes. To the mixture is added THF (5.0 mL), MeOH (1.25 mL) and LiOH (1N, 1.5 mL, 1.5 mmol) and the mixture is allowed to stir overnight at room temperature. After acidification with 1N HCl, the mixture is extracted with EtOAc and the organic extract is dried (MgSO$_4$), filtered and concentrated. The residue is dissolved in THF (10 mL) and treated with diazomethane. Concentration of the mixture and purification of the residue by flash chromatography (EtOAc/hexane) provides compound 5b2.

Step 3:

The procedure of Wolf et al (*Synlett* (2003) (12): 1801-4) is followed.

A mixture of compound 5b2 (132 mg, 0.386 mmol), THF (1.5 mL) and HCl/dioxane (4M, 0.964 mL, 3.86 mmol) is allowed to stir at room temperature for 10 minutes. The mixture is concentrated under reduced pressure, the residue is suspended in CH$_3$CN (3.0 mL), and to this mixture is added NaI (0.405 g, 2.7 mmol). The mixture is heated at reflux for 2 days, diluted with EtOAc, washed with water and 0.5N Na$_2$S$_2$O$_3$, dried (MgSO$_4$), filtered and concentrated under reduced pressure. Purification of the residue by flash chromatography (20% EtOAc/hexane) provides compound 5b3.

Step 4:

To a mixture of compound 5b4 (210 mg, 0.95 mmol) in DMF (6.0 mL) is added bis(pinacolato)diboron (265 mg, 1.045 mmol) and KOAc (205 mg, 2.09 mmol). Argon is passed through the mixture for 5 minutes and PdCl₂(dppf)-CH₂Cl₂ (77.6 mg, 0.095 mmol) is added. Argon is passed through the mixture for 3 minutes further and the mixture is allowed to react at 80° C. overnight. The mixture is extracted with EtOAc and the extract is washed with brine, dried (MgSO₄), filtered through Celite™ and concentrated to provide boronic acid 5b5.

Step 5:

A mixture of compound 5b3 (90 mg, 0.208 mmol), compound 5b5 (111.3 mg, 0.415 mmol), K₂CO₃ (86 mg, 0.623 mmol), Pd(PPh₃)₄ (24.0 mg, 0.021 mmol) and DMF (6.0 mL) is allowed to react in a Biotage Initiator™ Sixty microwave apparatus at 120° C. for two periods of 5 minutes each. The reaction mixture is diluted with EtOAc, washed with brine, dried (MgSO₄), filtered and concentrated. The residue is purified by flash chromatography to provide compound 5b6.

Step 6:

A mixture of compound 5b6 (35 mg, 0.078 mmol), LiOH (1N, 0.234 mL, 0.234 mmol), MeOH (125 mg) and THF (1.27 mL) is allowed to react at 40° C. for 2 h. The mixture is acidified with TFA and purified by preparative HPLC to provide compound 1093.

Example 5C

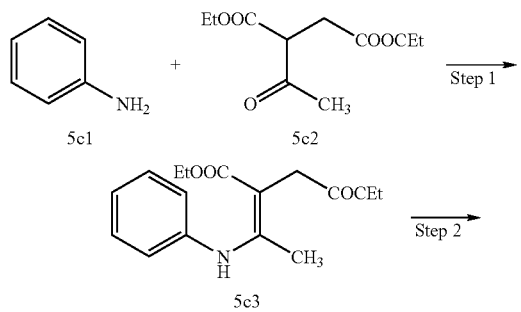

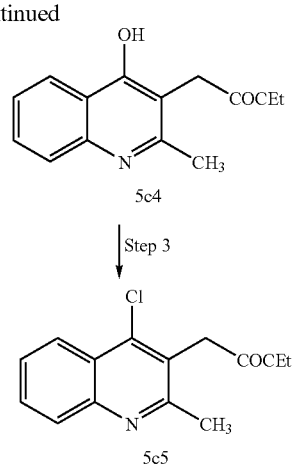

Step 1:

A mixture of aniline 5c1 (68 mL, 0.75 mol) and diethyl acetylsuccinate 5c2 (149.2 mL, 0.75 mol) is allowed to stir at room temperature for 2 days in a sealed dessicator under vacuum in the presence of P₂O₅. The reaction mixture is diluted with CH₂Cl₂ and purified by flash chromatography (EtOAc/hexane gradient 1:8 to 1:6) to provide compound 5c3.

Step 2:

A mixture of compound 5c3 (19.85 g, 68.1 mmol) and Ph₂O (100 mL) is heated at 250° C. for 10 min, then allowed to cool to room temperature. Hexane is added to the mixture and the solid which forms is collected by filtration, washed with hexane and dried to provide compound 5c4.

Step 3:

A mixture of compound 5c4 (15.8 g, 64.0 mmol) and POCl₃ (50 mL) is heated at reflux under Ar atmosphere for 4 h. The mixture is cooled and concentrated under reduced pressure and the residue is treated with powdered NaHCO₃ and diluted with EtOAc. The organic phase is washed with saturated NaHCO₃, water and brine, dried (Na₂SO₄), and filtered through a pad of silica gel. Concentration of the filtrate under reduced pressure provides compound 5c5.

Compound 5c5 can be transformed to compounds of formula (Id) wherein $R^6$ is H and $R^2$ is CH₃, using the procedures of Examples 5A (steps 2-6) and 5B.

Example 6A

Preparation of Compound 1009

Table 1

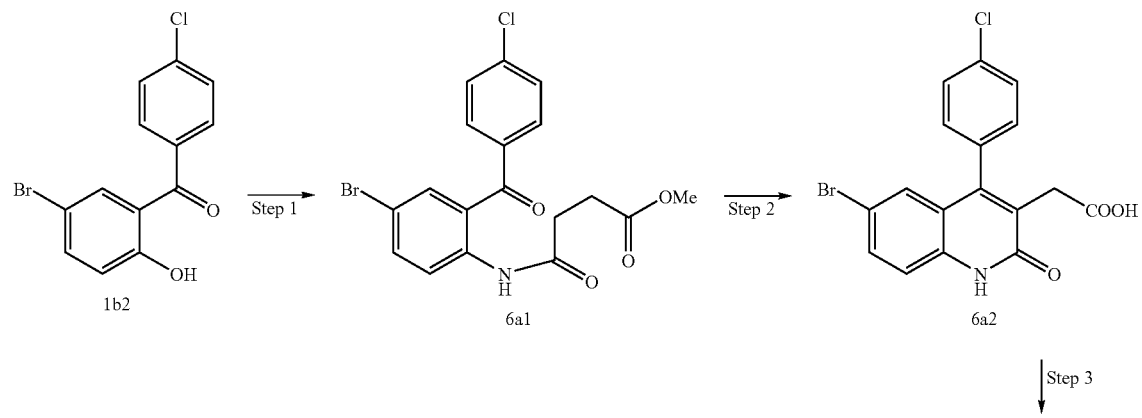

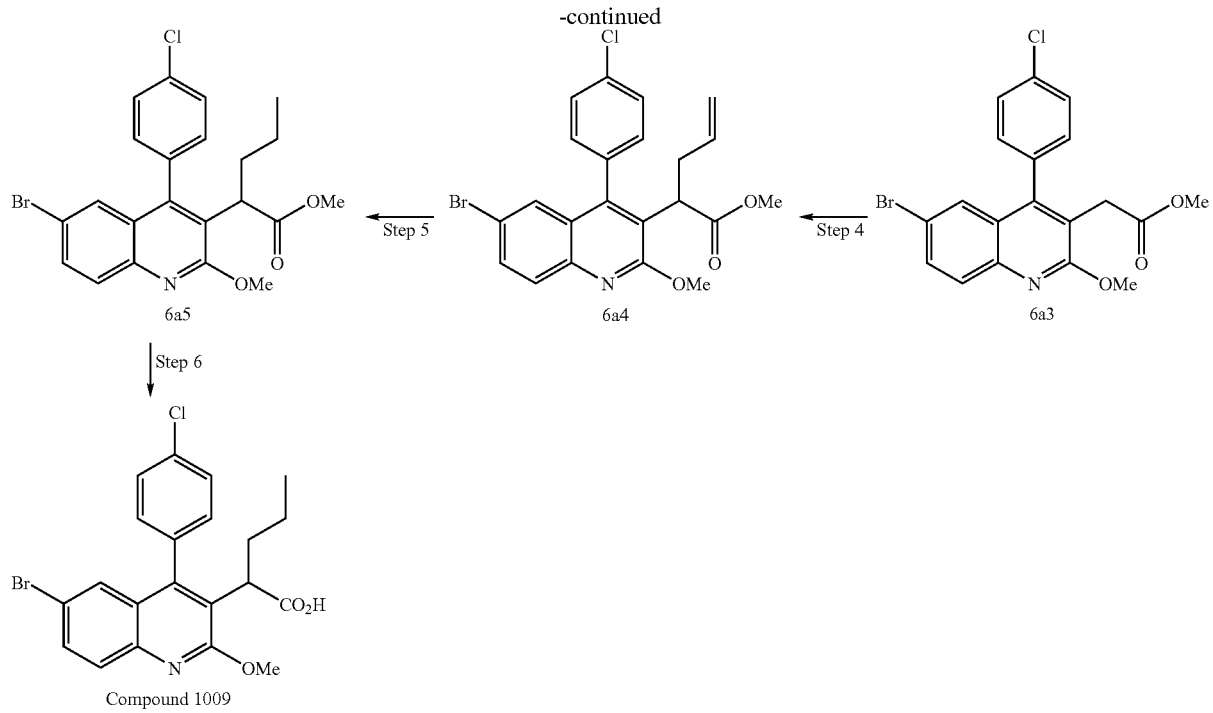

Step 1:

A mixture of compound 1b2 (Example 1B) (324.5 mg, 1.04 mmol), pyridine (3.0 mL) and 3-carbomethoxypropanoyl chloride (193 µL, 1.57 mmol) is allowed to stir at room temperature for 30 minutes. A further portion of 3-carbomethoxypropanoyl chloride (193 µL, 1.57 mmol) is added and stirring is continued for 1 hour. The mixture is added to saturated aqueous NaHCO$_3$ and extracted with EtOAc, and the EtOAc extract is washed with brine, dried (MgSO$_4$), filtered and concentrated. The residue is purified by flash chromatography to provide compound 6a1.

Step 2:

A mixture of compound 6a1 (450 mg, 1.04 mmol), NaOEt (21% in EtOH, 1.36 mL, 4.18 mmol) and EtOH (5.0 mL) is allowed to react at 80° C. for 1 hour, then cooled to room temperature and diluted with EtOAc. The mixture is acidified to approximately pH 1 with 1N HCl and the phases are separated. The organic phase is washed with brine, dried (MgSO$_4$), filtered and concentrated to provide compound 6a2.

Step 3:

To a solution of compound 6a2 (447 mg, 1.14 mmol) in EtOAc (10 mL) is added excess diazomethane in Et$_2$O and the mixture is allowed to stir at room temperature overnight. The mixture is concentrated and the residue is purified by flash chromatography (20-50% EtOAc/hexane) to provide compound 6a3.

Step 4:

To a mixture of compound 6a3 (51 mg, 0.121 mmol) and allyl bromide (105 µL, 1.21 mmol) in THF (1.5 mL), at 0° C. is added LiHMDS (1M in toluene, 182 µL, 0.182 mmol). The reaction mixture is allowed to stir at 0° C. for 45 minutes, then water is added. The mixture is diluted with EtOAc, the phases are separated, and the organic phase is washed with brine, dried (MgSO$_4$), filtered and concentrated. Purification of the residue by flash chromatography (15-20% EtOAc/hexane) provides compound 6a4.

Step 5:

A mixture of compound 6a4 (38 mg, 0.082 mmol), EtOH (2.0 mL) and Pt$_2$O$_5$ (5.0 mg) is purged with N$_2$ and allowed to stir under an atmosphere of H$_2$ for 20 minutes at room temperature. The mixture is filtered through a Millex®-HV filter and the filtrate is concentrated to provide compound 6a5.

Step 6:

A mixture of compound 6a5 (35.4 mg, 0.076 mmol) and 5N NaOH (70 µL, 0.38 mmol) in DMSO (1.5 mL) is allowed to react at 60° C. for 45 minutes and cooled to room temperature. The mixture is acidified with TFA and purified by preparative HPLC to provide compound 1009 (Table 1).

Example 7A

Preparation of Compound 1007

Table 1

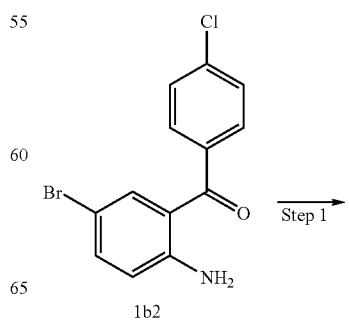

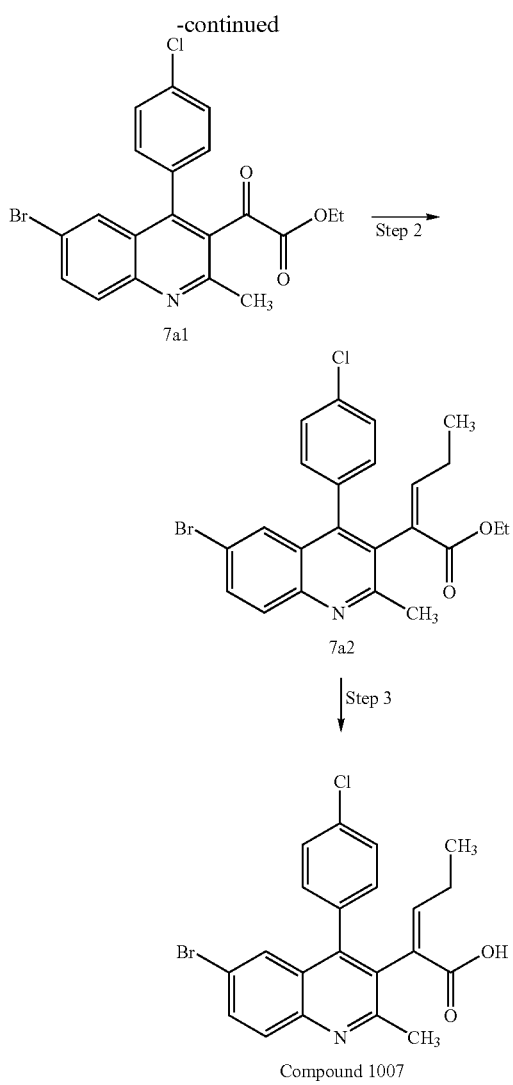

Step 1:
A mixture of compound 1b2 (Example 1B) (6.0 g, 19.3 mmol), ethyl acetopyruvate (3.6 mL, 25 mmol) and concentrated $H_2SO_4$ (0.90 mL) in AcOH (45 mL) is allowed to react at 130° C. for 3 h. The mixture is concentrated under reduced pressure and the residue is purified by flash chromatography (10-35% EtOAc/hexane) to provide compound 7a1.

Step 2:
To a mixture of $CH_3CH_2CH_2PPh_3Br$ (427.4 mg, 1.11 mmol) in anhydrous THF (5 mL) at 0° C. is added nBuLi (0.75 mL, 1.20 mmol) and the mixture is allowed to warm to room temperature over 30 minutes. The mixture is again cooled to 0° C. and to this mixture is added a mixture of compound 7a1 (400 mg, 0.924 mmol) in THF (1.5 mL). The mixture is allowed to stir at room temperature for 2 h, and saturated $NH_4Cl$ (10 mL) is added. The mixture is extracted three times with EtOAc and the combined organic extract is washed with brine, dried ($MgSO_4$), filtered and concentrated. The residue is purified by flash chromatography (10% EtOAc/hexane) to provide compound 7a2.

Step 3:
A mixture of compound 7a2 (16 mg, 0.035 mmol) and 2.5M NaOH (70 µL, 0.175 mmol) in DMSO (1 mL) is allowed to react for 30 minutes at room temperature. The mixture is acidified with TFA and purified by preparative HPLC to give compound 1007 (Table 1).

Example 8A

Synthesis of Derivative D1

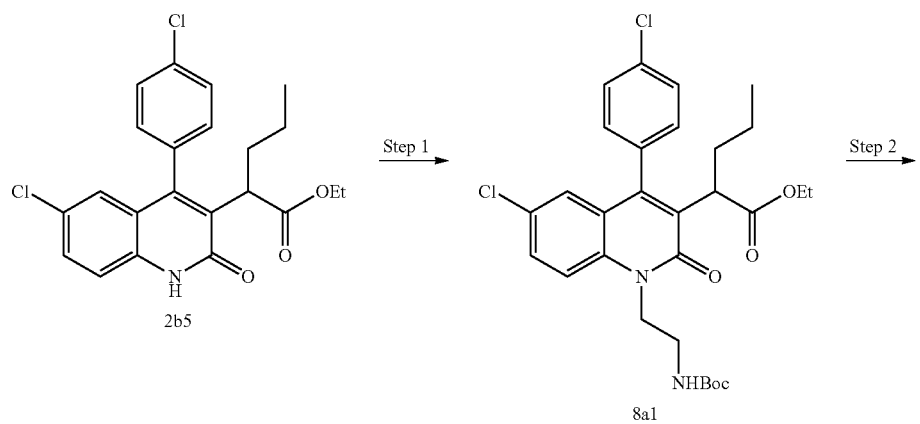

-continued

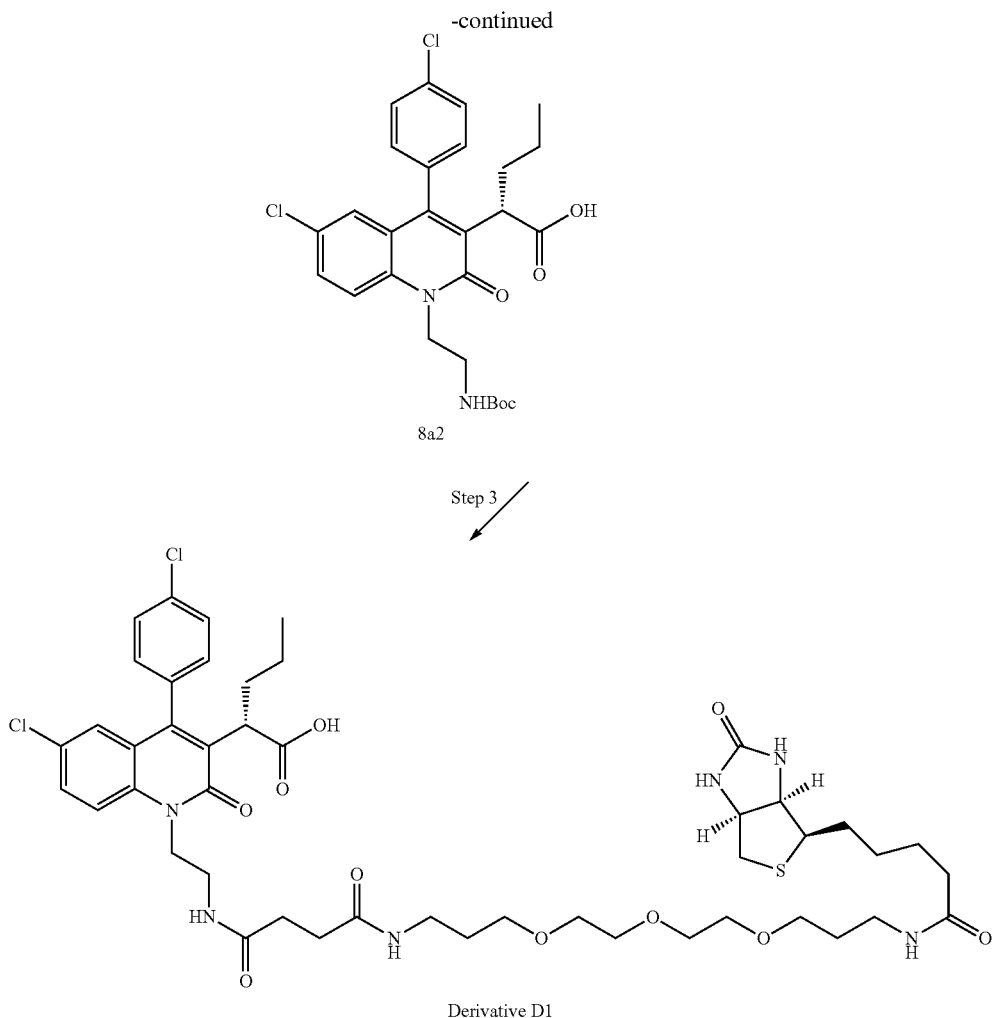

Step 1:
A solution of (Boc)₂O (1 M in THF, 2.47 mL, 2.47 mmol) is added to a solution of H₂NCH₂CH₂Br.HBr (506 mg, 2.47 mmol) and Et₃N (860 mL, 6.175 mmol) in THF (10 mL). The reaction mixture is stirred at RT for 18 h and is partitioned between EtOAc (100 mL) and saturated aqueous NaHCO₃ (25 mL). The organic phase is washed with brine, dried over anhydrous MgSO₄ and concentrated. The residue is purified by chromatography (5% to 20% EtOAc/hex) to give BocNHCH₂CH₂Br.

To a cooled solution (0° C.) of compound 2b5 (Example 2B) (200 mg, 0.495 mmol) in DMF (3 mL) is added KOtBu (67 mg, 0.598 mmol). The mixture is stirred for 15 min, then a solution of BocNHCH₂CH₂Br (160 mg, 0.717 mmol) in DMF (2 mL) is added. The reaction mixture was stirred at RT for 18 h. Water (1 mL) is added, the mixture was diluted with EtOAc (100 mL) and the organic phase is washed with saturated aqueous NaHCO₃ (25 mL) and brine, dried over anhydrous MgSO₄ and concentrated. The residue is purified by chromatography (10% to 30% EtOAc/hex) to give compound 8a1.

Step 2:
To a solution of compound 8a1 (96 mg, 0.175 mmol) in DMSO (2.5 mL) is added 5N NaOH (175 μL, 0.875 mmol). The mixture is stirred for 30 min and purified by semi preparative HPLC to afford the Boc-deprotected carboxylic acid.

The compound is treated with Boc₂O in the presence of NaOH to provide compound 8a2 as a racemic mixture. Separation by chiral HPLC, using a ChiralCel OD-R column (20× 250 mm from Chiral Technologies Inc) and an isocratic solvent system of 20% H₂O (containing 0.06% TFA) and 80% of a solvent mixture composed of 75% MeCN in H₂O (containing 0.06% TFA) provides the (S)-enantiomer 8a2.

Step 3:
To a mixture of compound 8a2 (9.2 mg, 0.017 mmol) and CH₂Cl₂ (1.5 mL) is added TFA (750 μL). The mixture is stirred at RT for 1 h and concentrated. The residue is dissolved in CH₂Cl₂ (1.0 mL) and to this mixture is added Et₃N (7 μL, 0.051 mmol), followed by EZ-Link™ TFP-PEO-biotin (Pierce; 17.2 mg, 0.025 mmol). The reaction mixture is stirred at RT for 18 h, the solvent is evaporated and the residue is purified by semi-preparative HPLC to afford derivative D1.

Example 9

C8166 HIV-1 Luciferase Assay $EC_{50}$

The assay used to measure inhibition of HIV replication is as described in WO 2004/050643, pages 73-75, with the following modifications:

Preparation of Compounds

Serial dilutions of HIV-1 inhibitors are prepared in complete media from DMSO stock solutions. Eleven serial dilutions of desired concentration are prepared in a 1 mL deep well titer plate (96 wells). The 12$^{th}$ well contains complete media with no inhibitor and serves as the positive control. All samples contain the same concentration of DMSO ($\leq$0.1% DMSO). Inhibitor is added, to triplicate wells, of a 96 well tissue culture treated clear view black microtiter plate (Corning Costar catalogue #3904). The total volume per well is 200 μL of media containing the cells and inhibitor. The last row is reserved for uninfected C8166 LTRluc cells to serve as the background blank control and the first row is media alone.

Infection of Cells

Count C8166 LTRluc cells and place in a minimal volume of complete RPMI 1640 in a tissue culture flask (ex. 30×10$^6$ cells in 10 mL media/25 cm$^2$ flask). Infect cells with HIV-1 at a moi of 0.005. Incubate cells for 1.5 hours at 37° C. on a rotating rack in a 5% CO$_2$ incubator. Resuspend cells in complete RPMI to give a final concentration of 25,000-cells/well. Add cells to wells of 96 well microtiter plate containing inhibitors. Add 25,000 uninfected C8166-LTRluc cells/well in 200 μL complete RPMI to last row for background control. Incubate cells at 37° C. in 5% CO$_2$ incubator for 3 days.

Tables of Compounds

The following tables list compounds representative of the invention. Representative compounds listed in Tables 1 to 3 below have EC$_{50}$ values of no more than 20 μM when tested in the HIV-1 luciferase assay of Example 9.

Retention times (t$_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | R$^2$ | R$^3$ | R$^4$ | R$^6$ | R$^7$ | t$_R$ (min) | MS (M + H)$^+$ |
|---|---|---|---|---|---|---|---|
| 1001 | CH$_3$ | 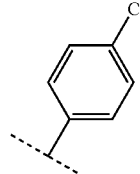 | 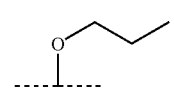 | Br | H | 5.2 | 419.8 |
| 1002 | CH$_3$ | 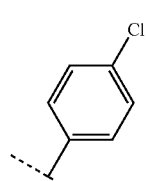 |  | Br | H | 6.2 | 447.8 |
| 1003 | CH$_3$ | 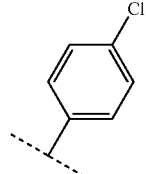 | 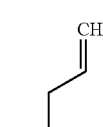 | Br | H | 4.5 | 419.9 |
| 1004 | CH$_3$ | 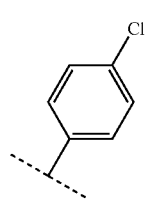 | | Br | H | 5.1 | 430.0 |

TABLE 1-continued

| Cpd | R² | R³ | R⁴ | R⁶ | R⁷ | t_R (min) | MS (M + H)⁺ |
|---|---|---|---|---|---|---|---|
| 1005 | CH₃ | OCH₃ | 4-CF₃-C₆H₄ | Cl | H | 4.8 | 410.0 |
| 1006 | CH₃ | n-Pr | 4-Cl-C₆H₄ | Br | H | 5.3 | 432.0 |
| 1007 | CH₃ | CH=CHCH₃ | 4-Cl-C₆H₄ | Br | H | 5.0 | 430.0 |
| 1008 | CH₃ | n-Pr | 4-Br-C₆H₄ | Cl | H | 5.9 | 432.0 |
| 1009 | —OCH₃ | n-Pr | 4-Cl-C₆H₄ | Br | H | 7.5 | 448.0 |
| 1010 | —CH(CH₃)₂ | n-Pr | 4-Cl-C₆H₄ | Br | H | 7.7 | 460.0 |
| 1011 | CH₃ | OCH₃ | 4-Cl-C₆H₄ | H | H | 3.5 | 342.1 |

TABLE 1-continued

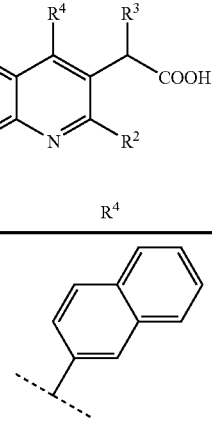

| Cpd | R² | R³ | R⁴ | R⁶ | R⁷ | $t_R$ (min) | MS (M + H)⁺ |
|---|---|---|---|---|---|---|---|
| 1012 | CH₃ | ⎯CH₂CH₂CH₃ | 2-naphthyl | Cl | H | 5.9 | 404.1 |
| 1013 | CH₃ | ⎯CH₂CH₂CH₃ | 4-methylphenyl | Cl | H | 5.6 | 368.1 |
| 1014 | CH₃ | ⎯CH₂CH₂CH₃ | 3-fluoro-4-methylphenyl | Cl | H | 5.7 | 386.1 |
| 1015 | CH₃ | ⎯CH(OCH₃)⎯ | 1-methylindol-6-yl | Cl | H | 4.7; 4.9 mixture of diastereomers | 395.1 |
| 1016 | CH₃ | ⎯CH(OCH₃)⎯ | 2,3-dihydrobenzofuran-5-yl | Cl | H | 4.3; 4.3 mixture of diastereomers | 384.1 |
| 1017 | CH₃ | ⎯CH(OCH₃)⎯ | 4-methoxyphenyl | Cl | H | 4.3 | 372.1 |
| 1018 | CH₃ | ⎯CH₂CH₂CH₃ | 2,4-dimethylphenyl | Cl | H | 5.8; 5.9 mixture of diastereomers | 382.1 |

TABLE 1-continued

| Cpd | R² | R³ | R⁴ | R⁶ | R⁷ | t_R (min) | MS (M + H)⁺ |
|---|---|---|---|---|---|---|---|
| 1019 | CH₃ | -O-CH₃ (methoxymethyl) | 1H-indol-6-yl | Cl | H | 4.2; 4.6 mixture of diastereomers | 381.0 |
| 1020 | CH₃ | (5-methylisoxazol-3-yl)methoxy | 4-chlorophenyl | Br | H | 5.6 | 501.0 |
| 1021 | CH₃ | -O-CH₃ (methoxymethyl) | benzofuran-5-yl | Cl | H | 4.1; 4.1 mixture of diastereomers | 382.0 |
| 1022 | CH₃ | (2-methylallyloxy)methyl | 4-chlorophenyl | Br | H | 4.2 | 460.0 |
| 1023 | CH₃ | 3-(1H-pyrrol-1-yl)propoxy | 4-chlorophenyl | Br | H | 5.6 | 512.1 |
| 1024 | CH₃ | -O-CH₃ (methoxymethyl) | 4-methylphenyl | Cl | H | 4.1 | 356.0 |

TABLE 1-continued

| Cpd | R² | R³ | R⁴ | R⁶ | R⁷ | t_R (min) | MS (M + H)⁺ |
|---|---|---|---|---|---|---|---|
| 1025 | CH₃ | -CH(CH₃)-O-CH(CH₃)₂ (1-methoxyethyl with isopropyl) | 4-Cl-phenyl | Br | H | 5.7 | 448.0 |
| 1026 | CH₃ | -CH₂-O-CH₂-cyclopropyl | 4-Cl-phenyl | Br | H | 5.2 | 459.9 |
| 1027 | CH₃ | -CH₂-O-CH₂-(5-methylisoxazol-3-yl) | 4-CH₃-phenyl | Br | H | 4.7 | 483.0 |
| 1028 | CH₃ | -CH₂-O-CH₂-CH=CH₂ | 4-Cl-phenyl | Br | H | 5.0 | 446.0 |
| 1029 | CH₃ | -CH(O-CH₃)- | 4-Cl-phenyl | Cl | H | 4.7 | 376.0 |
| 1030 | CH₃ | -CH(CH₃)-CH₂-CH₃ | 4-F-phenyl | Cl | H | 5.2 | 372.1 |
| 1031 | CH₃ | -CH(CH₃)-CH₂-CH₃ | phenyl | Cl | H | 5.0 | 354.1 |

TABLE 1-continued
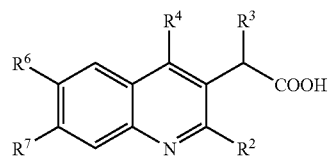
| Cpd | R² | R³ | R⁴ | R⁶ | R⁷ | t_R (min) | MS (M + H)⁺ |
|---|---|---|---|---|---|---|---|
| 1032 | CH₃ | n-propyl | 4-methylphenyl | Br | H | 5.0 | 414.0 |
| 1033 | CH₃ | n-propyl | 4-methylphenyl | H | H | 4.3 | 334.1 |
| 1034 | CH₃ | n-propyl | 4-vinylphenyl | Cl | H | 5.1 | 380.1 |
| 1035 | CH₃ | isobutyl | 4-chlorophenyl | Br | H | 6.1 | 446.0 |
| 1036 | CH₃ | n-propyl | 4-methoxyphenyl | Cl | H | 4.7 | 384.1 |
| 1037 | CH₃ | n-propyl | 4-cyclopropylphenyl | Cl | H | 5.2 | 394.1 |

TABLE 1-continued
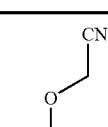
| Cpd | R² | R³ | R⁴ | R⁶ | R⁷ | t_R (min) | MS (M + H)⁺ |
|---|---|---|---|---|---|---|---|
| 1038 | CH₃ | 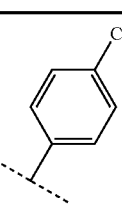 | 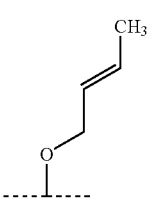 4-Cl-C₆H₄ | Br | H | 5.2 | 444.9 |
| 1039 | CH₃ | 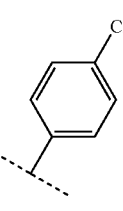 | 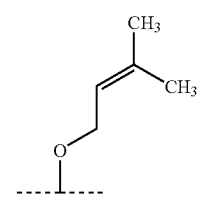 4-Cl-C₆H₄ | Br | H | 6.0 | 460 |
| 1040 | CH₃ | 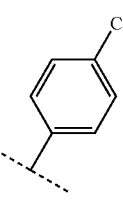 | 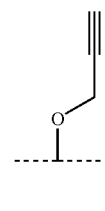 4-Cl-C₆H₄ | Br | H | 6.3 | 474 |
| 1041 | CH₃ | 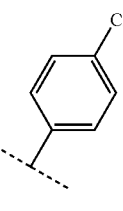 | 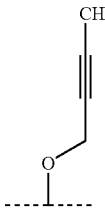 4-Cl-C₆H₄ | Br | H | 5.3 | 443.9 |
| 1042 | CH₃ | 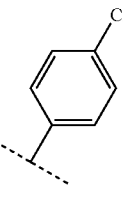 | 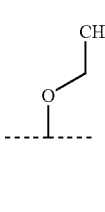 4-Cl-C₆H₄ | Br | H | 5.6 | 458 |
| 1043 | CH₃ | 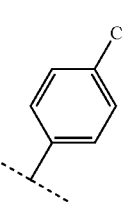 | 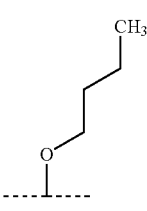 4-Cl-C₆H₄ | Br | H | 5.3 | 434 |
| 1044 | CH₃ | 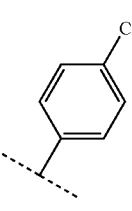 | 4-Cl-C₆H₄ | Br | H | 6.4 | 462 |

TABLE 1-continued
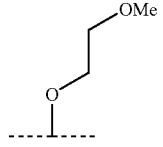
| Cpd | R² | R³ | R⁴ | R⁶ | R⁷ | t_R (min) | MS (M + H)⁺ |
|---|---|---|---|---|---|---|---|
| 1045 | CH₃ | 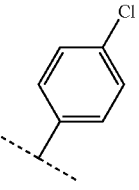 | 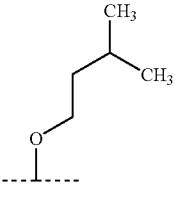 | Br | H | 5.0 | 464 |
| 1046 | CH₃ | 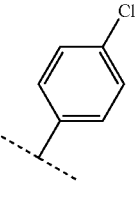 | 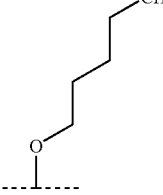 | Br | H | 6.8 | 476 |
| 1047 | CH₃ | 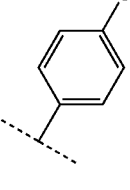 | 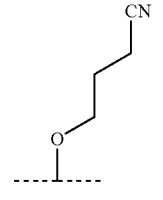 | Br | H | 6.8 | 476 |
| 1048 | CH₃ | 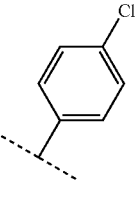 | 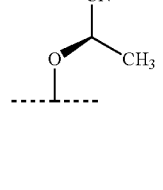 | Br | H | 5.2 | 473 |
| 1049 | CH₃ | 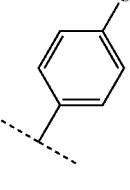 | 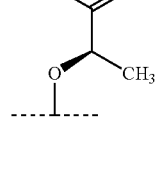 | Br | H | 5.5 | 458.9 |
| 1050 | CH₃ | 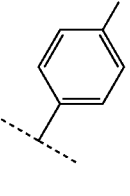 | | Br | H | 5.0 | 476 |

TABLE 1-continued
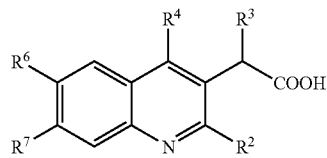
| Cpd | R² | R³ | R⁴ | R⁶ | R⁷ | $t_R$ (min) | MS (M + H)⁺ |
|---|---|---|---|---|---|---|---|
| 1051 | CH₃ | 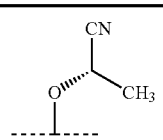 | 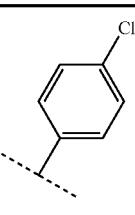 | Br | H | 5.7 | 459 |
| 1052 | CH₃ | 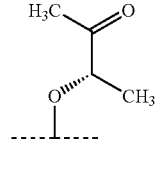 | 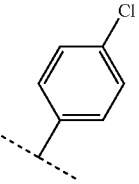 | Br | H | 5.4 | 476 |
| 1053 | CH₃ | 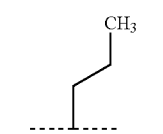 | 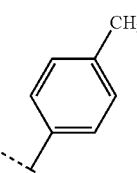 | F | F | 5.6 | 370.1 |
| 1054 | CH₃ | 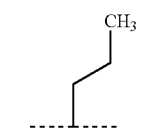 | 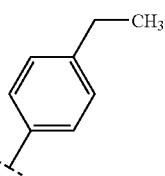 | Cl | H | 5.2 | 382.1 |
| 1055 | CH₃ | 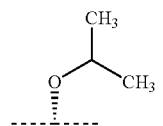 | 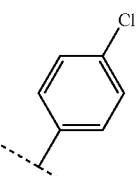 | Br | H | 4.9 | 447.9 |
| 1056 | CH₃ | 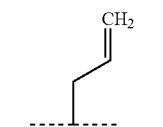 | 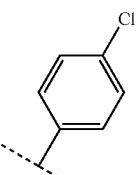 | Cl | H | 5.2 | 386.0 |
| 1057 | CH₃ | 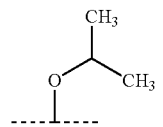 | 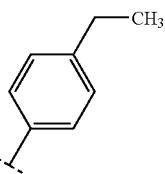 | Cl | H | 5.2 | 398.1 |

TABLE 1-continued
| Cpd | R² | R³ | R⁴ | R⁶ | R⁷ | t_R (min) | MS (M + H)⁺ |
|---|---|---|---|---|---|---|---|
| 1058 | CH₃ | 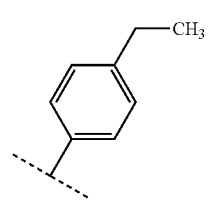 | 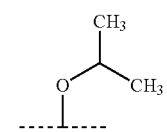 | Cl | H | 4.9 | 384.1 |
| 1059 | CH₃ | 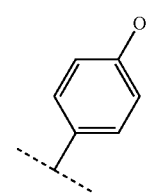 | 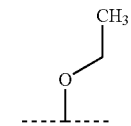 | Cl | H | 4.5 | 400.1 |
| 1060 | CH₃ | 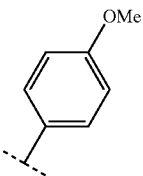 | 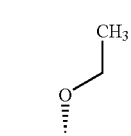 | Cl | H | 4.2 | 386.0 |
| 1061 | CH₃ | 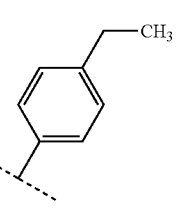 | 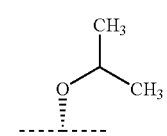 | Cl | H | 5.0 | 384.1 |
| 1062 | CH₃ | 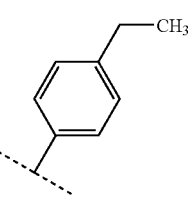 | 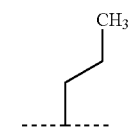 | Cl | H | 5.2 | 398.1 |
| 1063 | CH₃ | 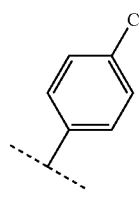 |  | Cl | H | 5.6 | 388 |

TABLE 1-continued
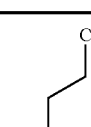
| Cpd | R² | R³ | R⁴ | R⁶ | R⁷ | t_R (min) | MS (M + H)⁺ |
|---|---|---|---|---|---|---|---|
| 1064 | CH₃ | CH₃ (butyl) | 3-Cl,4-F-phenyl | Cl | H | 5.7; 5.9 mixture of diastereomers | 406 |
| 1065 | CH₃ | CH₃ (butyl) | 3-Cl-phenyl | Cl | H | 5.5; 5.6 mixture of diastereomers | 388 |
| 1066 | CH₃ | CH₃ (butyl) | 3-MeO-phenyl | Cl | H | 4.9; 5.0 mixture of diastereomers | 384.1 |
| 1067 | CH₃ | CH₃ (butyl) | benzofuran-2-yl | Cl | H | 6.3 | 394.1 |
| 1068 | CH₃ | CH₃ (butyl) | 5-Cl-thiophen-2-yl | Cl | H | 6.3 | 394 |
| 1069 | CH₃ | CH₃ (butyl) | 3-CH₃,4-Cl-phenyl | Cl | H | 6.0 | 402 |
| 1070 | CH₃ | CH₃ (butyl) | 3-CH₃,4-OMe-phenyl | Cl | H | 5.1 | 398.1 |

TABLE 1-continued
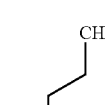
| Cpd | R² | R³ | R⁴ | R⁶ | R⁷ | $t_R$ (min) | MS (M + H)⁺ |
|---|---|---|---|---|---|---|---|
| 1071 | CH₃ | CH₃ (propyl) | 1-methylindol-5-yl | Cl | H | 5.0 | 407.1 |
| 1072 | CH₃ | CH₃ (propyl) | 3-chloro-4-methylphenyl | Cl | H | 5.9; 6.0 mixture of diastereomers | 402 |
| 1073 | CH₃ | OEt (ethoxy) | 4-methoxyphenyl | Cl | H | 4.2 | 386.0 |
| 1074 | CH₃ | OiPr (isopropoxy) | 4-methoxyphenyl | Cl | H | 4.5 | 400.1 |
| 1075 | CH₃ | CH₃ (propyl) | 4-(methylthio)phenyl | Cl | H | 5.4 | 400 |
| 1076 | CH₃ | CH₃ (propyl) | thiophen-2-yl | Cl | H | 5.2 | 360 |
| 1077 | CH₃ | CH₃ (propyl) | 3,4-difluorophenyl | Cl | H | 5.4; 5.5 mixture of diastereomers | 390 |

TABLE 1-continued

| Cpd | R² | R³ | R⁴ | R⁶ | R⁷ | t_R (min) | MS (M + H)⁺ |
|---|---|---|---|---|---|---|---|
| 1078 | CH₃ | -O-C(CH₃)₃ | 4-CH₃-C₆H₄-CH₂- | Cl | H | 5.5 | 412.2 |
| 1079 | CH₃ | -O-C(CH₃)₃ | 4-Cl-C₆H₄- | Br | H | 5.1 | 462.0 |
| 1080 | CH₃ | -O-CH₂CH₃ | 4-Cl-C₆H₄- | Cl | H | 4.7 | 390.0 |
| 1081 | CH₃ | -O-CH(CH₃)₂ | 4-(C(O)CH₃)-C₆H₄- | Cl | H | 4.0 | 412.0 |
| 1082 | CH₃ | -O-CH(CH₃)₂ | 4-Cl-C₆H₄- | H | H | 4.0 | 370.0 |
| 1083 | CH₃ | -O-CH(CF₃)₂ | 4-CH₃-C₆H₄-CH₂- | Cl | H | 6.3 | 506.0 |

TABLE 1-continued

| Cpd | R² | R³ | R⁴ | R⁶ | R⁷ | t_R (min) | MS (M + H)⁺ |
|---|---|---|---|---|---|---|---|
| 1084 | CH₃ | phenoxy | 4-methylbenzyl | Cl | H | 5.8 | 432.1 |
| 1085 | CH₃ | tert-amyloxy | 4-methylbenzyl | Cl | H | 5.8 | 426.2 |
| 1086 | CH₃ | (1-methylcyclopentyl)oxy | 4-methylbenzyl | Cl | H | 5.9 | 438.2 |
| 1087 | CH₃ | isopropoxy | 4-(dimethylamino)phenyl | Cl | H | 4.2 | 413.2 |
| 1088 | CH₃ | isopropoxy | quinolin-6-yl | Cl | H | 3.1 | 421.2 |
| 1089 | CH₃ | tert-butoxy | 4-methylbenzyl | Cl | H | 5.4 | 412.1 |

TABLE 1-continued

| Cpd | R² | R³ | R⁴ | R⁶ | R⁷ | t_R (min) | MS (M + H)⁺ |
|---|---|---|---|---|---|---|---|
| 1090 | CH₃ | 1-methylcyclohexyloxy | 4-methylbenzyl | Cl | H | 6.2 | 452.2 |
| 1091 | CH₃ | cyclobutyloxy | 4-methylbenzyl | Cl | H | 5.4 | 410.2 |
| 1092 | CH₃ | cyclopentyloxy | 4-methylbenzyl | Cl | H | 5.7 | 424.2 |
| 1093 | CH₃ | isopropyloxy | 4-(1,1-difluoroethyl)benzyl | Cl | H | 4.8 | 434.1 |
| 1094 | CH₃ | 1-ethylcyclopropyloxy | 4-methylbenzyl | Cl | H | 5.6 | 424.2 |
| 1095 | CH₃ | 1-methylcyclobutyloxy | 4-methylbenzyl | Cl | H | 5.6 | 424.2 |

TABLE 1-continued

| Cpd | R² | R³ | R⁴ | R⁶ | R⁷ | t_R (min) | MS (M+H)⁺ |
|---|---|---|---|---|---|---|---|
| 1096 | CH₃ | 1-methylcyclopropyl-O- | 4-methylbenzyl | Cl | H | 5.2 | 410.2 |
| 1097 | CH₃ | pentan-3-yl-O- | 4-methylbenzyl | Cl | H | 5.6 | 426.2 |
| 1098 | CH₃ | isopropyl-O- | 4-ethoxybenzyl | Cl | H | 5.2 | 414.2 |
| 1099 | CH₃ | (S)-butan-2-yl-O- | 4-methylbenzyl | Cl | H | 5.3 | 412.2 |
| 1100 | CH₃ | isopropyl-O- | benzo[1,3]dioxol-5-ylmethyl | Cl | H | 4.5; 4.7 mixture of diastereomers | 414.1 |
| 1101 | —CH₂CH₃ | butyl | 4-chlorobenzyl | Cl | H | 5.4 | 402.1 |
| 1102 | CH₃ | (R)-butan-2-yl-O- | 4-methylbenzyl | Cl | H | 5.3 | 412.2 |

TABLE 1-continued

| Cpd | R² | R³ | R⁴ | R⁶ | R⁷ | t_R (min) | MS (M + H)⁺ |
|---|---|---|---|---|---|---|---|
| 1103 | CH₃ | -OC(CH₃)₂CF₃ | 4-CH₃-C₆H₄-CH₂- | Cl | H | 5.8 | 466.1 |
| 1104 | CH₃ | -OC(CH₃)(CH₂F)₂ | 4-CH₃-C₆H₄-CH₂- | Cl | H | 5.2 | 448.2 |
| 1105 | CH₃ | 1-ethyl-cyclobutyloxy | 4-CH₃-C₆H₄-CH₂- | Cl | H | 5.9 | 438.2 |
| 1106 | CH₃ | -OC(CH₃)₃ | 4-Cl-C₆H₄- | Br | H | 5.1 | 462.0 |
| 1107 | CH₃ | -OC(CH₃)₂CH₂Cl | 4-CH₃-C₆H₄-CH₂- | Cl | H | 5.5 | 446.1 |
| 1108 | CH₃ | -OC(CH₃)₂CH₂CH₂CH₃ | 4-CH₃-C₆H₄-CH₂- | Cl | H | 6.1 | 440.2 |
| 1109 | CH₃ | -OCH(CH₃)₂ | C₆H₅-CH₂- | Cl | H | 4.8 | 370.1 |

TABLE 1-continued

| Cpd | R² | R³ | R⁴ | R⁶ | R⁷ | t_R (min) | MS (M + H)⁺ |
|---|---|---|---|---|---|---|---|
| 1110 | CH₃ | -O-CH(CH₃)₂ | 4-Br-C₆H₄- | Cl | H | 5.7 | 448.0 |
| 1111 | CH₃ | -O-CH(CH₃)₂ | naphthalen-1-yl | Cl | H | 5.5 | 420.2 |
| 1112 | CH₃ | -O-CH(CH₃)₂ | 4-Cl-C₆H₄- | Cl | H | 5.6 | 404.1 |
| 1113 | CH₃ | -O-CH(CH₃)₂ | 4-CH₃-C₆H₄- | Cl | H | 5.2 | 384.2 |
| 1114 | CH₃ | -O-CH(CH₃)₂ | 3-CH₃-C₆H₄- | Cl | H | 5.2 | 384.2 |
| 1115 | CH₃ | -O-CH(CH₃)₂ | 4-SCH₃-C₆H₄- | Cl | H | 5.3 | 416.1 |
| 1116 | CH₃ | -O-CH(CH₃)₂ | 2-CH₃-C₆H₄- | Cl | H | 5.1 | 384.2 |

TABLE 1-continued

| Cpd | R² | R³ | R⁴ | R⁶ | R⁷ | t_R (min) | MS (M + H)⁺ |
|---|---|---|---|---|---|---|---|
| 1117 | CH₃ | -O-CH(CH₃)CH₃ | 2-thienyl | Cl | H | 5.0 | 376.1 |
| 1118 | CH₃ | -O-CH(CH₃)CH₃ | 3-thienyl | Cl | H | 4.6; 4.6 mixture of diastereomers | 376.1 |
| 1119 | CH₃ | -O-CH(CH₃)CH₃ | 4-(CF₃)phenyl | Cl | H | 6.0 | 438.1 |
| 1120 | CH₃ | -O-CH(CH₃)CH₃ | 3-fluorophenyl | Cl | H | 5.1; 5.1 mixture of diastereomers | 388.1 |
| 1121 | CH₃ | -O-CH(CH₃)CH₃ | 3-methyl-2-thienyl | Cl | H | 5.2; 5.4 mixture of diastereomers | 390.1 |
| 1122 | CH₃ | -O-CH(CH₃)CH₃ | 4-vinylphenyl | Cl | H | 5.4 | 396.2 |
| 1123 | CH₃ | -O-CH(CH₃)CH₃ | 3-pyridyl | Cl | H | 3.1 | 371.1 |

TABLE 1-continued

| Cpd | R² | R³ | R⁴ | R⁶ | R⁷ | t_R (min) | MS (M + H)⁺ |
|---|---|---|---|---|---|---|---|
| 1124 | CH₃ | -O-CH(CH₃)₂ | 4-(hydroxymethyl)phenyl | Cl | H | 3.6 | 400.2 |
| 1125 | CH₃ | -O-CH(CH₃)₂ | 3-fluoro-4-methoxyphenyl | Cl | H | 4.8; 5.0 mixture of diastereomers | 418.1 |
| 1126 | CH₃ | -O-CH(CH₃)₂ | 4-ethylphenyl | Cl | H | 6.1 | 412.2 |
| 1127 | CH₃ | -O-CH(CH₃)₂ | 3,4-dimethylphenyl | Cl | H | 5.5; 5.5 mixture of diastereomers | 398.2 |
| 1128 | CH₃ | -O-CH(CH₃)₂ | 2,3-dihydro-1,4-benzodioxin-6-yl | Cl | H | 4.5; 4.7 mixture of diastereomers | 428.2 |
| 1129 | CH₃ | -O-CH(CH₃)₂ | 4-tert-butylphenyl | Cl | H | 6.3 | 426.2 |

TABLE 1-continued

| Cpd | R² | R³ | R⁴ | R⁶ | R⁷ | $t_R$ (min) | MS $(M + H)^+$ |
|---|---|---|---|---|---|---|---|
| 1130 | CH₃ | OiPr | 3,4-dimethoxyphenyl | Cl | H | 4.2; 4.4 mixture of diastereomers | 430.2 |
| 1131 | CH₃ | OiPr | 4-isopropylphenyl | Cl | H | 6.0 | 412.2 |
| 1132 | CH₃ | OiPr | 4-hydroxyphenyl | Cl | H | 3.7 | 386.1 |
| 1133 | CH₃ | OiPr | benzothiophen-2-yl | Cl | H | 6.3 | 426.1 |
| 1134 | CH₃ | OiPr | benzothiophen-3-yl | Cl | H | 5.6 | 426.1 |
| 1135 | CH₃ | OiPr | 6-methoxypyridin-3-yl | Cl | H | 4.4 | 401.2 |
| 1136 | CH₃ | OiPr | 3-methyl-4-methoxyphenyl | Cl | H | 5.1; 5.3 mixture of diastereomers | 414.2 |

TABLE 1-continued

| Cpd | R² | R³ | R⁴ | R⁶ | R⁷ | t_R (min) | MS (M + H)⁺ |
|---|---|---|---|---|---|---|---|
| 1137 | CH₃ | OCH(CH₃)₂ | quinolin-3-yl | Cl | H | 4.4 | 421.2 |
| 1138 | CH₃ | OCH(CH₃)₂ | 2,4-dimethylphenyl | Cl | H | 5.6 | 398.2 |
| 1139 | CH₃ | OCH(CH₃)₂ | 4-chloro-3-methylphenyl | Cl | H | 5.9 | 418.1 |
| 1140 | CH₃ | OCH(CH₃)₂ | 4-chloro-2-methylphenyl | Cl | H | 5.9 | 418.1 |
| 1141 | CH₃ | OCH(CH₃)₂ | pyrimidin-5-yl | Cl | H | 3.6 | 372.1 |
| 1142 | CH₃ | OCH(CH₃)₂ | 2-methoxypyrimidin-5-yl | Cl | H | 4.0 | 402.2 |
| 1143 | CH₃ | OCH(CH₃)₂ | 6-chloropyridin-3-yl | Cl | H | 4.8 | 405.1 |

TABLE 1-continued
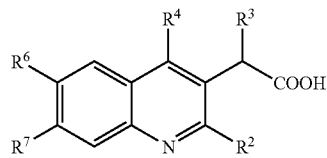
| Cpd | R² | R³ | R⁴ | R⁶ | R⁷ | $t_R$ (min) | MS (M + H)⁺ |
|---|---|---|---|---|---|---|---|
| 1144 | CH₃ | 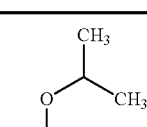 | 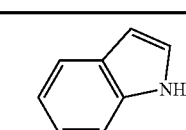 | Cl | H | 4.3; 5.0 mixture of diastereomers | 409.2 |
| 1145 | CH₃ | 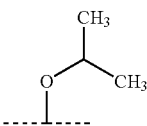 | 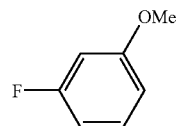 | Cl | H | 5.1; 5.2 mixture of diastereomers | 418.2 |
| 1146 | CH₃ | 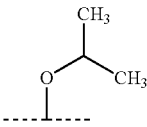 | 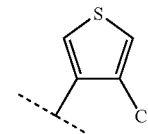 | Cl | H | 5.0; 5.1 mixture of diastereomers | 390.1 |
| 1147 | CH₃ | 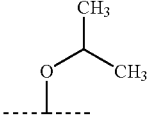 | 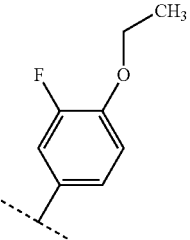 | Cl | H | 5.3; 5.4 mixture of diastereomers | 432.2 |
| 1148 | CH₃ | 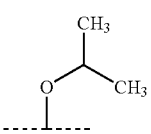 | 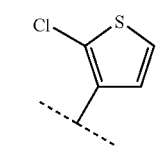 | Cl | H | 5.2; 5.6 mixture of diastereomers | 410.1 |
| 1149 | CH₃ | 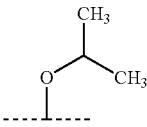 | 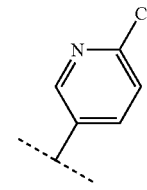 | Cl | H | 3.0 | 385.2 |
| 1150 | CH₃ | 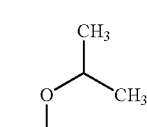 | 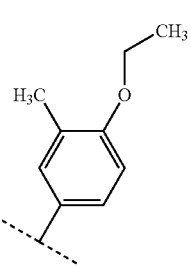 | Cl | H | 5.6; 5.8 mixture of diastereomers | 428.2 |

TABLE 1-continued

| Cpd | R² | R³ | R⁴ | R⁶ | R⁷ | t_R (min) | MS (M + H)⁺ |
|---|---|---|---|---|---|---|---|
| 1151 | CH₃ | isopropoxy | 2-hydroxyphenyl | Cl | H | 4.2 | 386.1 |
| 1152 | CH₃ | isopropoxy | 2-hydroxyphenyl | H | H | 3.6 | 352.1 |
| 1153 | CH₃ | isopropoxy | 3-hydroxyphenyl | Cl | H | 3.6; 4.2 mixture of diastereomers | 386.1 |
| 1154 | CH₃ | isopropoxy | 3-hydroxyphenyl | H | H | 2.8; 3.4 mixture of diastereomers | 352.1 |
| 1155 | CH₃ | tert-butoxy | 4-(2-fluoroethyl)phenyl | Cl | H | 4.6 | 430.2 |
| 1156 | CH₃ | tert-butoxy | 4-(2-fluoroethyl)phenyl | Cl | H | 4.6 | 430.1 |
| 1157 | CH₃ | tert-butoxy | 4-methylphenyl | H | H | 4.8 | 378.2 |

TABLE 1-continued
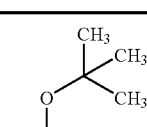
| Cpd | R² | R³ | R⁴ | R⁶ | R⁷ | $t_R$ (min) | MS (M + H)⁺ |
|---|---|---|---|---|---|---|---|
| 1158 | CH₃ | OC(CH₃)₃ | 4-Cl-C₆H₄ | H | H | 4.4 | 384.1 |
| 1159 | CH₃ | OC(CH₃)₃ | 4-CH₃-C₆H₄ | H | H | 4.8 | 378.2 |
| 1160 | CH₃ | OC(CH₃)₃ | 4-Cl-C₆H₄ | H | H | 4.4 | 384.1 |
| 1161 | CH₃ | OCH(CH₃)₂ | 4-CH₃-C₆H₄ | H | H | 4.0 | 350.1 |
| 1162 | CH₃ | OC(CH₃)₃ | 4-F-C₆H₄ | Cl | H | 4.4 | 416.1 |
| 1163 | CH₃ | OC(CH₃)₃ | 4-F-C₆H₄ | H | H | 3.8 | 382.1 |
| 1164 | CH₃ | O-cyclopentyl | 4-Cl-C₆H₄ | Br | H | 6.3 | 474 |

TABLE 1-continued
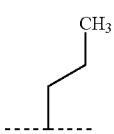
| Cpd | R² | R³ | R⁴ | R⁶ | R⁷ | t_R (min) | MS (M + H)⁺ |
|---|---|---|---|---|---|---|---|
| 1165 | CH₃ | 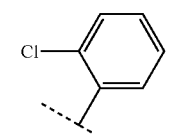 | 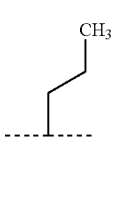 | Cl | H | 5.6 | 388 |
| 1166 | CH₃ | 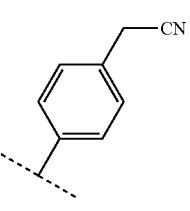 | 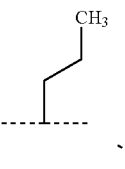 | Cl | H | 4.5 | 393.1 |
TABLE 2
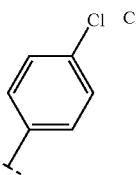
| Cpd | R¹ | R³ | R⁴ | R⁶ | t_R (min) | MS (M + H)⁺ |
|---|---|---|---|---|---|---|
| 2001 | H | 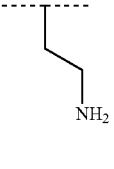 | 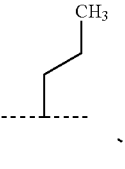 | Cl Cl | 6.2 | 390.1 |
| 2002 | 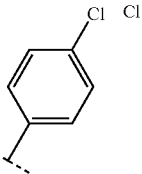 | 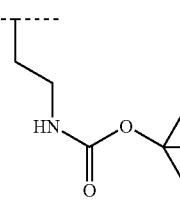 | 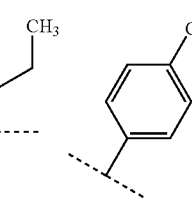 | Cl Cl | 5.2 | 433.1 |
| 2003 | 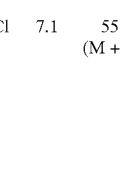 | | | Cl Cl | 7.1 | 555.1 (M + Na)⁺ |

TABLE 2-continued
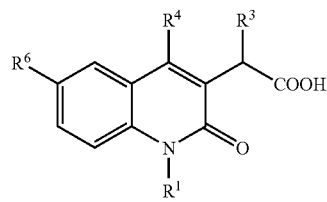
| Cpd | R¹ | R³ | R⁴ | R⁶ | $t_R$ (min) | MS $(M+H)^+$ |
|---|---|---|---|---|---|---|
| 2004 | H | CH₂=CH-CH₂-CH- | 4-Cl-C₆H₄ | Br | 5.9 | 434.0 |
| 2005 | H | CH₃-CH₂-CH₂-CH- | 4-Cl-C₆H₄ | H | 5.5 | 356.1 |
| 2006 | H | CH₃-CH₂-CH₂-CH- | 4-Cl-C₆H₄ | Br | 6.1 | 434.0 |
| 2007 | cyclopropyl-CH₂- | CH₃-CH₂-CH₂-CH- | 4-Cl-C₆H₄ | Cl | 6.9 | 444.0 |
| 2008 | MeO-CH₂-CH₂-CH₂- | CH₃-CH₂-CH₂-CH- | 4-Cl-C₆H₄ | Cl | 6.4 | 448.0 |
| 2009 | CH₃ | CH₃-CH₂-CH₂-CH- | 4-Cl-C₆H₄ | Cl | 6.5 | 404.1 |

TABLE 2-continued

[Structure: quinolinone with R⁶, R⁴, R³, COOH, N-R¹, =O]

| Cpd | R¹ | R³ | R⁴ | R⁶ | t_R (min) | MS (M + H)⁺ |
|---|---|---|---|---|---|---|
| 2010 | -CH(CH₃)CH₃ (isopropyl) | -CH(CH₃)CH₂— (butyl) | 4-Cl-C₆H₄— | Cl | 6.7 | 418.1 |
| 2011 | -CH₂-(4-pyridyl) | -CH(CH₃)CH₂— | 4-Cl-C₆H₄— | Cl | 5.4 | 480.9 |

TABLE 3

[Structure: coumarin with R⁶, R⁴, R³, COOH, O, =O]

| Cpd | R³ | R⁴ | R⁶ | t_R (min) | MS (M + H)⁺ |
|---|---|---|---|---|---|
| 3001 | -CH(CH₃)CH₂— | 4-Cl-C₆H₄— | Br | 8.1 | 435.0 |
| 3002 | -CH(CH=CH₂)CH₂— | 4-Cl-C₆H₄— | Br | 7.8 | 433.0 |
| 3003 | -CH(C(CH₃)=CH₂)CH₂— | 4-Cl-C₆H₄— | Br | 6.4 | 446.9 |

TABLE 3-continued

[Structure: coumarin with R⁶, R⁴, R³, COOH, O, =O]

| Cpd | R³ | R⁴ | R⁶ | t_R (min) | MS (M + H)⁺ |
|---|---|---|---|---|---|
| 3004 | -CH₂CH(CH₃)CH₃ (isobutyl) | 4-Cl-C₆H₄— | Br | 6.5 | 448.0 |

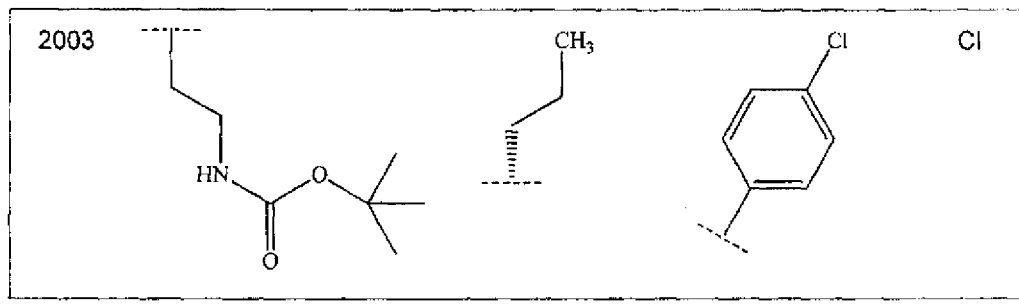

The invention claimed is:
1. A compound of the formula (I),

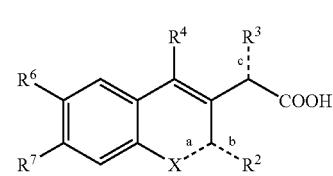

wherein:
bond a is a double bond and bond b is a single bond or
bond a is a single bond and bond b is a double bond;

X is NR$^1$ when bond a is a single bond;
or X is N when bond a is a double bond;

R$^1$ is H, (C$_{1-6}$)alkyl, (C$_{1-6}$)haloalkyl, (C$_{3-7}$)cycloalkyl-(C$_{1-6}$)alkyl-, aryl-(C$_{1-6}$)alkyl- or Het-(C$_{1-6}$)alkyl-;
wherein each of the (C$_{1-6}$)alkyl, (C$_{3-7}$)cycloalkyl-(C$_{1-6}$)alkyl-, aryl-(C$_{1-6}$)alkyl- and Het-(C$_{1-6}$)alkyl- is optionally substituted with —OH, —O(C$_{1-6}$)alkyl, —SH, —S(C$_{1-6}$)alkyl, —NH$_2$, —NH(C$_{1-6}$)alkyl or —N((C$_{1-6}$)alkyl)$_2$;

R$^2$ is H, (C$_{1-6}$)alkyl or —O(C$_{1-6}$)alkyl when bond b is a single bond;
or R$^2$ is O when bond b is a double bond;

R$^3$ is (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl-, Het-(C$_{1-6}$)alkyl- or —Y—R$^{31}$, and bond c is a single bond; or R$^3$ is (C$_{1-6}$)alkylidene and bond c is a double bond;
wherein Y is O or S and R$^{31}$ is (C$_{1-6}$)alkyl, (C$_{1-6}$)haloalkyl, (C$_{2-6}$)alkenyl, (C$_{2-6}$)alkynyl, (C$_{3-7}$)cycloalkyl, aryl, (C$_{3-7}$)cycloalkyl-(C$_{1-6}$)alkyl-, aryl-(C$_{1-6}$)alkyl- or Het-(C$_{1-6}$)alkyl-;
wherein each of the (C$_{1-6}$)alkylidene, (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl-, Het-(C$_{1-6}$)alkyl- and —Y—R$^{31}$ is optionally substituted with 1 to 3 substituents each independently selected from (C$_{1-6}$)alkyl, halo, cyano, oxo and —O(C$_{1-6}$)alkyl;

R$^4$ is aryl or Het, wherein each of the aryl and Het is optionally substituted with 1 to 5 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, cyano or oxo;

R$^6$ and R$^7$ are each independently selected from H, halo, (C$_{1-6}$)alkyl and (C$_{1-6}$)haloalkyl;

with the proviso that when
bond a is a single bond and bond b is a double bond; and
X is NR$^1$; R$^1$ is H; and R$^2$ is O; and
R$^4$ is unsubstituted phenyl; R$^6$ is Cl; R$^7$ is H; and
bond c is a double bond; then
R$^3$ is not =CH—CH(CH$_3$)$_2$; and wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;

or a salt, ester or tautomer thereof.

2. A compound according to claim 1, wherein X is NR$^1$ and bond a is a single bond.

3. A compound according to claim 1, wherein X is N and bond a is a double bond.

4. A compound according to claim 1 wherein R$^4$ is naphthyl or phenyl, wherein the phenyl is optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —O(C$_{1-4}$)alkyl, —SH, —S(C$_{1-4}$)alkyl, —NH$_2$, —NH(C$_{1-4}$)alkyl and —N((C$_{1-4}$)alkyl)$_2$; wherein the (C$_{1-4}$)alkyl is optionally substituted with hydroxy, cyano or oxo.

5. A compound according to claim 4, wherein R$^4$ is phenyl optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —O(C$_{1-4}$)alkyl, —SH, —S(C$_{1-4}$)alkyl, —NH$_2$, —NH(C$_{1-4}$)alkyl and —N((C$_{1-4}$)alkyl)$_2$; wherein the (C$_{1-4}$)alkyl is optionally substituted with hydroxy, cyano or oxo.

6. A compound according to claim 1, wherein R$^4$ is Het optionally substituted with 1 to 5 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, cyano or oxo.

7. A compound according to claim 6, wherein R$^4$ is Het optionally substituted with 1 to 3 substituents each independently selected from halo, (C$_{1-6}$)alkyl and —O(C$_{1-6}$)alkyl;
wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

8. A compound according to claim 1 of formula (Ia):

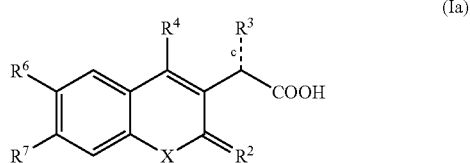

(Ia)

wherein
X is NR$^1$;
R$^1$ is H, (C$_{1-6}$)alkyl, (C$_{3-7}$)cycloalkyl-(C$_{1-6}$)alkyl-, or Het-(C$_{1-6}$)alkyl-;
wherein Het is a 4- to 7-membered heterocycle having 1 to 3 heteroatoms each independently selected from N, O and S;
and wherein each of the (C$_{1-6}$)alkyl, (C$_{3-7}$)cycloalkyl-(C$_{1-6}$)alkyl-, and Het-(C$_{1-6}$)alkyl- is optionally substituted with —OH, —O(C$_{1-3}$)alkyl, —NH$_2$, —NH(C$_{1-3}$)alkyl or —N((C$_{1-3}$)alkyl)$_2$;

R$^2$ is O;
R$^3$ is (C$_{1-6}$)alkyl or (C$_{2-6}$)alkenyl; and
bond c is a single bond;
R$^4$ is naphthyl or phenyl, wherein the phenyl is optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —O(C$_{1-4}$)alkyl, —SH, —S(C$_{1-4}$)alkyl, —NH$_2$, —NH(C$_{1-4}$)alkyl and —N((C$_{1-4}$)alkyl)$_2$; wherein the (C$_{1-4}$)alkyl is optionally substituted with hydroxy, cyano or oxo;

R$^6$ is H, halo, (C$_{1-3}$)alkyl or (C$_{1-3}$)haloalkyl;
R$^7$ is H or F;
or a salt or ester thereof.

9. A compound according to claim 8, wherein R$^4$ is phenyl optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —O(C$_{1-4}$)alkyl, —SH, —S(C$_{1-4}$)alkyl, —NH$_2$, —NH(C$_{1-4}$)alkyl and —N((C$_{1-4}$)alkyl)$_2$; wherein the (C$_{1-4}$)alkyl is optionally substituted with hydroxy, cyano or oxo.

10. A compound according to claim 8, wherein R$^4$ is a group of formula:

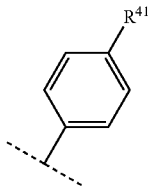

wherein $R^{41}$ is selected from halo, $(C_{1-4})$alkyl and $(C_{1-4})$haloalkyl.

11. A compound according to claim 9, wherein $R^6$ is H, Cl or Br and $R^7$ is H.

12. A compound according to claim 1 of formula (Id):

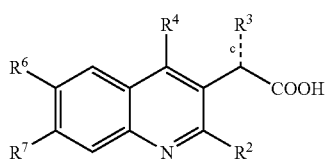

(Id)

wherein $R^2$ is $(C_{1-6})$alkyl or $-O(C_{1-6})$alkyl;

$R^3$ is $(C_{1-6})$alkyl, $(C_{2-6})$alkenyl, $-O-(C_{1-6})$alkyl, $-O-(C_{1-6})$haloalkyl, $-O-(C_{2-6})$alkenyl, $-O-(C_{2-6})$alkynyl, $-O-(C_{3-7})$cycloalkyl, $-O$-aryl, $(C_{3-7})$cycloalkyl-$(C_{1-6})$alkyl-$O-$, aryl-$(C_{1-6})$alkyl-$O-$ or Het-$(C_{1-6})$alkyl-$O-$;
  wherein each of the $-O-(C_{1-6})$alkyl, $-O-(C_{2-6})$alkenyl, $-O-(C_{2-6})$alkynyl, $-O-(C_{3-7})$cycloalkyl, $-O$-aryl, $(C_{3-7})$cycloalkyl-$(C_{1-6})$alkyl-$O-$, aryl-$(C_{1-6})$alkyl-$O-$ and Het-$(C_{1-6})$alkyl-$O-$ is optionally substituted with 1 to 3 substituents each independently selected from $(C_{1-6})$alkyl, halo, cyano, oxo and $-O(C_{1-6})$alkyl; and
  bond c is a single bond; or $R^3$ is $(C_{1-6})$alkylidene and bond c is a double bond;

$R^4$ is naphthyl or phenyl, wherein the phenyl is optionally substituted with 1 to 3 substituents each independently selected from halo, $(C_{1-4})$alkyl, $(C_{2-4})$alkenyl, $(C_{1-4})$haloalkyl, $(C_{3-7})$cycloalkyl, $-OH$, $-O(C_{1-4})$alkyl, $-SH$, $-S(C_{1-4})$alkyl, $-NH_2$, $-NH(C_{1-4})$alkyl and $-N((C_{1-4})$alkyl$)_2$; wherein the $(C_{1-4})$alkyl is optionally substituted with hydroxy, cyano or oxo; or $R^4$ is Het optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, $-OH$, $-O(C_{1-6})$alkyl, $-SH$, $-S(C_{1-6})$alkyl, $-NH_2$, $-NH(C_{1-6})$alkyl and $-N((C_{1-6})$alkyl$)_2$; wherein the $(C_{1-6})$alkyl is optionally substituted with hydroxy, cyano or oxo;

$R^6$ is H, halo, $(C_{1-3})$alkyl or $(C_{1-3})$haloalkyl; and $R^7$ is H or F;

or a salt or ester thereof.

13. A compound according to claim 12, wherein $R^7$ is H and $R^6$ is H, Cl or Br.

14. A compound according to claim 12, wherein $R^2$ is $(C_{1-6})$alkyl.

15. A compound according to claim 14, wherein $R^2$ is $CH_3$.

16. A compound according to claim 12, wherein $R^3$ is $-O-(C_{1-6})$alkyl, $-O-(C_{1-6})$haloalkyl, $-O-(C_{2-6})$alkenyl, $-O-(C_{2-6})$alkynyl, $-O-(C_{3-7})$cycloalkyl, $-O$-aryl, $(C_{3-7})$cycloalkyl-$(C_{1-6})$alkyl-$O-$, aryl-$(C_{1-6})$alkyl-$O-$ or Het-$(C_{1-6})$alkyl-$O-$;
  wherein each of the $-O-(C_{1-6})$alkyl, $-O-(C_{2-6})$alkenyl, $-O-(C_{2-6})$alkynyl, $-O-(C_{3-7})$cycloalkyl, $-O$-aryl, $(C_{3-7})$cycloalkyl-$(C_{1-6})$alkyl-$O-$, aryl-$(C_{1-6})$alkyl-$O-$ and Het$(C_{1-6})$alkyl-$O-$ is optionally substituted with 1 to 3 substituents each independently selected from $(C_{1-6})$alkyl, halo, cyano, oxo and $-O(C_{1-6})$alkyl; and
  bond c is a single bond.

17. A compound according to claim 12, wherein $R^4$ is phenyl optionally substituted with 1 to 3 substituents each independently selected from halo, $(C_{1-4})$alkyl, $(C_{2-4})$alkenyl, $(C_{1-4})$haloalkyl, $(C_{3-7})$cycloalkyl, $-OH$, $-O(C_{1-4})$alkyl, $-SH$, $-S(C_{1-4})$alkyl, $-NH_2$, $-NH(C_{1-4})$alkyl and $-N((C_{1-4})$alkyl$)_2$; wherein the $(C_{1-4})$alkyl is optionally substituted with hydroxy, cyano or oxo.

18. A compound according to claim 12, wherein $R^4$ is Het optionally substituted with 1 to 3 substituents each independently selected from halo, $(C_{1-6})$alkyl and $-O(C_{1-6})$alkyl;
  wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

19. A compound according to claim 1 of the formula:

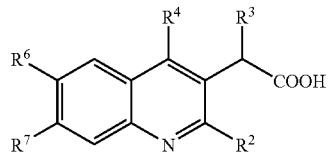

wherein $R^2$, $R^3$, $R^4$, $R^6$ and $R^7$ are defined according to the following table:

| Cpd | $R^2$ | $R^3$ | $R^4$ | $R^6$ | $R^7$ |
|---|---|---|---|---|---|
| 1001 | $CH_3$ | $O-CH_3$ | $\text{4-Cl-phenyl}$ | Br | H |

-continued
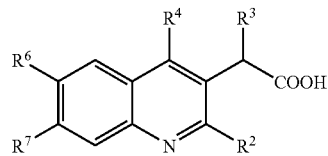
wherein R², R³, R⁴, R⁶ and R⁷ are defined according to the following table:
| Cpd | R² | R³ | R⁴ | R⁶ | R⁷ |
|---|---|---|---|---|---|
| 1002 | $CH_3$ | -O-propyl | 4-Cl-phenyl | Br | H |
| 1003 | $CH_3$ | -O-$CH_3$ | 4-Cl-phenyl | Br | H |
| 1004 | $CH_3$ | -$CH_2$-CH=$CH_2$ | 4-Cl-phenyl | Br | H |
| 1005 | $CH_3$ | -O-$CH_3$ | 4-$CF_3$-phenyl | Cl | H |
| 1006 | $CH_3$ | -O-ethyl | 4-Cl-phenyl | Br | H |
| 1007 | $CH_3$ | -CH=CH-$CH_3$ | 4-Cl-phenyl | Br | H |
| 1008 | $CH_3$ | -propyl | 4-Br-phenyl | Cl | H |

-continued
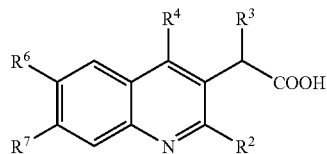
wherein R², R³, R⁴, R⁶ and R⁷ are defined according to the following table:
| Cpd | R² | R³ | R⁴ | R⁶ | R⁷ |
|---|---|---|---|---|---|
| 1009 | —OCH₃ | —CH(CH₃)CH₂CH₃ | 4-chlorophenyl | Br | H |
| 1010 | —CH(CH₃)₂ | —CH(CH₃)CH₂CH₃ | 4-chlorophenyl | Br | H |
| 1011 | CH₃ | —CH(OCH₃)— | 4-chlorophenyl | H | H |
| 1012 | CH₃ | —CH(CH₃)CH₂CH₃ | naphthalen-2-yl | Cl | H |
| 1013 | CH₃ | —CH(CH₃)CH₂CH₃ | 4-methylphenyl | Cl | H |
| 1014 | CH₃ | —CH(CH₃)CH₂CH₃ | 3-fluoro-4-methylphenyl | Cl | H |
| 1015 | CH₃ | —CH(OCH₃)— | 1-methyl-1H-indol-6-yl | Cl | H |

-continued
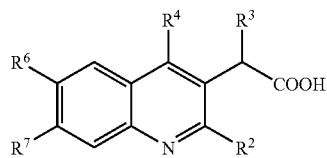
wherein R², R³, R⁴, R⁶ and R⁷ are defined according to the following table:
| Cpd | R² | R³ | R⁴ | R⁶ | R⁷ |
|---|---|---|---|---|---|
| 1016 | CH₃ | OCH₃ | 2,3-dihydrobenzofuran-5-yl | Cl | H |
| 1017 | CH₃ | OCH₃ | 4-methoxyphenyl | Cl | H |
| 1018 | CH₃ | n-butyl | 2,4-dimethylphenyl | Cl | H |
| 1019 | CH₃ | OCH₃ | 1H-indol-6-yl | Cl | H |
| 1020 | CH₃ | (5-methylisoxazol-3-yl)methoxy | 4-chlorophenyl | Br | H |
| 1021 | CH₃ | OCH₃ | benzofuran-5-yl | Cl | H |
| 1022 | CH₃ | (2-methylallyl)oxy | 4-chlorophenyl | Br | H |

-continued
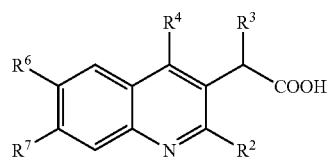
wherein R², R³, R⁴, R⁶ and R⁷ are defined according to the following table:
| Cpd | R² | R³ | R⁴ | R⁶ | R⁷ |
|---|---|---|---|---|---|
| 1023 | CH₃ | (1-pyrrolyl)propyl-O- | 4-chlorophenyl | Br | H |
| 1024 | CH₃ | CH₃O- | 4-methylphenyl | Cl | H |
| 1025 | CH₃ | isopropyl-O- | 4-chlorophenyl | Br | H |
| 1026 | CH₃ | cyclopropylmethyl-O- | 4-chlorophenyl | Br | H |
| 1027 | CH₃ | (5-methylisoxazol-3-yl)methyl-O- | 4-methylphenyl | Br | H |
| 1028 | CH₃ | allyl-O- | 4-chlorophenyl | Br | H |

-continued
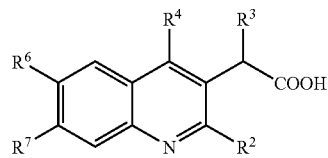
wherein $R^2$, $R^3$, $R^4$, $R^6$ and $R^7$ are defined according to the following table:
| Cpd | $R^2$ | $R^3$ | $R^4$ | $R^6$ | $R^7$ |
|---|---|---|---|---|---|
| 1029 | $CH_3$ | –O–$CH_3$ | 4-Cl-phenyl | Cl | H |
| 1030 | $CH_3$ | $CH_2CH_3$ | 4-F-phenyl | Cl | H |
| 1031 | $CH_3$ | $CH_2CH_3$ | phenyl | Cl | H |
| 1032 | $CH_3$ | $CH_2CH_3$ | 4-$CH_3$-phenyl | Br | H |
| 1033 | $CH_3$ | $CH_2CH_3$ | 4-$CH_3$-phenyl | H | H |
| 1034 | $CH_3$ | $CH_2CH_3$ | 4-(CH=$CH_2$)-phenyl | Cl | H |
| 1035 | $CH_3$ | $CH_2CH(CH_3)_2$ | 4-Cl-phenyl | Br | H |

-continued
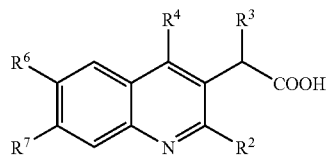
wherein R², R³, R⁴, R⁶ and R⁷ are defined according to the following table:
| Cpd | R² | R³ | R⁴ | R⁶ | R⁷ |
|---|---|---|---|---|---|
| 1036 | $CH_3$ | n-propyl | 4-methoxyphenyl | Cl | H |
| 1037 | $CH_3$ | n-propyl | 4-cyclopropylphenyl | Cl | H |
| 1038 | $CH_3$ | -OCH$_2$CN | 4-chlorophenyl | Br | H |
| 1039 | $CH_3$ | -OCH$_2$CH=CHCH$_3$ | 4-chlorophenyl | Br | H |
| 1040 | $CH_3$ | -OCH$_2$CH=C(CH$_3$)$_2$ | 4-chlorophenyl | Br | H |
| 1041 | $CH_3$ | -OCH$_2$C≡CH | 4-chlorophenyl | Br | H |

-continued
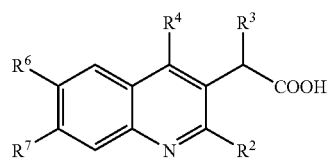
wherein R², R³, R⁴, R⁶ and R⁷ are defined according to the following table:
| Cpd | R² | R³ | R⁴ | R⁶ | R⁷ |
|---|---|---|---|---|---|
| 1042 | $CH_3$ | propargyloxy (-O-CH₂-C≡C-CH₃) | 4-Cl-phenyl | Br | H |
| 1043 | $CH_3$ | -O-CH₂-CH₃ | 4-Cl-phenyl | Br | H |
| 1044 | $CH_3$ | -O-CH₂-CH₂-CH₃ | 4-Cl-phenyl | Br | H |
| 1045 | $CH_3$ | -O-CH₂-CH₂-OMe | 4-Cl-phenyl | Br | H |
| 1046 | $CH_3$ | -O-CH₂-CH₂-CH(CH₃)₂ | 4-Cl-phenyl | Br | H |
| 1047 | $CH_3$ | -O-CH₂-CH₂-CH₂-CH₂-CH₃ | 4-Cl-phenyl | Br | H |

-continued
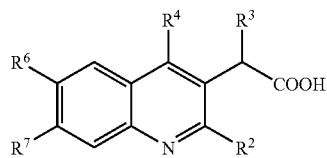
wherein R², R³, R⁴, R⁶ and R⁷ are defined according to the following table:
| Cpd | R² | R³ | R⁴ | R⁶ | R⁷ |
|---|---|---|---|---|---|
| 1048 | CH₃ | -O-CH₂CH₂CH₂-CN | 4-Cl-C₆H₄- | Br | H |
| 1049 | CH₃ | -O-CH(CH₃)-CN (R) | 4-Cl-C₆H₄- | Br | H |
| 1050 | CH₃ | -O-CH(CH₃)-C(O)-CH₃ (R) | 4-Cl-C₆H₄- | Br | H |
| 1051 | CH₃ | -O-CH(CH₃)-CN (S) | 4-Cl-C₆H₄- | Br | H |
| 1052 | CH₃ | -O-CH(CH₃)-C(O)-CH₃ (S) | 4-Cl-C₆H₄- | Br | H |
| 1053 | CH₃ | -CH₂CH₂-CH₃ | 4-CH₃-C₆H₄- | F | F |
| 1054 | CH₃ | -CH₂CH₂-CH₃ | 4-CH₃-C₆H₄- | Cl | H |

-continued
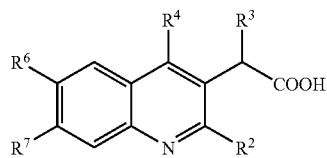
wherein R², R³, R⁴, R⁶ and R⁷ are defined according to the following table:
| Cpd | R² | R³ | R⁴ | R⁶ | R⁷ |
|---|---|---|---|---|---|
| 1055 | CH₃ | CH(CH₃)OCH(CH₃) (S) | 4-Cl-phenyl | Br | H |
| 1056 | CH₃ | CH₂CH=CH₂ | 4-Cl-phenyl | Cl | H |
| 1057 | CH₃ | CH(CH₃)OCH(CH₃) | 4-CH₃-phenyl | Cl | H |
| 1058 | CH₃ | CH(CH₃)OCH₂CH₃ | 4-CH₃-phenyl | Cl | H |
| 1059 | CH₃ | CH(CH₃)OCH(CH₃) | 4-OMe-phenyl | Cl | H |
| 1060 | CH₃ | CH(CH₃)OCH₂CH₃ | 4-OMe-phenyl | Cl | H |
| 1061 | CH₃ | CH(CH₃)OCH₂CH₃ (S) | 4-CH₃-phenyl | Cl | H |

-continued
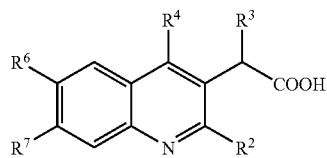
wherein R², R³, R⁴, R⁶ and R⁷ are defined according to the following table:
| Cpd | R² | R³ | R⁴ | R⁶ | R⁷ |
|---|---|---|---|---|---|
| 1062 | CH₃ | —CH(OiPr)CH₃ | 4-(CH₃)C₆H₄CH₂— | Cl | H |
| 1063 | CH₃ | n-propyl | 4-Cl-C₆H₄— | Cl | H |
| 1064 | CH₃ | n-propyl | 3-Cl-4-F-C₆H₃— | Cl | H |
| 1065 | CH₃ | n-propyl | 3-Cl-C₆H₄— | Cl | H |
| 1066 | CH₃ | n-propyl | 3-MeO-C₆H₄— | Cl | H |
| 1067 | CH₃ | n-propyl | benzofuran-2-yl | Cl | H |
| 1068 | CH₃ | n-propyl | 5-Cl-thiophen-2-yl | Cl | H |

-continued
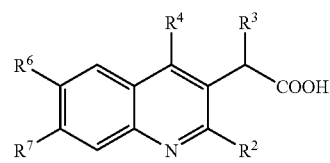
wherein R², R³, R⁴, R⁶ and R⁷ are defined according to the following table:
| Cpd | R² | R³ | R⁴ | R⁶ | R⁷ |
|---|---|---|---|---|---|
| 1069 | CH₃ | CH₃-CH₂-CH₂- | 4-Cl-3-CH₃-phenyl | Cl | H |
| 1070 | CH₃ | CH₃-CH₂-CH₂- | 4-OMe-3-CH₃... wait | Cl | H |
| 1071 | CH₃ | CH₃-CH₂-CH₂- | 1-methylindol-5-yl | Cl | H |
| 1072 | CH₃ | CH₃-CH₂-CH₂- | 3-Cl-4-CH₃-phenyl | Cl | H |
| 1073 | CH₃ | CH₃-O-CH₂-CH(−)− (ethoxymethyl) | 4-OMe-phenyl | Cl | H |
| 1074 | CH₃ | (CH₃)₂CH-O-CH(CH₃)- | 4-OMe-phenyl | Cl | H |

-continued
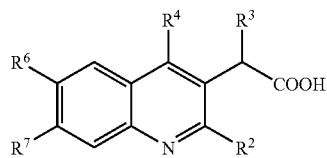
wherein R², R³, R⁴, R⁶ and R⁷ are defined according to the following table:
| Cpd | R² | R³ | R⁴ | R⁶ | R⁷ |
|---|---|---|---|---|---|
| 1075 | CH₃ | n-butyl | 4-(SCH₃)-phenyl | Cl | H |
| 1076 | CH₃ | n-butyl | 2-thienyl | Cl | H |
| 1077 | CH₃ | n-butyl | 3,4-difluorophenyl | Cl | H |
| 1078 | CH₃ | OC(CH₃)₃ | 4-methylphenyl | Cl | H |
| 1079 | CH₃ | OC(CH₃)₃ | 4-chlorophenyl | Br | H |
| 1080 | CH₃ | OCH₂CH₃ | 4-chlorophenyl | Cl | H |
| 1081 | CH₃ | OCH(CH₃)₂ | 4-acetylphenyl | Cl | H |

-continued
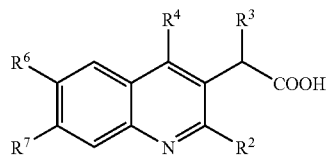
wherein R², R³, R⁴, R⁶ and R⁷ are defined according to the following table:
| Cpd | R² | R³ | R⁴ | R⁶ | R⁷ |
|---|---|---|---|---|---|
| 1082 | CH₃ | —OCH(CH₃)₂ | 4-chlorophenyl | H | H |
| 1083 | CH₃ | —OCH(CF₃)₂ | 4-methylphenyl | Cl | H |
| 1084 | CH₃ | —OC₆H₅ | 4-methylphenyl | Cl | H |
| 1085 | CH₃ | —OC(CH₃)₂CH₂CH₃ | 4-methylphenyl | Cl | H |
| 1086 | CH₃ | —O-(1-methylcyclopentyl) | 4-methylphenyl | Cl | H |
| 1087 | CH₃ | —OCH(CH₃)₂ | 4-(N,N-dimethylamino)phenyl | Cl | H |

-continued
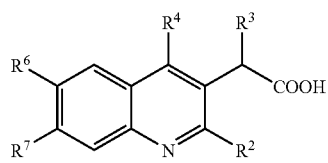
wherein $R^2$, $R^3$, $R^4$, $R^6$ and $R^7$ are defined according to the following table:
| Cpd | $R^2$ | $R^3$ | $R^4$ | $R^6$ | $R^7$ |
|---|---|---|---|---|---|
| 1088 | $CH_3$ | isopropoxy | quinolin-6-yl | Cl | H |
| 1089 | $CH_3$ | tert-butoxy | 4-methylbenzyl | Cl | H |
| 1090 | $CH_3$ | (1-methylcyclohexyl)methyl | 4-methylbenzyl | Cl | H |
| 1091 | $CH_3$ | cyclobutoxy | 4-methylbenzyl | Cl | H |
| 1092 | $CH_3$ | cyclopentyloxy | 4-methylbenzyl | Cl | H |
| 1093 | $CH_3$ | isopropoxy | 4-(1,1-difluoroethyl)benzyl | Cl | H |

-continued

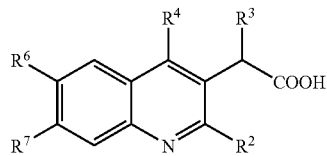

wherein R², R³, R⁴, R⁶ and R⁷ are defined according to the following table:

| Cpd | R² | R³ | R⁴ | R⁶ | R⁷ |
|---|---|---|---|---|---|
| 1094 | CH₃ | 1-(ethyl)cyclopropyl-O- | 4-methylbenzyl | Cl | H |
| 1095 | CH₃ | 1-methylcyclobutyl-O- | 4-methylbenzyl | Cl | H |
| 1096 | CH₃ | 1-methylcyclopropyl-O- | 4-methylbenzyl | Cl | H |
| 1097 | CH₃ | pentan-3-yl-O- | 4-methylbenzyl | Cl | H |
| 1098 | CH₃ | isopropyl-O- | 4-ethoxybenzyl | Cl | H |
| 1099 | CH₃ | (S)-butan-2-yl-O- | 4-methylbenzyl | Cl | H |
| 1100 | CH₃ | isopropyl-O- | benzo[1,3]dioxol-5-ylmethyl | Cl | H |

-continued
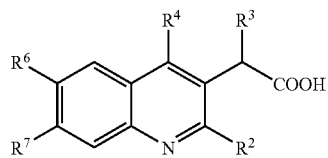
wherein R², R³, R⁴, R⁶ and R⁷ are defined according to the following table:
| Cpd | R² | R³ | R⁴ | R⁶ | R⁷ |
|---|---|---|---|---|---|
| 1101 | —CH₂CH₃ | -CH(CH₃)CH₂CH₃ | 4-Cl-C₆H₄- | Cl | H |
| 1102 | CH₃ | -O-CH(CH₃)CH₂CH₃ (S) | 4-CH₃-C₆H₄- | Cl | H |
| 1103 | CH₃ | -O-C(CF₃)(CH₃)₂ | 4-CH₃-C₆H₄- | Cl | H |
| 1104 | CH₃ | -O-C(CH₂F)(CH₂F)(CH₃) | 4-CH₃-C₆H₄- | Cl | H |
| 1105 | CH₃ | -O-C(cyclobutyl)(CH₂CH₃) | 4-CH₃-C₆H₄- | Cl | H |
| 1106 | CH₃ | -O-C(CH₃)₃ | 4-Cl-C₆H₄- | Br | H |
| 1107 | CH₃ | -O-C(CH₂Cl)(CH₃)₂ | 4-CH₃-C₆H₄- | Cl | H |

-continued

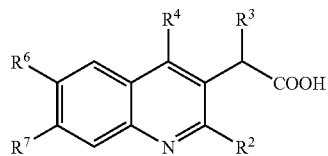

wherein $R^2$, $R^3$, $R^4$, $R^6$ and $R^7$ are defined according to the following table:

| Cpd | $R^2$ | $R^3$ | $R^4$ | $R^6$ | $R^7$ |
|---|---|---|---|---|---|
| 1108 | CH₃ | ...CH₃, CH₃, O, CH₃ (3-methyl-3-methoxypentyl) | 4-methylbenzyl | Cl | H |
| 1109 | CH₃ | isopropoxy (O-CH(CH₃)₂) | phenyl | Cl | H |
| 1110 | CH₃ | isopropoxy | 4-bromophenyl | Cl | H |
| 1111 | CH₃ | isopropoxy | naphth-1-yl | Cl | H |
| 1112 | CH₃ | isopropoxy | 4-chlorophenyl | Cl | H |
| 1113 | CH₃ | isopropoxy | 4-methylphenyl | Cl | H |
| 1114 | CH₃ | isopropoxy | 3-methylphenyl | Cl | H |

-continued
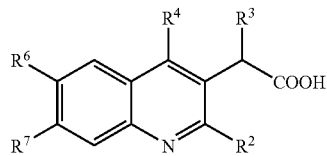
wherein R², R³, R⁴, R⁶ and R⁷ are defined according to the following table:
| Cpd | R² | R³ | R⁴ | R⁶ | R⁷ |
|---|---|---|---|---|---|
| 1115 | $CH_3$ | $CH(CH_3)OCH_3$ ... | 4-($SCH_3$)phenyl | Cl | H |
| 1116 | $CH_3$ | $CH(CH_3)OCH_3$ ... | 2-($CH_3$)phenyl | Cl | H |
| 1117 | $CH_3$ | $CH(CH_3)OCH_3$ ... | thien-2-yl | Cl | H |
| 1118 | $CH_3$ | $CH(CH_3)OCH_3$ ... | thien-3-yl | Cl | H |
| 1119 | $CH_3$ | $CH(CH_3)OCH_3$ ... | 4-($CF_3$)phenyl | Cl | H |
| 1120 | $CH_3$ | $CH(CH_3)OCH_3$ ... | 3-F-phenyl | Cl | H |
| 1121 | $CH_3$ | $CH(CH_3)OCH_3$ ... | 3-methylthien-2-yl | Cl | H |
| 1122 | $CH_3$ | $CH(CH_3)OCH_3$ ... | 4-(vinyl)phenyl | Cl | H |

-continued
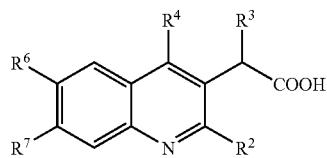
wherein R², R³, R⁴, R⁶ and R⁷ are defined according to the following table:
| Cpd | R² | R³ | R⁴ | R⁶ | R⁷ |
|---|---|---|---|---|---|
| 1123 | $CH_3$ | —OCH($CH_3$)$_2$ | pyridin-3-yl | Cl | H |
| 1124 | $CH_3$ | —OCH($CH_3$)$_2$ | 4-(hydroxymethyl)phenyl | Cl | H |
| 1125 | $CH_3$ | —OCH($CH_3$)$_2$ | 3-fluoro-4-methoxyphenyl | Cl | H |
| 1126 | $CH_3$ | —OCH($CH_3$)$_2$ | 4-ethylphenyl | Cl | H |
| 1127 | $CH_3$ | —OCH($CH_3$)$_2$ | 2,3-dimethylphenyl | Cl | H |
| 1128 | $CH_3$ | —OCH($CH_3$)$_2$ | 2,3-dihydro-1,4-benzodioxin-6-yl | Cl | H |

-continued
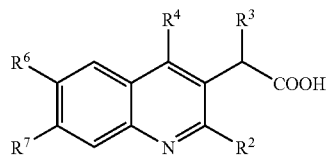
wherein R², R³, R⁴, R⁶ and R⁷ are defined according to the following table:
| Cpd | R² | R³ | R⁴ | R⁶ | R⁷ |
|---|---|---|---|---|---|
| 1129 | CH₃ | -O-CH(CH₃)₂ | 4-(C(CH₃)₃)-C₆H₄- | Cl | H |
| 1130 | CH₃ | -O-CH(CH₃)₂ | 3,4-(MeO)₂-C₆H₃- | Cl | H |
| 1131 | CH₃ | -O-CH(CH₃)₂ | 4-(CH(CH₃)₂)-C₆H₄- | Cl | H |
| 1132 | CH₃ | -O-CH(CH₃)₂ | 4-OH-C₆H₄- | Cl | H |
| 1133 | CH₃ | -O-CH(CH₃)₂ | benzo[b]thiophen-2-yl | Cl | H |
| 1134 | CH₃ | -O-CH(CH₃)₂ | benzo[b]thiophen-3-yl | Cl | H |

-continued
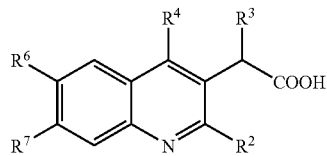
wherein R², R³, R⁴, R⁶ and R⁷ are defined according to the following table:
| Cpd | R² | R³ | R⁴ | R⁶ | R⁷ |
|---|---|---|---|---|---|
| 1135 | CH₃ | –O–CH(CH₃)₂ | 6-methoxypyridin-3-yl | Cl | H |
| 1136 | CH₃ | –O–CH(CH₃)₂ | 3-methyl-4-methoxyphenyl | Cl | H |
| 1137 | CH₃ | –O–CH(CH₃)₂ | quinolin-3-yl | Cl | H |
| 1138 | CH₃ | –O–CH(CH₃)₂ | 3,4-dimethylphenyl (2,5-dimethylphenyl) | Cl | H |
| 1139 | CH₃ | –O–CH(CH₃)₂ | 3-methyl-4-chlorophenyl | Cl | H |
| 1140 | CH₃ | –O–CH(CH₃)₂ | 3-methyl-4-chlorophenyl | Cl | H |
| 1141 | CH₃ | –O–CH(CH₃)₂ | pyrimidin-5-yl | Cl | H |

-continued
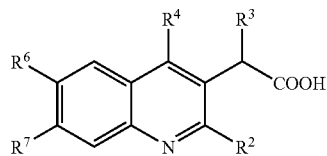
wherein R², R³, R⁴, R⁶ and R⁷ are defined according to the following table:
| Cpd | R² | R³ | R⁴ | R⁶ | R⁷ |
|---|---|---|---|---|---|
| 1142 | $CH_3$ | -O-CH(CH₃)₂ | 2-methoxypyrimidin-5-yl | Cl | H |
| 1143 | $CH_3$ | -O-CH(CH₃)₂ | 6-chloropyridin-3-yl | Cl | H |
| 1144 | $CH_3$ | -O-CH(CH₃)₂ | 1H-indol-6-yl | Cl | H |
| 1145 | $CH_3$ | -O-CH(CH₃)₂ | 2-fluoro-4-methoxyphenyl | Cl | H |
| 1146 | $CH_3$ | -O-CH(CH₃)₂ | 4-methylthiophen-3-yl | Cl | H |
| 1147 | $CH_3$ | -O-CH(CH₃)₂ | 3-fluoro-4-ethoxyphenyl | Cl | H |
| 1148 | $CH_3$ | -O-CH(CH₃)₂ | 2-chlorothiophen-3-yl | Cl | H |

-continued
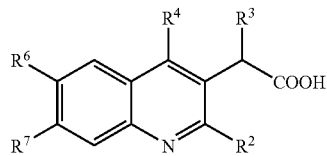
wherein R², R³, R⁴, R⁶ and R⁷ are defined according to the following table:
| Cpd | R² | R³ | R⁴ | R⁶ | R⁷ |
|---|---|---|---|---|---|
| 1149 | $CH_3$ | $-O-CH(CH_3)_2$ | 6-methylpyridin-3-yl | Cl | H |
| 1150 | $CH_3$ | $-O-CH(CH_3)_2$ | 4-ethoxy-3-methylphenyl | Cl | H |
| 1151 | $CH_3$ | $-O-CH(CH_3)_2$ | 2-hydroxyphenyl | Cl | H |
| 1152 | $CH_3$ | $-O-CH(CH_3)_2$ | 2-hydroxyphenyl | H | H |
| 1153 | $CH_3$ | $-O-CH(CH_3)_2$ | 3-hydroxyphenyl | Cl | H |
| 1154 | $CH_3$ | $-O-CH(CH_3)_2$ | 3-hydroxyphenyl | H | H |
| 1155 | $CH_3$ | $-O-C(CH_3)_3$ | 4-(2-fluoroethyl)phenyl | Cl | H |

-continued
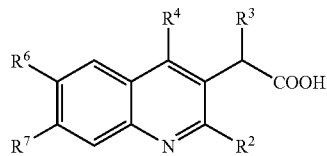
wherein $R^2$, $R^3$, $R^4$, $R^6$ and $R^7$ are defined according to the following table:
| Cpd | $R^2$ | $R^3$ | $R^4$ | $R^6$ | $R^7$ |
|---|---|---|---|---|---|
| 1156 | $CH_3$ | —OC($CH_3$)$_3$ | 4-(2-fluoroethyl)phenyl | Cl | H |
| 1157 | $CH_3$ | —OC($CH_3$)$_3$ | 4-methyl-3-methylphenyl | H | H |
| 1158 | $CH_3$ | —OC($CH_3$)$_3$ | 4-chlorophenyl | H | H |
| 1159 | $CH_3$ | —OC($CH_3$)$_3$ | 4-methyl-3-methylphenyl | H | H |
| 1160 | $CH_3$ | —OC($CH_3$)$_3$ | 4-chlorophenyl | H | H |
| 1161 | $CH_3$ | —OCH($CH_3$)$_2$ | 4-methylphenyl | H | H |

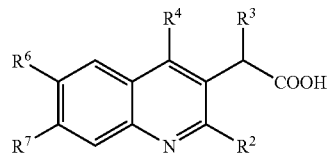
wherein $R^2$, $R^3$, $R^4$, $R^6$ and $R^7$ are defined according to the following table:
| Cpd | $R^2$ | $R^3$ | $R^4$ | $R^6$ | $R^7$ |
|---|---|---|---|---|---|
| 1162 | CH$_3$ | | | Cl | H |
| | | 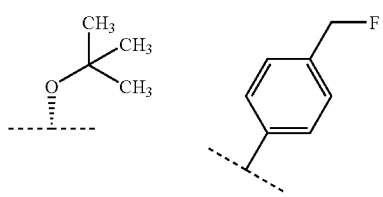 | | | |
| 1163 | CH$_3$ | | | H | H |
| 1164 | CH$_3$ | 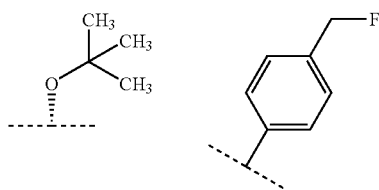 | | Br | H |
| 1165 | CH$_3$ | 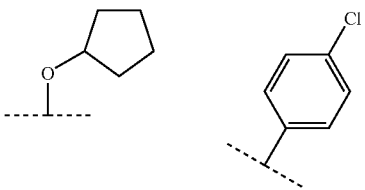 | | Cl | H |
| 1166 | CH$_3$ | 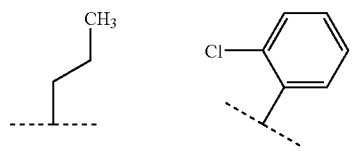 | | Cl | H. |
| | | 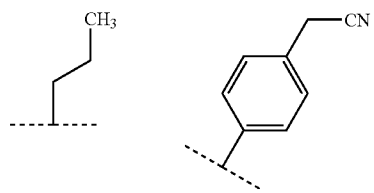 | | | |

20. A compound according to claim 1 of the formula:

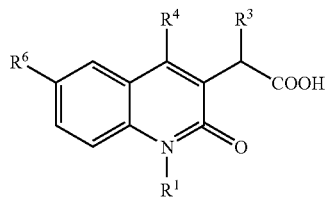

wherein $R^1$, $R^3$, $R^4$ and $R^6$ are defined according to the following table:

| Cpd | $R^1$ | $R^3$ | $R^4$ | $R^6$ |
|---|---|---|---|---|
| 2001 | H | propyl | 4-Cl-phenyl | Cl |
| 2002 | aminopropyl | propyl | 4-Cl-phenyl | Cl |
| 2003 | Boc-NH-propyl | propyl | 4-Cl-phenyl | Cl |
| 2004 | H | allyl | 4-Cl-phenyl | Br |
| 2005 | H | propyl | 4-Cl-phenyl | H |
| 2006 | H | propyl | 4-Cl-phenyl | Br |
| 2007 | cyclopropylmethyl | propyl | 4-Cl-phenyl | Cl |
| 2008 | methoxyethyl | propyl | 4-Cl-phenyl | Cl |
| 2009 | $CH_3$ | propyl | 4-Cl-phenyl | Cl |
| 2010 | isobutyl | propyl | 4-Cl-phenyl | Cl |
| 2011 | (pyridin-4-yl)methyl | propyl | 4-Cl-phenyl | Cl |

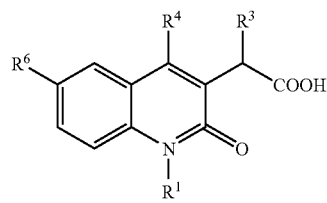

wherein $R^1$, $R^3$, $R^4$ and $R^6$ are defined according to the following table:

21. A pharmaceutical composition comprising a therapeutically effective amount of a compound of formula (I) as defined in claim 1, or a pharmaceutically acceptable salt or ester thereof; and one or more pharmaceutically acceptable carriers.

22. The pharmaceutical composition as defined in claim 21 additionally comprising at least one other antiviral agent.

23. The pharmaceutical composition as defined in claim 22 wherein the at least one antiviral agent comprises at least one NNRTI.

24. The pharmaceutical composition as defined in claim 22, wherein the at least one antiviral agent comprises at least one NRTI.

25. The pharmaceutical composition as defined in claim 22, wherein the at least one antiviral agent comprises at least one protease inhibitor.

26. The pharmaceutical composition as defined in claim 22, wherein the at least one antiviral agent comprises at least one entry inhibitor.

27. The pharmaceutical composition as defined in claim 22, wherein the at least one antiviral agent comprises at least one integrase inhibitor.

28. A method of treating an HIV infection in an infected human, the method comprising administering a therapeutically effective amount of a compound of formula (I) as defined in claim 1.

29. The method of claim 28, wherein there is also administered at least one other antiviral agent.

30. A method of inhibiting the replication of HIV comprising exposing the virus to an effective amount of the compound of formula (I) as defined in claim 1, or a salt or ester thereof, under conditions where replication of HIV is inhibited.

* * * * *

UNITED STATES PATENT AND TRADEMARK OFFICE
CERTIFICATE OF CORRECTION

PATENT NO. : 7,939,545 B2
APPLICATION NO. : 11/746303
DATED : May 10, 2011
INVENTOR(S) : Youla S. Tsantrizos et al.

It is certified that error appears in the above-identified patent and that said Letters Patent is hereby corrected as shown below:

Column 122
Claim 10, line 66, "claim 8" should read -- claim 9 --.

Column 123
Claim 11, line 13, "claim 9" should read -- claim 8 --.

Column 125

Claim 19, lines 43–48, compound 1006, " 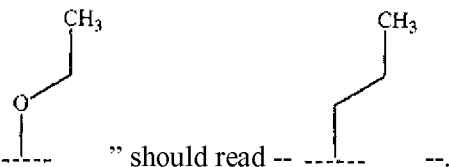 " should read -- --.

Column 151

Claim 19, lines 23–27, compound 1089, " 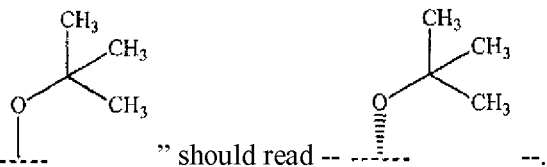 " should read -- --.

Claim 19, lines 31–36, compound 1090, " 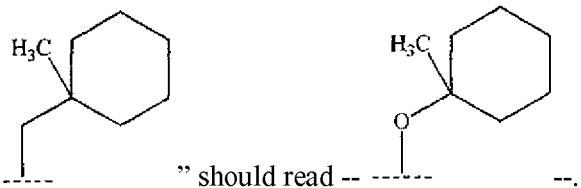 " should read -- --.

Signed and Sealed this
Twelfth Day of March, 2013

Teresa Stanek Rea
*Acting Director of the United States Patent and Trademark Office*

CERTIFICATE OF CORRECTION (continued)
U.S. Pat. No. 7,939,545 B2

Column 155

Claim 19, lines 51–56, compound 1106, " 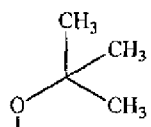 " should read -- 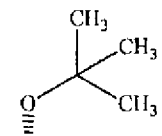 --.

Column 175
Claim 20, lines 33–40, cancel the text: